United States Patent
Schreck et al.

(10) Patent No.: US 9,629,644 B2
(45) Date of Patent: Apr. 25, 2017

(54) DEVICES AND METHODS FOR DILATING A PARANASAL SINUS OPENING AND FOR TREATING SINUSITIS

(75) Inventors: Thomas A. Schreck, Palo Alto, CA (US); Jerome E. Hester, Palo Alto, CA (US); David E. Edgren, Palo Alto, CA (US); Andrew I. Poutiatine, Palo Alto, CA (US); Curtis L. Rieser, San Jose, CA (US)

(73) Assignee: SinuSys Corporation, Palo Alto, CA (US)

( * ) Notice: Subject to any disclaimer, the term of this patent is extended or adjusted under 35 U.S.C. 154(b) by 1018 days.

(21) Appl. No.: 13/219,505

(22) Filed: Aug. 26, 2011

(65) Prior Publication Data
US 2012/0053567 A1    Mar. 1, 2012

Related U.S. Application Data

(60) Provisional application No. 61/378,360, filed on Aug. 30, 2010, provisional application No. 61/378,368, (Continued)

(51) Int. Cl.
*A61B 17/00* (2006.01)
*A61B 17/24* (2006.01)
(Continued)

(52) U.S. Cl.
CPC .......... *A61B 17/24* (2013.01); *A61B 17/3415* (2013.01); *A61B 17/3468* (2013.01);
(Continued)

(58) Field of Classification Search
CPC .......... A61M 29/02; A61M 2210/0618; A61M 2210/0681; A61M 29/00; A61B 17/1688; A61B 19/24; A61B 1/32
(Continued)

(56) References Cited

U.S. PATENT DOCUMENTS 3,625,351 A    12/1971   Eisenberg
3,732,865 A    5/1973    Higuchi et al.
(Continued)

FOREIGN PATENT DOCUMENTS

EP    0 923 912 A2    6/1999
JP    AH4-215768      2/1994
(Continued)

OTHER PUBLICATIONS

Mazzoli et al. (2004) "Use of self-expanding, hydrophilic osmotic expanders (hydrogel) in the reconstruction of congenital clinical anophthalmos," Database Medline XP002746291, Accession No. NLM15625905, 2 pgs.
(Continued)

*Primary Examiner* — Kevin C Sirmons
*Assistant Examiner* — William Carpenter
(74) *Attorney, Agent, or Firm* — Rudy J. Ng; Carol L. Francis; Bozicevic, Field & Francis LLP

(57) ABSTRACT

Medical devices which are adapted to be implanted into a patient for a limited period of time using minimally invasive insertion procedures for dilating a stenotic opening, such as a stenotic sinus opening, are provided. The devices and methods can be used for treating sinusitis and other nasal and/or sinus disorders.

49 Claims, 31 Drawing Sheets

Related U.S. Application Data filed on Aug. 30, 2010, provisional application No. 61/416,240, filed on Nov. 22, 2010, provisional application No. 61/416,248, filed on Nov. 22, 2010.

(51) Int. Cl.
*A61M 29/02* (2006.01)
*A61B 17/34* (2006.01)
*A61F 2/18* (2006.01)

(52) U.S. Cl.
CPC .............. *A61F 2/186* (2013.01); *A61M 29/02* (2013.01); *A61B 17/3478* (2013.01); *A61F 2210/0061* (2013.01); *A61M 2210/0618* (2013.01); *A61M 2210/0681* (2013.01)

(58) Field of Classification Search
USPC ................ 606/191, 192, 196, 198, 199
See application file for complete search history.

(56) References Cited

U.S. PATENT DOCUMENTS

| | | | |
|---|---|---|---|
| 3,760,805 A | 9/1973 | Higuchi | |
| 3,760,984 A | 9/1973 | Theeuwes | |
| 3,786,813 A | 1/1974 | Michaels | |
| 3,845,770 A | 11/1974 | Theeuwes et al. | |
| 4,014,334 A | 3/1977 | Theeuwes et al. | |
| 4,142,526 A | 3/1979 | Zaffaroni et al. | |
| 4,203,440 A | 5/1980 | Theeuwes | |
| 4,203,441 A | 5/1980 | Theeuwes | |
| 4,449,983 A | 5/1984 | Cortese | |
| 4,455,143 A | 6/1984 | Theeuwes | |
| 4,467,806 A * | 8/1984 | Bhiwandiwala et al. | 606/193 |
| 4,480,642 A * | 11/1984 | Stoy | A61M 29/02 128/839 |
| 4,663,148 A | 5/1987 | Eckenhoff et al. | |
| 5,160,743 A | 11/1992 | Edgren et al. | |
| 5,234,456 A | 8/1993 | Silvestrini | |
| 5,246,455 A | 9/1993 | Shikani | |
| 5,258,042 A | 11/1993 | Mehta | |
| 5,336,163 A | 8/1994 | DeMane et al. | |
| 5,413,572 A | 5/1995 | Wong et al. | |
| 5,423,745 A | 6/1995 | Todd et al. | |
| 5,464,450 A | 11/1995 | Buscemi et al. | |
| 5,496,368 A | 3/1996 | Wiese | |
| 5,498,255 A | 3/1996 | Wong | |
| 5,499,994 A * | 3/1996 | Tihon et al. | 606/192 |
| 5,500,013 A | 3/1996 | Buscemi et al. | |
| 5,547,378 A | 8/1996 | Linkow | |
| 5,674,241 A | 10/1997 | Bley et al. | |
| 5,693,065 A | 12/1997 | Rains, III | |
| 5,713,855 A | 2/1998 | Shippert | |
| 5,716,329 A * | 2/1998 | Dieter | A61B 1/32 600/184 |
| 5,728,396 A | 3/1998 | Peery et al. | |
| 6,056,720 A * | 5/2000 | Morse | A61M 25/10 604/96.01 |
| 6,123,697 A | 9/2000 | Shippert | |
| 6,224,907 B1 | 5/2001 | Davar et al. | |
| 6,270,787 B1 | 8/2001 | Ayer | |
| 6,336,496 B1 | 1/2002 | Asai et al. | |
| 6,387,124 B1 | 5/2002 | Buscemi et al. | |
| 6,455,065 B1 | 9/2002 | Hymes | |
| 6,648,873 B2 | 11/2003 | Arenberg et al. | |
| 6,753,011 B2 | 6/2004 | Faour | |
| 6,976,983 B2 | 12/2005 | Russell | |
| 7,014,636 B2 | 3/2006 | Gilbert | |
| 7,074,423 B2 | 7/2006 | Fereira et al. | |
| 7,108,684 B2 | 9/2006 | Farnan | |
| 7,108,762 B2 | 9/2006 | Russell | |
| 7,211,076 B2 | 5/2007 | Russell | |
| 7,235,068 B2 | 6/2007 | Theeuwes et al. | |
| 7,235,099 B1 | 6/2007 | Duncavage et al. | |
| 7,241,457 B2 | 7/2007 | Chen et al. | |
| 7,361,168 B2 | 4/2008 | Makower et al. | |
| 7,410,480 B2 | 8/2008 | Muni et al. | |
| 7,419,497 B2 | 9/2008 | Muni et al. | |
| 7,462,175 B2 | 12/2008 | Chang et al. | |
| 7,500,971 B2 | 3/2009 | Chang et al. | |
| 7,520,876 B2 | 4/2009 | Ressemann et al. | |
| 7,544,192 B2 | 6/2009 | Eaton et al. | |
| 7,591,830 B2 | 9/2009 | Rutter | |
| 7,645,272 B2 | 1/2010 | Chang et al. | |
| 7,654,997 B2 | 2/2010 | Makower et al. | |
| 7,655,257 B2 | 2/2010 | Peery et al. | |
| 7,678,099 B2 | 3/2010 | Ressemann et al. | |
| 7,678,103 B2 | 3/2010 | Russell | |
| 7,740,642 B2 | 6/2010 | Becker | |
| 7,740,643 B2 | 6/2010 | Maryanka | |
| 2002/0004060 A1 | 1/2002 | Heublein et al. | |
| 2002/0088723 A1 | 7/2002 | Lowry et al. | |
| 2002/0120276 A1 | 8/2002 | Greene et al. | |
| 2003/0171773 A1 | 9/2003 | Carrison | |
| 2004/0064150 A1 * | 4/2004 | Becker | 606/196 |
| 2004/0073299 A1 | 4/2004 | Hudson et al. | |
| 2004/0098095 A1 | 5/2004 | Burnside et al. | |
| 2004/0098108 A1 | 5/2004 | Harder et al. | |
| 2004/0116958 A1 | 6/2004 | Gopferich et al. | |
| 2004/0127871 A1 | 7/2004 | Odorzynski et al. | |
| 2004/0243214 A1 | 12/2004 | Farrell | |
| 2004/0267241 A1 | 12/2004 | Russell | |
| 2005/0054999 A1 | 3/2005 | Morman et al. | |
| 2005/0149173 A1 | 7/2005 | Hunter et al. | |
| 2005/0165379 A1 | 7/2005 | Mawad | |
| 2005/0240147 A1 | 10/2005 | Makower et al. | |
| 2005/0268573 A1 | 12/2005 | Yan | |
| 2005/0278012 A1 | 12/2005 | Vonderwalde | |
| 2006/0047247 A1 | 3/2006 | Anders | |
| 2006/0063973 A1 | 3/2006 | Makower et al. | |
| 2006/0095066 A1 * | 5/2006 | Chang et al. | 606/199 |
| 2006/0106361 A1 * | 5/2006 | Muni et al. | 604/500 |
| 2006/0276831 A1 | 12/2006 | Porter et al. | |
| 2007/0005094 A1 | 1/2007 | Eaton et al. | |
| 2007/0073269 A1 | 3/2007 | Becker | |
| 2007/0084144 A1 | 4/2007 | Labrecque et al. | |
| 2007/0106233 A1 | 5/2007 | Huang | |
| 2007/0129751 A1 * | 6/2007 | Muni et al. | 606/196 |
| 2007/0156251 A1 * | 7/2007 | Karmon | A61B 17/58 623/23.61 |
| 2007/0160647 A1 | 7/2007 | Pritchard et al. | |
| 2007/0233036 A1 | 10/2007 | Mandpe | |
| 2007/0244562 A1 | 10/2007 | Conner et al. | |
| 2007/0250105 A1 * | 10/2007 | Ressemann et al. | 606/196 |
| 2007/0269385 A1 | 11/2007 | Yun et al. | |
| 2007/0299392 A1 * | 12/2007 | Beyar | A61F 2/958 604/96.01 |
| 2008/0044553 A1 | 2/2008 | Freeman et al. | |
| 2008/0082045 A1 | 4/2008 | Goldfarb et al. | |
| 2008/0097468 A1 * | 4/2008 | Adams et al. | 606/119 |
| 2008/0125805 A1 | 5/2008 | Mische | |
| 2008/0243140 A1 | 10/2008 | Gopferich et al. | |
| 2008/0264102 A1 | 10/2008 | Berra | |
| 2008/0292255 A1 | 11/2008 | Stevens et al. | |
| 2009/0036968 A1 | 2/2009 | Hepworth et al. | |
| 2009/0098184 A1 | 4/2009 | Govil et al. | |
| 2009/0125046 A1 | 5/2009 | Becker | |
| 2009/0220571 A1 | 9/2009 | Eaton et al. | |
| 2009/0248141 A1 | 10/2009 | Shandas et al. | |
| 2009/0264976 A1 | 10/2009 | Nagasrinivasa | |
| 2009/0312745 A1 | 12/2009 | Goldfarb et al. | |
| 2009/0314676 A1 | 12/2009 | Peck et al. | |
| 2010/0030113 A1 | 2/2010 | Morriss et al. | |
| 2010/0076269 A1 | 3/2010 | Makower et al. | |
| 2010/0099946 A1 | 4/2010 | Jenkins et al. | |
| 2010/0100116 A1 | 4/2010 | Brister et al. | |
| 2010/0106255 A1 | 4/2010 | Dubin | |
| 2010/0155282 A1 | 6/2010 | Govil et al. | |
| 2010/0198191 A1 | 8/2010 | Clifford et al. | |
| 2010/0298862 A1 | 11/2010 | Chang et al. | |
| 2010/0305603 A1 | 12/2010 | Nielsen et al. | |
| 2010/0312101 A1 | 12/2010 | Drontle et al. | |
| 2010/0312338 A1 | 12/2010 | Gonzales et al. | |
| 2011/0004057 A1 | 1/2011 | Goldfarb et al. | |

(56) References Cited

U.S. PATENT DOCUMENTS

| | | |
|---|---|---|
| 2011/0021975 A1 | 1/2011 | Covello |
| 2011/0125091 A1 | 5/2011 | Abbate |
| 2012/0053404 A1 | 3/2012 | Schreck et al. |
| 2012/0071727 A1 | 3/2012 | Hanson et al. |
| 2012/0116350 A1 | 5/2012 | Strauss et al. |
| 2012/0261290 A1 | 10/2012 | Limjaroen et al. |
| 2013/0072958 A1 | 3/2013 | Ressemann et al. |
| 2013/0138132 A1 | 5/2013 | Phee et al. |
| 2013/0231693 A1 | 9/2013 | Edgren et al. |
| 2013/0253564 A1 | 9/2013 | Edgren et al. |
| 2013/0253567 A1 | 9/2013 | Edgren et al. |
| 2013/0261550 A1 | 10/2013 | Edgren et al. |
| 2013/0267987 A1 | 10/2013 | Edgren et al. |
| 2014/0031852 A1 | 1/2014 | Edgren et al. |
| 2014/0358177 A1 | 12/2014 | Schreck et al. |
| 2015/0065810 A1 | 3/2015 | Edgren et al. |

FOREIGN PATENT DOCUMENTS

| | | |
|---|---|---|
| JP | AH5-76602 | 8/1994 |
| WO | 9503848 A1 | 2/1995 |
| WO | 9829148 A1 | 7/1998 |
| WO | 9962430 | 12/1999 |
| WO | 0247558 A1 | 6/2002 |
| WO | 2005117755 | 12/2005 |
| WO | 2006034008 A2 | 3/2006 |
| WO | 2006020180 | 6/2006 |
| WO | 2007054108 | 5/2007 |
| WO | 2008008389 A2 | 1/2008 |
| WO | 2009018248 A1 | 2/2009 |
| WO | 2010033629 | 3/2010 |

OTHER PUBLICATIONS

Ronert et al. (2004) "The Beginning of a New Era in Tissue Expansion: Self-Filling Osmotic Tissue Expander—Four-Year Clinical Experience," Plastic and Reconstructive Surgery 114(5)1025-1031.

Merriam-Webster definition of "conduit" as accessed Oct. 6, 2016: http://www.merriam-webster.com/dictionary /conduit 1 page.

Merriam-Webster definition of "channel" as accessed Oct. 6, 2016; http;//www.merriam-webster.com/dictionary/channel 2 pages.

Sehgal et al., (1975) "Rapamycin (Ay-22,989), a new antifungal antibiotic. 11. Fermentation, isolation and characterization." J. Antibiot 28(10): 727-732. Abstract Only.

* cited by examiner

DEVICES AND METHODS FOR DILATING A PARANASAL SINUS OPENING AND FOR TREATING SINUSITIS

CROSS-REFERENCES TO RELATED APPLICATIONS

This application claims the benefit of priority under 35 U.S.C. §119(e) to U.S. Provisional Application Nos. 61/378,360 filed Aug. 30, 2010; 61/378,368 filed Aug. 30, 2010; 61/416,248 filed Nov. 22, 2010; and 61/416,240 filed Nov. 22, 2010, the disclosures of each of which are incorporated by reference herein in their entirety.

INTRODUCTION

The bones in the skull and face contain a series of air-filled cavities known as paranasal sinuses that are connected by passageways. The paranasal sinuses include frontal sinuses, sphenoid sinuses and maxillary sinuses. The paranasal sinuses are lined with mucus-producing epithelial tissue and are in communication with the nasal cavity. Normally, mucus produced by the epithelial tissue slowly drains out of each sinus through an opening known as an ostium. If the epithelial tissue of one of these passageways becomes inflamed for any reason, the cavities which drain through that passageway can become blocked. This blockage can be periodic (resulting in episodes of pain) or chronic. This interference with drainage of mucus (e.g., occlusion of a sinus ostium) can result in mucosal congestion within the paranasal sinuses. Chronic mucosal congestion of the sinuses can cause damage to the epithelium that lines the sinus with subsequent decreased oxygen tension and microbial growth (e.g., a sinus infection).

The term "sinusitis" refers generally to any inflammation or infection of the paranasal sinuses caused by bacteria, viruses, fungi (molds), allergies or combinations thereof. It has been estimated that chronic sinusitis (e.g., lasting more than 3 months) results in 18 million to 22 million physician office visits per year in the United States. Patients who suffer from sinusitis typically experience at least some of the following symptoms: headaches or facial pain, nasal congestion or post-nasal drainage, difficulty breathing through one or both nostrils, bad breath and/or pain in the upper teeth. Thus, one of the ways to treat sinusitis is by restoring the lost mucus flow.

SUMMARY

Medical devices which are adapted to be implanted into a patient for a limited period of time using minimally invasive insertion procedures for dilating a stenotic opening, such as a stenotic sinus opening, are provided. The devices and methods can be used for treating sinusitis and other nasal and/or sinus disorders.

Aspects of the present disclosure include a method of dilating a stenotic opening of a paranasal sinus in a subject. In certain embodiments, the method includes positioning a device in the stenotic opening, where the device includes an expandable portion configured to expand from a non-expanded configuration to an expanded configuration, where the non-expanded configuration is sized to be positioned within the stenotic opening, and a driver configured to expand the expandable portion from the non-expanded configuration to the expanded configuration over a period of 4 hours or more, where the expanded configuration dilates the stenotic opening.

In certain embodiments, the method includes removing the device from the stenotic opening at a point in time after the device has expanded to the expanded configuration.

In some instances, the paranasal sinus is a frontal sinus, a sphenoid sinus or a maxillary sinus.

In some cases, the device includes at least one anchor configured to maintain the device within the stenotic opening.

In certain instances, the method includes anchoring the device within the stenotic opening.

In certain embodiments, the driver is configured to expand the expandable portion by at least one of osmosis, a shape memory metal, a spring, a swellable polymer, a thermal expansion of a gas, a thermal expansion of a liquid, a gas-generating chemical reaction and a phase change expansion of a material.

In some cases, the device includes a conduit defining an interior lumen, where the conduit includes a distal end configured to be in fluid communication with an interior lumen of the paranasal sinus in the subject and a proximal end configured to be in fluid communication with a nasal cavity in the subject, and where the conduit is configured to allow fluid flow between the interior lumen of the paranasal sinus and the nasal cavity when the device is positioned within the stenotic opening.

In certain embodiments, the expandable portion includes a semipermeable membrane.

In some instances, the conduit includes a semipermeable membrane.

In some cases, the conduit includes an impermeable material.

In certain instances, the expandable portion includes an impermeable membrane.

In certain cases, the conduit includes a semipermeable membrane.

In certain embodiments, the method includes delivering a drug from the device while the device is positioned within the stenotic opening.

In some instances, the drug includes an antibiotic, an anti-inflammatory drug, a local anesthetic, an analgesic or a combination thereof.

In some cases, the drug is an antibiotic selected from the group consisting of levofloxacin, moxifloxacin, amoxicillin, clavulanic acid, clarithromycin, azithromycin, cefuroxime, ciprofloxacin, salts thereof and combinations thereof.

In certain cases, the drug is an anti-inflammatory drug selected from the group consisting of methylprednisolone, dexamethasone, salts thereof and combinations thereof.

In certain instances, the method is for the treatment of a subject having sinusitis. For example, certain embodiments include the device as described herein for use in the treatment of sinusitis.

In some instances, the driver is configured to expand the expandable portion from the non-expanded configuration to the expanded configuration over a period of 4 hours to 14 days.

In some embodiments, the driver is configured to expand the expandable portion from the non-expanded configuration to the expanded configuration over a period of 1 day to 10 days.

In certain cases, the driver is configured to expand the expandable portion from the non-expanded configuration to the expanded configuration over a period of 2 days to 8 days.

In some instances, the device includes a bioerodible material.

In certain cases, the non-expanded configuration has a diameter of 5 mm or less.

In certain embodiments, the paranasal sinus is a maxillary sinus and the expanded configuration has a diameter ranging from 5 mm to 10 mm.

In certain instances, the paranasal sinus is a frontal sinus and the expanded configuration has a diameter ranging from 3 mm to 5 mm.

In some instances, the paranasal sinus is a sphenoid sinus and the expanded configuration has a diameter ranging from 2 mm to 3 mm.

Aspects of the present disclosure also include a device for dilating a stenotic opening of a paranasal sinus in a subject. The device includes an expandable portion configured to expand from a non-expanded configuration to an expanded configuration, where the non-expanded configuration is sized to be positioned within the stenotic opening, and a driver configured to expand the expandable portion from the non-expanded configuration to the expanded configuration over a period of 4 hours or more, where the expanded configuration dilates the stenotic opening.

In certain embodiments, the paranasal sinus is a frontal sinus, a sphenoid sinus or a maxillary sinus.

In some instances, the device includes at least one anchor configured to maintain the device within the stenotic opening.

In certain cases, the driver is configured to expand the expandable portion by at least one of osmosis, a shape memory metal, a spring, a swellable polymer, a thermal expansion of a gas, a thermal expansion of a liquid, a gas-generating chemical reaction and a phase change expansion of a material.

In some instances, the device includes a conduit defining an interior lumen, where the conduit comprises a distal end configured to be in fluid communication with an interior lumen of the paranasal sinus in the subject and a proximal end configured to be in fluid communication with a nasal cavity in the subject, and where the conduit is configured to allow fluid flow between the interior lumen of the paranasal sinus and the nasal cavity when the device is positioned within the stenotic opening.

In some cases, the expandable portion includes a semipermeable membrane.

In some instances, the conduit includes a semipermeable membrane.

In certain cases, the conduit includes an impermeable material.

In some embodiments, the expandable portion includes an impermeable membrane.

In certain cases, the conduit includes a semipermeable membrane.

In some instances, the device includes a drug reservoir configured to deliver a drug while the device is positioned within the stenotic opening.

In certain embodiments, the drug comprises an antibiotic, an anti-inflammatory drug, a local anesthetic, an analgesic or a combination thereof.

In some cases, the drug is an antibiotic selected from the group consisting of levofloxacin, moxifloxacin, amoxicillin, clavulanic acid, clarithromycin, azithromycin, cefuroxime, ciprofloxacin, salts thereof and combinations thereof.

In certain cases, the drug is an anti-inflammatory drug selected from the group consisting of methylprednisolone, dexamethasone, salts thereof and combinations thereof.

In some cases, the device is configured for the treatment of a subject having sinusitis.

In some instances, the driver is configured to expand the expandable portion from the non-expanded configuration to the expanded configuration over a period of 4 hours to 14 days.

In some embodiments, the driver is configured to expand the expandable portion from the non-expanded configuration to the expanded configuration over a period of 1 day to 10 days.

In certain embodiments, the driver is configured to expand the expandable portion from the non-expanded configuration to the expanded configuration over a period of 2 days to 8 days.

In some instances, the device includes a bioerodible material.

In some cases, the device consists essentially of the bioerodible material.

In certain instances, the non-expanded configuration has a diameter of 5 mm or less.

In some cases, the paranasal sinus is a maxillary sinus and the expanded configuration has a diameter ranging from 5 mm to 10 mm.

In certain embodiments, the paranasal sinus is a frontal sinus and the expanded configuration has a diameter ranging from 3 mm to 5 mm.

In certain cases, the paranasal sinus is a sphenoid sinus and the expanded configuration has a diameter ranging from 2 mm to 3 mm.

Aspects of the present disclosure also include a device for dilating a stenotic opening of a paranasal sinus in a subject, where the device includes a self-expanding driver configured to expand an expandable portion from a non-expanded configuration to an expanded configuration, and the expandable portion disposed peripherally around the driver and configured to expand from the non-expanded configuration to the expanded configuration, where the non-expanded configuration is sized to be positioned within the stenotic opening.

In certain cases, the driver is configured to expand the expandable portion from the non-expanded configuration to the expanded configuration over a period of 0.5 hours or more.

In some instances, the driver is configured to expand the expandable portion from the non-expanded configuration to the expanded configuration over a period of 4 hours or more.

In some cases, the driver is configured to expand the expandable portion by at least one of osmosis, a shape memory metal, a spring, a swellable polymer, a thermal expansion of a gas, a thermal expansion of a liquid, a gas-generating chemical reaction and a phase change expansion of a material.

In certain cases, the driver includes an osmotically active agent.

In some cases, the expandable portion is configured to dilate the stenotic opening such that a greater amount of drainage is allowed through the stenotic opening as compared to the undilated stenotic opening.

In some instances, the device includes a conduit defining an interior lumen, where the conduit comprises a distal end configured to be in fluid communication with an interior lumen of the paranasal sinus in the subject and a proximal end configured to be in fluid communication with a nasal cavity in the subject, and where the conduit is configured to allow fluid flow between the interior lumen of the paranasal sinus and the nasal cavity when the device is positioned within the stenotic opening.

In certain instances, the expandable portion includes a semipermeable membrane.

In certain cases, the conduit includes a semipermeable membrane.

In some cases, the conduit includes an impermeable material.

In some instances, the expandable portion includes an impermeable membrane.

In some embodiments, the conduit includes a semipermeable membrane.

In certain embodiments, the device includes at least one of (i) a distal anchor proximate to the distal end of the device, and (ii) a proximal anchor proximate to the proximal end of the device, where the distal and proximal anchors are each configured to maintain the device within the stenotic opening.

In some instances, the device includes a drug reservoir configured to deliver a drug while the device is positioned within the stenotic opening.

In some cases, the drug includes an antibiotic, an anti-inflammatory drug, a local anesthetic, an analgesic or a combination thereof.

Aspects of the present disclosure also include a device for dilating a stenotic opening of a paranasal sinus in a subject, where the device includes: (a) an osmotic driver configured to expand an expandable portion from a non-expanded configuration to an expanded configuration; and (b) the expandable portion disposed peripherally around the driver and configured to expand from the non-expanded configuration to the expanded configuration, where the non-expanded configuration is sized to be positioned within the stenotic opening.

In certain embodiments, the driver is configured to expand the expandable portion from the non-expanded configuration to the expanded configuration over a period of 0.5 hours or more.

In certain cases, the driver is configured to expand the expandable portion from the non-expanded configuration to the expanded configuration over a period of 4 hours or more.

In some instances, the osmotic driver includes an osmotically active agent.

In some cases, the device includes a conduit defining an interior lumen, where the conduit comprises a distal end configured to be in fluid communication with an interior lumen of the paranasal sinus in the subject and a proximal end configured to be in fluid communication with a nasal cavity in the subject, and where the conduit is configured to allow fluid flow between the interior lumen of the paranasal sinus and the nasal cavity when the device is positioned within the stenotic opening.

In certain instances, the expandable portion includes a semipermeable membrane.

In some cases, the conduit includes a semipermeable membrane.

In certain embodiments, the conduit includes an impermeable material.

In certain cases, the expandable portion includes an impermeable membrane.

In some instances, the conduit includes a semipermeable membrane.

In some cases, the device includes at least one of (i) a distal anchor proximate to the distal end of the device, and (ii) a proximal anchor proximate to the proximal end of the device, where the distal and proximal anchors are each configured to maintain the device within the stenotic opening.

In certain cases, the device includes a drug reservoir configured to deliver a drug while the device is positioned within the stenotic opening.

In certain embodiments, the drug includes an antibiotic, an anti-inflammatory drug, a local anesthetic, an analgesic or a combination thereof.

Aspects of the present disclosure also include a device for dilating a stenotic opening of a paranasal sinus in a subject, where the device includes: (a) a conduit defining an interior lumen, where the conduit includes a distal end configured to be in fluid communication with an interior lumen of the paranasal sinus in the subject and a proximal end configured to be in fluid communication with a nasal cavity in the subject, and where the conduit is configured to allow fluid flow between the interior lumen of the paranasal sinus and the nasal cavity when the device is positioned within the stenotic opening; (b) a self-expanding driver disposed on an exterior surface of the conduit and configured to expand an expandable portion from a non-expanded configuration to an expanded configuration; and (c) the expandable portion disposed peripherally around the driver and configured to expand from the non-expanded configuration to the expanded configuration, where the non-expanded configuration is sized to be positioned within the stenotic opening.

In certain embodiments, the device includes at least one of (i) a distal anchor proximate to the distal end of the conduit and (ii) a proximal anchor proximate to the proximal end of the conduit, where the distal and proximal anchors are each configured to maintain the device within the stenotic opening.

In certain instances, the device includes a drug reservoir configured to deliver a drug while the device is positioned within the stenotic opening.

In some cases, the expandable portion includes a semipermeable membrane.

In some embodiments, the conduit includes a semipermeable membrane.

In certain instances, the conduit includes an impermeable material.

In some cases, the expandable portion includes an impermeable membrane.

In certain cases, the conduit includes a semipermeable membrane.

In some instances, the driver is configured to expand radially outward from the conduit.

In some embodiments, the driver includes an osmotically active agent.

In certain instances, the conduit is substantially non-collapsible.

Aspects of the present disclosure also include a kit including: (a) a device for dilating a stenotic opening of a paranasal sinus in a subject; and (b) instructions for using the device to dilate the stenotic opening. The device includes: (1) an expandable portion configured to expand from a non-expanded configuration to an expanded configuration, where the non-expanded configuration is sized to be positioned within the stenotic opening; and (2) an osmotic driver configured to expand the expandable portion from the non-expanded configuration to the expanded configuration over a period of 0.5 hours or more, where the expanded configuration dilates the stenotic opening; and In certain instances, the kit includes two or more devices.

In some instances, the kit includes a first device and a second device, where the expanded configuration of the second device has a diameter that is greater than the diameter of the expanded configuration of the first device.

In some cases, the kit includes one or more sinus ostium sizing probes for sizing the stenotic opening.

Aspects of the present disclosure also include a device for dilating a stenotic opening in a subject, where the device includes: (a) an osmotic driver configured to expand an expandable portion from a non-expanded configuration to an expanded configuration; and (b) the expandable portion disposed peripherally around the driver and configured to expand from the non-expanded configuration to the expanded configuration, where the non-expanded configuration is sized to be positioned within the stenotic opening.

In certain instances, the driver is self-expanding when in contact with tissue of the subject.

In some cases, the driver is configured to expand the expandable portion from the non-expanded configuration to the expanded configuration over a period of 0.5 hours or more.

In certain instances, the driver is configured to expand the expandable portion from the non-expanded configuration to the expanded configuration over a period of 4 hours or more.

In certain embodiments, the device includes a conduit defining an interior lumen, where the conduit is configured to allow fluid flow therethrough when the device is positioned within the stenotic opening.

In certain cases, the driver is disposed on an exterior surface of the conduit.

Aspects of the present disclosure also include a method of dilating a stenotic opening in a subject, where the method includes positioning a device in the stenotic opening. In certain embodiments, the device includes: (a) an osmotic driver configured to expand an expandable portion from a non-expanded configuration to an expanded configuration; and (b) the expandable portion disposed peripherally around the driver and configured to expand from the non-expanded configuration to the expanded configuration, where the non-expanded configuration is sized to be positioned within the stenotic opening, and where expansion of the device after said positioning facilitates dilation of the stenotic opening of the subject.

DETAILED DESCRIPTION

Devices

Figure 1:
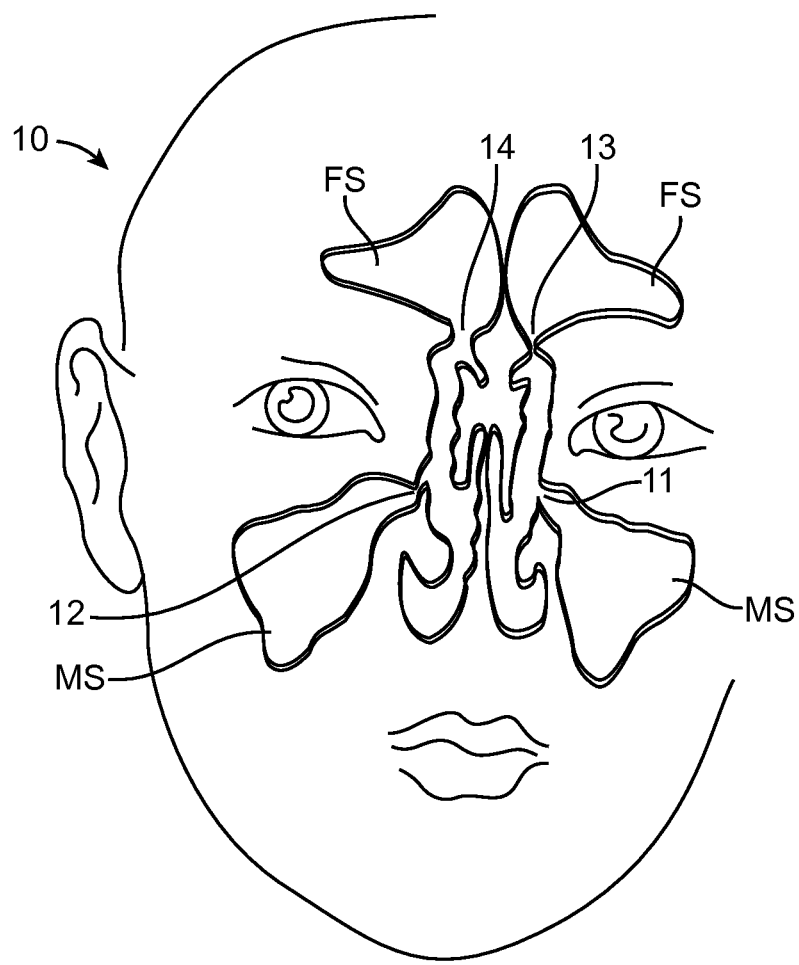
FIG. 1 is a partial cutaway view of a human head showing the positions of the frontal sinuses (FS) and the maxillary sinuses (MS)

Aspects of the present disclosure include a device for dilating a stenotic opening in a subject. The term "stenotic opening" refers to an abnormal narrowing of a biological passageway. In certain embodiments, the device includes an osmotic driver configured to expand an expandable portion from a non-expanded configuration to an expanded configuration, and the expandable portion disposed peripherally around the driver and configured to expand from the non-expanded configuration to the expanded configuration, where the non-expanded configuration is sized to be positioned within the stenotic opening. In certain embodiments, the driver is self-expanding when in contact with tissue of the subject. The driver may be configured to expand the expandable portion from the non-expanded configuration to the expanded configuration over a period of 0.5 hours or more, or the driver may be configured to expand the expandable portion from the non-expanded configuration to the expanded configuration over a period of 4 hours or more. In certain embodiments, the device includes a conduit defining an interior lumen, where the conduit is configured to allow fluid flow therethrough when the device is positioned within the stenotic opening. In some instances, the driver is disposed on an exterior surface of the conduit.

According to embodiments of the present disclosure, devices (also referred to as a sinus dilator) for dilating a stenotic opening of a paranasal sinus in a subject include an expandable portion and a driver. In certain embodiments, the driver is configured to expand from a non-expanded configuration to an expanded configuration. The driver may be configured to expand in volume from a non-expanded configuration to an expanded configuration. The non-expanded configuration of the device may be sized to be positioned within the stenotic opening. During use, the driver is configured to expand in size to an expanded configuration, where the expanded configuration dilates the stenotic opening.

In certain embodiments, the driver is configured to be a self-expanding driver. By "self-expanding" is meant that the driver may expand from the non-expanded configuration to the expanded configuration without external intervention from a user or a health care practitioner. For example, the self-expanding driver may be self-contained, such that the driver is configured to expand without connection to an external pressure source. As such, self-expanding drivers as described herein function without the need for an external pressure source or a pressure monitoring device. In some cases, the self-expanding driver expands from the non-expanded configuration to the expanded configuration upon absorbing fluid from the surrounding environment when the device is in use. For instance, the self-expanding driver may expand from the non-expanded configuration to the expanded configuration upon absorbing water from the surrounding tissues of the stenotic opening when the device is in use. Self-expanding drivers may be configured to expand the expandable portion of the device by various ways, such as, but not limited to, an osmotic agent, a swellable agent (e.g., a swellable polymer), combinations thereof, and the like.

In certain embodiments, the driver is configured to begin expanding upon insertion of the device into the stenotic opening of the subject. The terms "insert" or "insertion" and "implant" or "implantation" are used herein interchangeably to describe the positioning of a device in a stenotic opening of a subject for a period of time. In some instances, the driver is configured to begin expanding within seconds or minutes after insertion of the device into the stenotic opening. In some cases, the driver is configured to begin expanding in 60 min or less, such as 45 min or less, or 30 min or less, including 10 min or less, or 5 min or less, such as 1 min or less, after insertion of the device into the stenotic opening.

In some instances, the driver is configured to begin expanding after a period of time has elapsed after the device has been inserted into the stenotic opening of the subject. For example, the driver may be configured to begin expanding 30 min or more, such as 45 min or more, including 60 min or more, or 90 min or more, 120 min or more, or 180 min or more after the device has been inserted into the stenotic opening of the subject.

In certain embodiments, the driver includes a swellable agent. In some cases, the swellable agent may be configured to expand upon absorption of fluid from the surrounding tissues after insertion of the device into the stenotic opening of the subject. For example, the swellable agent may be configured to absorb water from the surrounding tissues and expand.

Swellable agents suitable for use in the driver include, but are not limited to, water swellable polymers such as thermoplastic urethane (TPU), poly ethylene oxide (PEO), hydroxypropylmethyl cellulose, polyvinyl alcohol, carboxymethylcellulose, sodium carboxymethylcellulose, poloxamer, polyethylene glycol, carbomer, methylcellulose, gelatin, xanthan gum, guar gum, amylose starches, alginates, and combinations thereof. In certain embodiments, the swellable agent may include, but is not limited to, the following: chemically cross-linked organic polymers, such as cross-linked sodium carboxymethyl cellulose (Ac-di-Sol; FMC Corp., Philadelphia, Pa.), and cross-linked polyvinyl pyrrolidone (PVP-XL; International Specialty Products, Wayne, N.J.); physically cross-linked organic polymers, such as low substituted hydroxypropyl cellulose (LHPC; Shin-Etsu Chemical Co., Ltd., New York, N.Y.), microcrystalline cellulose (FMC Corp., Philadelphia, Pa.), and powdered cellulose (Solka-Floc; International Fiber Corp., North Tonawanda, N.Y.); inorganic swelling agents, such as bentonite clay; combinations thereof; and the like.

In certain embodiments, the driver includes an osmotic agent. As used herein, the terms "osmotic agent," "osmotically active agent" and "osmoagent" are used interchangeably and refer to an agent that facilitates the imbibition of water from a region of high water potential (e.g., low solute concentration) through a semipermeable membrane to a region of low water potential (e.g., high solute concentration) until a state of dynamic equilibrium is reached. In some instances, the osmotically active agent may be configured to absorb water flowing through a semipermeable membrane from the surrounding tissues after insertion of the device into the stenotic opening of the subject and expand. Suitable osmotically active agents are described in more detail below. In certain embodiments, the osmotic agent is configured to have a zero order rate of expansion. By "zero order" is meant that the rate of volume expansion of the osmotic agent is approximately constant and is independent of the surrounding solute concentration.

Embodiments of the presently disclosed devices include an expandable portion. The expandable portion is configured to expand from a non-expanded configuration to an expanded configuration. In certain embodiments, the expandable portion is configured to expand in size from a non-expanded configuration to an expanded configuration. The expandable portion may be configured to expand in size without significantly increasing in volume, such as by stretching in one or more dimensions from the non-expanded configuration. The expandable portion may be positioned peripherally around the driver. For instance, the expandable portion may be disposed on an exterior surface of the driver. In these embodiments, expansion of the underlying driver expands the expandable portion from its non-expanded configuration to its expanded configuration.

Aspects of the present disclosure include devices that have an expandable portion, where the expandable portion includes a membrane. The membrane may be an elastic membrane, such that the membrane is configured to expand from the non-expanded configuration to the expanded configuration, as described herein. In certain instances, the membrane is a semipermeable membrane. By "semipermeable" is meant a membrane that is permeable to solvent but not significantly permeable to solute across a concentration gradient, such as a membrane that allows solvent (e.g., water) molecules to pass through the membrane by osmosis from a region of low solute concentration to a region of high solute concentration until a state of dynamic equilibrium is reached. For instance, a semipermeable membrane may be configured to allow water to pass through the membrane by osmosis from a region of low solute concentration (e.g., high water potential) to a region of high solute concentration (e.g., low water potential) until a state of dynamic equilibrium is reached.

In certain embodiments, the expandable portion includes a membrane, where the membrane is an impermeable membrane. By "impermeable" is meant a membrane that is not significantly permeable to solvent or solute. Impermeable membranes do not allow significant amounts of solvent (e.g., water) or solute molecules to pass through the membrane by osmosis even in the presence of a solute concentration gradient across the membrane.

In certain embodiments, the device includes a conduit that defines an interior lumen of the device. The conduit includes a distal end configured to be in fluid communication with an interior lumen of the paranasal sinus in the subject. As used herein, the term "distal" refers to the end of the device that is inserted through a paranasal sinus opening of the subject and remains within the sinus cavity during use. The conduit also includes a proximal end configured to be in fluid communication with a nasal cavity in the subject. As used herein, the term "proximal" refers to the end of the device that remains on the nasal cavity side of the stenotic opening when the device is positioned in the stenotic opening during use.

In some cases, the conduit may be configured to allow fluid flow between the paranasal sinus in the subject and the nasal cavity when the device is positioned within the stenotic opening. In some instances, the conduit is configured to allow fluid and/or air to flow from the paranasal sinus to the nasal cavity of the subject. For example, the conduit may be configured to facilitate drainage of fluid from the paranasal sinus in the subject to the nasal cavity when the device is positioned within the stenotic opening. In some cases, the conduit may be configured to facilitate the flow of air into and out of the paranasal sinus in the subject.

In certain embodiments, the driver is disposed on an exterior surface of the conduit. The driver may be disposed on the exterior surface of the conduit at a position between the distal end and the proximal end of the conduit. For example, the driver may be positioned between a distal anchor at the distal end of the conduit and a proximal anchor at the proximal end of the conduit. As described herein, the expandable portion may be positioned peripherally around the driver. Thus, in these embodiments, the driver is disposed between the exterior surface of the conduit and the overlying expandable portion. Expansion of the driver expands the overlying expandable portion from its non-expanded configuration to its expanded configuration.

Aspects of the driver further include embodiments where the driver completely surrounds the conduit. The driver may be disposed on the exterior surface of the conduit around the entire periphery of the conduit. In certain embodiments, the driver surrounds the conduit around the central portion of the conduit, where the distal end of the conduit may have a distal anchor and the proximal end of the conduit may have a proximal anchor, as described in more detail herein. In some instances, the driver includes one or more subunits, where each subunit is disposed on the exterior surface of the conduit. The one or more driver subunits may be positioned such that they are in contact with the adjacent one or more driver subunits. Alternatively, the one or more driver subunits may be positioned such that there is a channel between the driver subunits (see e.g., FIGS. 7-11). In certain instances, the channel between the driver subunits extends along the exterior surface of the conduit from the distal end of the conduit to the proximal end of the conduit. The channels may be configured to allow fluid and/or air to flow between the paranasal sinus and the nasal cavity of the subject. In certain cases, the channels are configured to allow fluid and/or air to flow from the paranasal sinus to the nasal cavity of the subject. For example, the channels may be configured to facilitate drainage of fluid from the paranasal sinus in the subject to the nasal cavity when the device is positioned within the stenotic opening. In some cases, the channels may be configured to facilitate the flow of air into and out of the paranasal sinus in the subject.

In certain embodiments, the walls of the conduit are substantially rigid. The walls of the conduit may be substantially rigid, such that the conduit maintains substantially the same shape and size during use of the device. For instance, the conduit may maintain substantially the same interior diameter during use of the device. In some instances, the walls of the conduit are substantially rigid, such that pressure exerted on the exterior surface of the conduit by the driver does not significantly decrease the interior diameter of the conduit. For example, the walls of the conduit may be substantially rigid, such that the conduit is not crushed by the driver during use of the device. In some instances, the driver is configured to expand radially outward from the conduit. As discussed above, the walls of the conduit may be substantially rigid, thus expansion of the driver may be directed radially outward away from the substantially rigid walls of the conduit. Expansion of the driver radially outward from the conduit may facilitate dilation of the stenotic opening.

In certain embodiments, the walls of the conduit are substantially non-collapsible. The walls of the conduit may be substantially non-collapsible, such that the conduit is configured to maintain an opening in the conduit during use of the device. For example, the walls of the conduit may be substantially non-collapsible, such that the conduit is not crushed by the driver during use of the device. In some cases, a non-collapsible conduit maintains substantially the same shape and size during use of the device. For instance, the conduit may maintain substantially the same interior diameter during use of the device. In some instances, the walls of the conduit are substantially non-collapsible, such that pressure exerted on the exterior surface of the conduit by the driver does not significantly decrease the interior diameter of the conduit. As discussed above, the driver may be configured to expand radially outward from the conduit and, as such, the walls of the conduit may be substantially non-collapsible, such that expansion of the driver is directed radially outward away from the substantially non-collapsible walls of the conduit. Expansion of the driver radially outward from the conduit may facilitate dilation of the stenotic opening. A substantially non-collapsible conduit may be rigid, as described above, or may be flexible and adapted to bend from its original shape. In some instances, a flexible conduit facilitates insertion of the sinus dilator in a sinus ostium.

In certain instances, the conduit includes a membrane. The conduit membrane may be a semipermeable membrane. In certain instances, the conduit membrane is a non-collapsible semipermeable membrane. In some cases, the conduit membrane is a rigid semipermeable membrane. The membrane may be configured to be permeable to solvent but not significantly permeable to solute across a concentration gradient, such that the membrane allows solvent (e.g., water) molecules to pass through the membrane by osmosis from a region of low solute concentration to a region of high solute concentration until a state of dynamic equilibrium is reached. For instance, the membrane may be configured to allow water to pass through the membrane by osmosis from an interior lumen of the conduit to the surrounding driver until a state of dynamic equilibrium is reached.

In some embodiments, the device includes a conduit that includes a semipermeable membrane, a surrounding driver, and an overlying expandable portion that includes a semipermeable membrane. In these embodiments, the device may be configured to allow solvent (e.g., water) to pass through both the semipermeable expandable portion membrane by osmosis and through the semipermeable conduit membrane by osmosis. For example, the device may be configured to allow solvent to pass through the semipermeable expandable membrane from the surrounding tissues to the underlying driver, and also allow solvent to pass through the semipermeable conduit membrane from an interior lumen of the conduit to the surrounding driver.

In other embodiments, the device includes a conduit that includes a semipermeable membrane, a surrounding driver, and an overlying expandable portion that includes an impermeable membrane. In these embodiments, the device may be configured to allow solvent (e.g., water) to pass through the semipermeable conduit membrane by osmosis but not allow significant amounts of solvent (e.g., water) to pass through the impermeable expandable portion membrane. For example, the device may be configured to allow solvent to pass through the semipermeable conduit membrane from an interior lumen of the conduit to the surrounding driver, but not allow significant amount of solvent to pass through the impermeable expandable portion membrane to the driver.

In yet other embodiments, the conduit includes an impermeable material. In some cases, the impermeable material is an impermeable membrane. For instance, the device may include a conduit that includes an impermeable membrane, a surrounding driver, and an overlying expandable portion that includes a semipermeable membrane. In these embodiments, the device may be configured to allow solvent (e.g., water) to pass through the semipermeable expandable membrane by osmosis but not allow significant amounts of solvent (e.g., water) to pass through the impermeable conduit membrane. For example, the device may be configured to allow solvent to pass through the semipermeable expandable portion membrane from the surrounding tissues to the underlying driver, but not allow significant amount of solvent to pass through the impermeable conduit membrane from the interior lumen of the conduit to the surrounding driver.

Aspects of the device may include a distal anchor configured to maintain the device within the stenotic opening during use of the device. The distal anchor may be connected to the device proximate to the distal end of the device. For example, the distal anchor may be connected to the device proximate to the distal end of the conduit. In some cases, the distal anchor is configured to prevent the device from premature explantation from the stenotic opening. The distal anchor may facilitate maintaining the device within the stenotic opening for a desired period of time until the device is removed from the stenotic opening by the user or a health care professional. In certain embodiments, the distal anchor is a mechanical anchor, such as, but not limited to, a hook, a barb, a clamp, a tether and the like. In certain cases, the distal anchor is configured to maintain the device within the stenotic opening by having a diameter that is greater than the diameter of the stenotic opening.

In some instances, the device has a frictional surface on an exterior surface of the device. The frictional surface may be configured to increase the friction between the exterior surface of the device and the surrounding tissues when the device is in use. Increasing the friction between the exterior surface of the device and the surrounding tissues may facilitate retention of the device in the stenotic opening of the subject during use. For example, the frictional surface may have a rough topography that includes an exterior surface shaped as, for example, washboard, rings, waffle pattern, snow tire pattern, pebble finish, shark skin texture, combinations thereof, and the like.

In certain cases, the device includes an adhesive disposed on an exterior surface of the device. In some cases, the membrane includes an adhesive. The membrane may be configured such that the adhesive elutes to the external surface of the device during use. The adhesive may facilitate retention of the device in the stenotic opening of the patient during use. Examples of suitable adhesives include, but are not limited to, carbomer, low molecular weight hydroxypropyl methylcellulose, combinations thereof, and the like.

In some cases, the distal anchor is configured to allow the device to be inserted into the stenotic opening. The distal anchor may have an outside diameter that is substantially the same as the outside diameter of the device when the device is in a non-expanded configuration. In some instances, the distal anchor has an outside diameter that is greater than the diameter of the conduit. In certain embodiments, the distal anchor has a tapered shape, such that the distal end of the distal anchor has a diameter that is less than the diameter of the proximal end of the distal anchor (see e.g., FIGS. 5 and 6). In certain embodiments, the distal anchor is configured such that the distal anchor has a diameter that is smaller during insertion of the device into the stenotic opening as compared to the diameter of the distal anchor after the anchor portion of the device has been inserted into the paranasal sinus.

In certain embodiments, the distal anchor is a flexible anchor. In some cases, the flexible distal anchor is configured to have a configuration that has a smaller diameter during insertion of the device into the stenotic opening as compared to the diameter of the flexible distal anchor after the anchor portion of the device has been inserted into the paranasal sinus. For instance, the flexible distal anchor may be configured to fold into a configuration that has a smaller diameter during insertion of the device into the stenotic opening as compared to the diameter of the flexible distal anchor after the anchor portion of the device has been inserted into the paranasal sinus. An example of an embodiment having flexible anchors is shown in FIGS. 3, 4, 7 and 8. The distal anchor may include one or more subunits that are connected to and extend radially outward from the conduit. The subunits of the distal anchor may be flexible, such that during insertion of the device into the stenotic opening, the subunits fold into a configuration where the distal anchor has an outside diameter that is less than the diameter of the distal anchor when the subunits are fully extended. Once the distal end of the device has been inserted into the paranasal sinus, the subunits may be free to unfold back to their extended configuration, thus anchoring the device within the stenotic opening.

Aspects of the device may include a proximal anchor configured to maintain the device within the stenotic opening during use of the device (see e.g., FIGS. 3-7). The proximal anchor may be connected to the device proximate to the proximal end of the device. For example, the proximal anchor may be connected to the device proximate to the proximal end of the conduit. In some cases, the proximal anchor is configured to prevent the device from being inserted too far or completely into the paranasal sinus of the subject. The proximal anchor may facilitate maintaining the device within the stenotic opening for a desired period of time until the device is removed from the stenotic opening by the user or a health care professional. In some cases, the proximal anchor has an outside diameter that is greater than the diameter of the conduit. For instance, the proximal anchor may have an outside diameter that is greater than the diameter of the device when the device is in a non-expanded configuration.

In some embodiments, the device includes an attachment portion configured to facilitate removal of the device from the stenotic opening. The attachment portion may be configured to allow a removal device to be attached to the device. For example, the attachment portion of the device may include a structure, such as, but not limited to, a loop, a tether or a hook. The removal device may include a corresponding structure that allows for attachment of the removal device to the attachment portion of the device. In some instances, the device includes a loop and the removal device includes a hook. In other embodiments, the device includes a hook and the removal device includes a loop. In either embodiment, insertion of the hook into the loop connects the device to the removal device and may facilitate removal of the device from the stenotic opening.

In some cases, the attachment portion may protrude from the device to facilitate connection of the removal device to the attachment portion of the device. The attachment portion may be disposed at or near the proximal end of the device to facilitate removal of the device from the stenotic opening. For example, the attachment portion may be disposed on the proximal anchor at the proximal end of the device. In certain cases, the attachment portion may be connected to the conduit proximate to the proximal end of the device.

In certain embodiments, the device includes one or more drug reservoirs configured to deliver a drug to the subject while the device is positioned within the stenotic opening. The drug reservoir may be configured to deliver the drug locally to the tissues surrounding the device while the device is in use. For example, the drug reservoir may be configured to deliver the drug to one or more of the interior tissues of the stenotic opening, the interior lumen of the paranasal sinus, the tissues of the stenotic opening, the exterior tissues of the stenotic opening, and the nasal cavity.

The one or more drug reservoirs may have a variety of different configurations. In some instances, the one or more drug reservoirs are disposed on the exterior surface of the conduit. In certain cases, the one or more drug reservoirs are disposed on the exterior surface of the expandable portion of the device. The one or more drug reservoirs may be positioned between the expandable portion and the driver. The one or more drug reservoirs may be within the driver. Various combinations of the above described drug reservoir configurations are also possible and may depend of the type of drug to be delivered, the desired site of activity for the drug, the patient, the size of the stenotic opening, the desired configuration for the device, and the like. For example, in some embodiments, the device includes a first drug reservoir near the distal end of the device and a second drug reservoir near the proximal end of the device. The first drug reservoir may be disposed between the distal anchor and the driver, and the second drug reservoir may be disposed between the proximal anchor and the driver. In some instances, the drug reservoir is disposed distal to the distal anchor of the device. In these instances, positioning of the drug reservoir distal to the distal anchor of the device may facilitate delivery of the drug to one or more of the interior tissues of the stenotic opening, the interior lumen of the paranasal sinus, and the like.

In certain embodiments, the drug reservoir is configured to deliver the drug from the drug reservoir to the surrounding tissue. In some embodiments, the drug reservoir is configured to allow the drug to passively diffuse from the drug reservoir. In other embodiments, the drug reservoir is configured to actively deliver the drug to the surrounding tissue. For example, the drug reservoir may include an osmotically active agent and may be configured to deliver the drug from the drug reservoir through the action of the osmotically active agent after the device has been positioned in the stenotic opening of the subject. In certain embodiments, the device may be configured to deliver the drug from the drug reservoir through the action of the driver. In embodiments where the driver includes a swellable polymer or an osmotically active agent, expansion of the driver may apply external pressure on the drug reservoir and push the drug out of the drug reservoir. For example, as discussed above, the drug reservoir may be positioned between the proximal anchor and the driver (or between the distal anchor and the driver). Expansion of the driver may compress the drug reservoir against the proximal anchor (or the distal anchor) and thus force the drug out of the drug reservoir.

Referring now to FIG. 1, there is shown a human patient 10 having two frontal sinuses (FS) and two maxillary sinuses (MS). Each of these four sinuses has an opening which can be accessed by way of the patient's nostrils. The openings include maxillary sinus openings 11 and 12, of which opening 11 is shown in a normal open condition and opening 12 shown in an occluded or stenotic condition. Similarly, the patient 10 has frontal sinus openings 13 and 14, of which opening 14 is shown in a normal open condition and opening 13 is shown in an occluded or stenotic condition.

Figure 2:
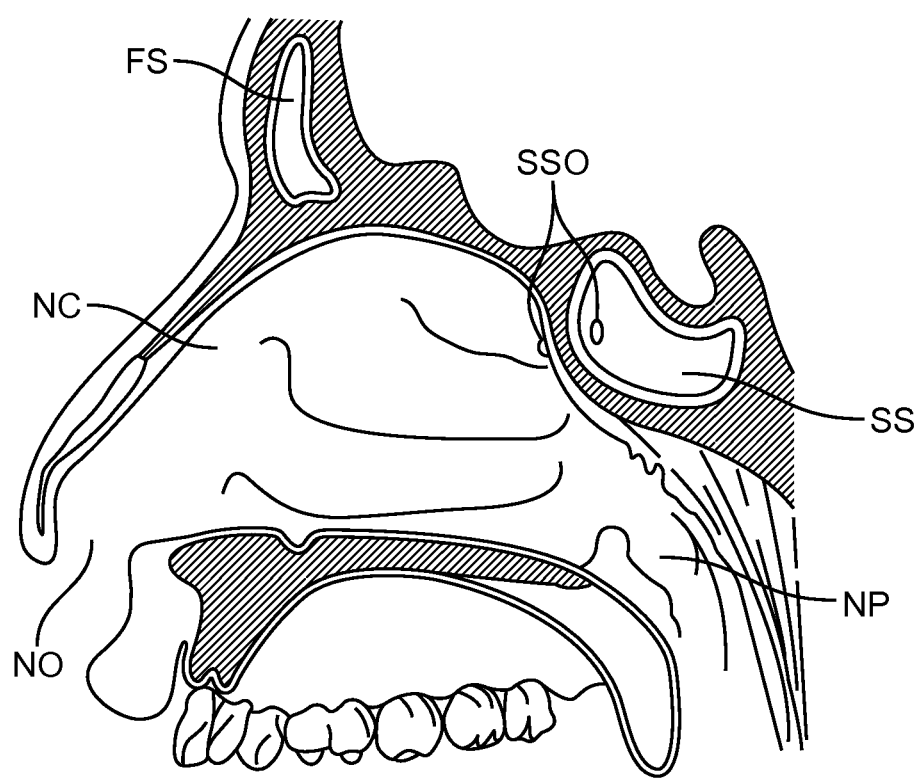
FIG. 2 is a sectional view of a portion of a human head showing the positions of the frontal sinus (FS) and the sphenoid sinus (SS)

Referring now to FIG. 2, there is shown a sectional view of a patient's nose and sinuses including the nasal cavity (NC), the nasopharynx (NP), the nostril opening (NO), the frontal sinus (FS), the sphenoid sinus (SS) and the sphenoid sinus opening (SSO).

Figure 3:
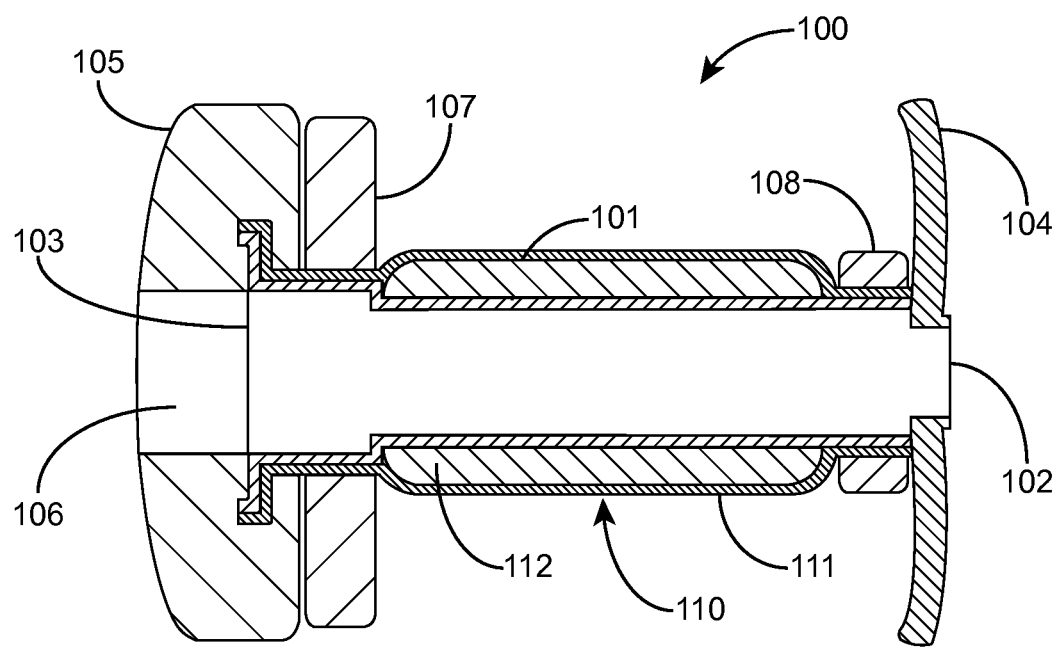
FIG. 3 is a sectional view of an osmotically driven device for dilating a paranasal sinus opening, in a non-expanded configuration, according to embodiments of the present disclosure.
Figure 4:
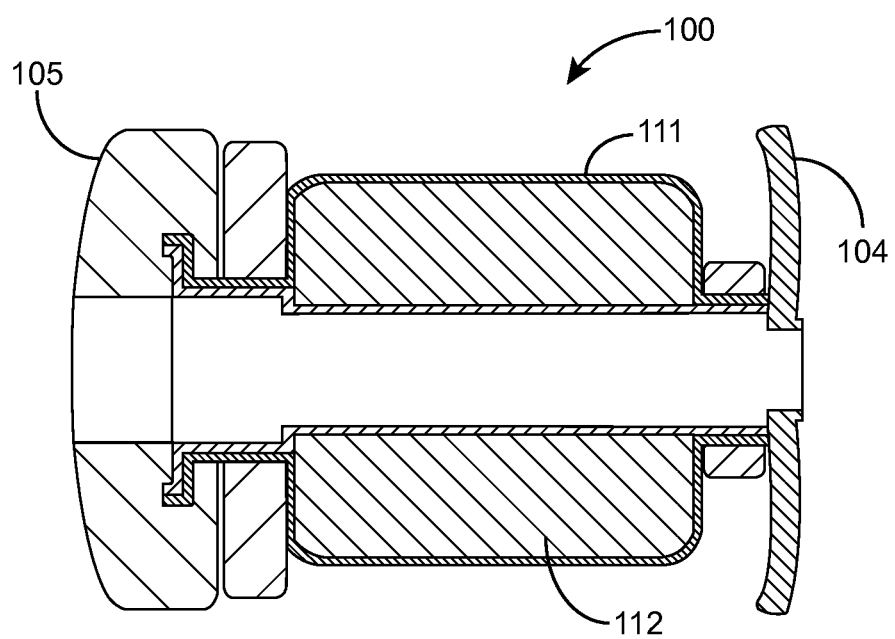
FIG. 4 is a sectional view of the device shown in FIG. 3, in an expanded configuration, according to embodiments of the present disclosure.

An embodiment of an implantable dilation device 100 is shown in FIGS. 3 and 4. FIG. 3 shows the device 100 in a non-expanded configuration which is the configuration at the time the device is positioned within a sinus opening. FIG. 4 shows the device 100 in an expanded configuration that is achieved after the device has been in place within a sinus opening. Device 100 includes a conduit 101 having a distal opening 102 and a proximal opening 103. As is explained in more detail herein, conduit 101 has an inner diameter of 0.5 mm or more in order to permit bodily fluids such as mucus, puss and blood to drain out of the sinus and air to pass into and out of the sinus cavity while the device 100 is positioned within the sinus opening. For those applications where sinus drainage is not a concern, or for shorter implantation durations, the conduit 101 can be replaced by a solid member, e.g., a solid rod made of plastic or metal. The conduit 101 is non-collapsible under the pressures exerted by the osmotic driver 110 during use, so that as osmotic pressure is generated within driver 110, it causes the device to expand outward from the conduit 101 rather than causing the conduit 101 to collapse or significantly decrease in diameter.

Figure 7:
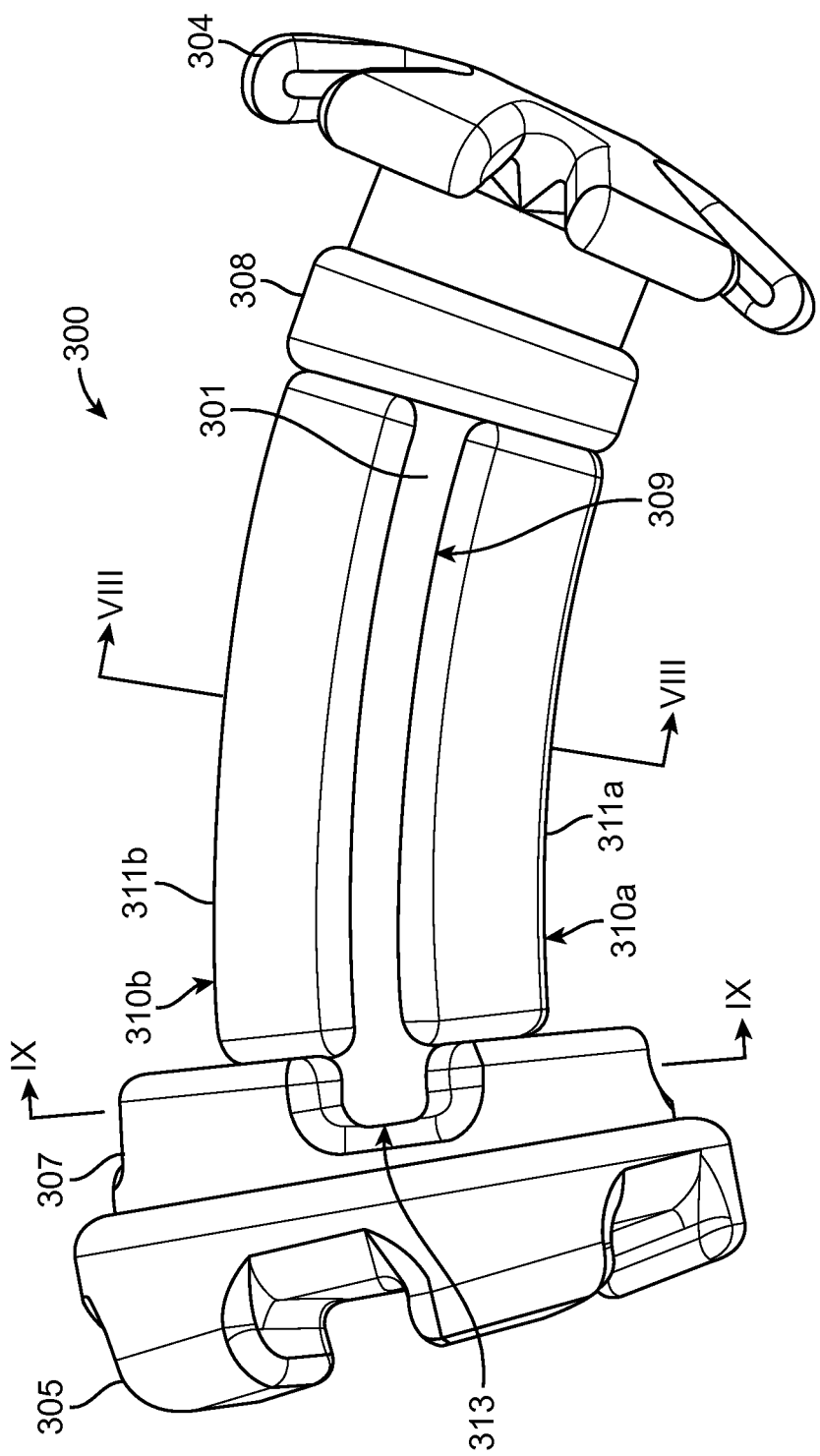
FIG. 7 is a side perspective view of an embodiment of an osmotically driven device for dilating a paranasal sinus opening, in a non-expanded configuration, according to embodiments of the present disclosure.
Figure 8:
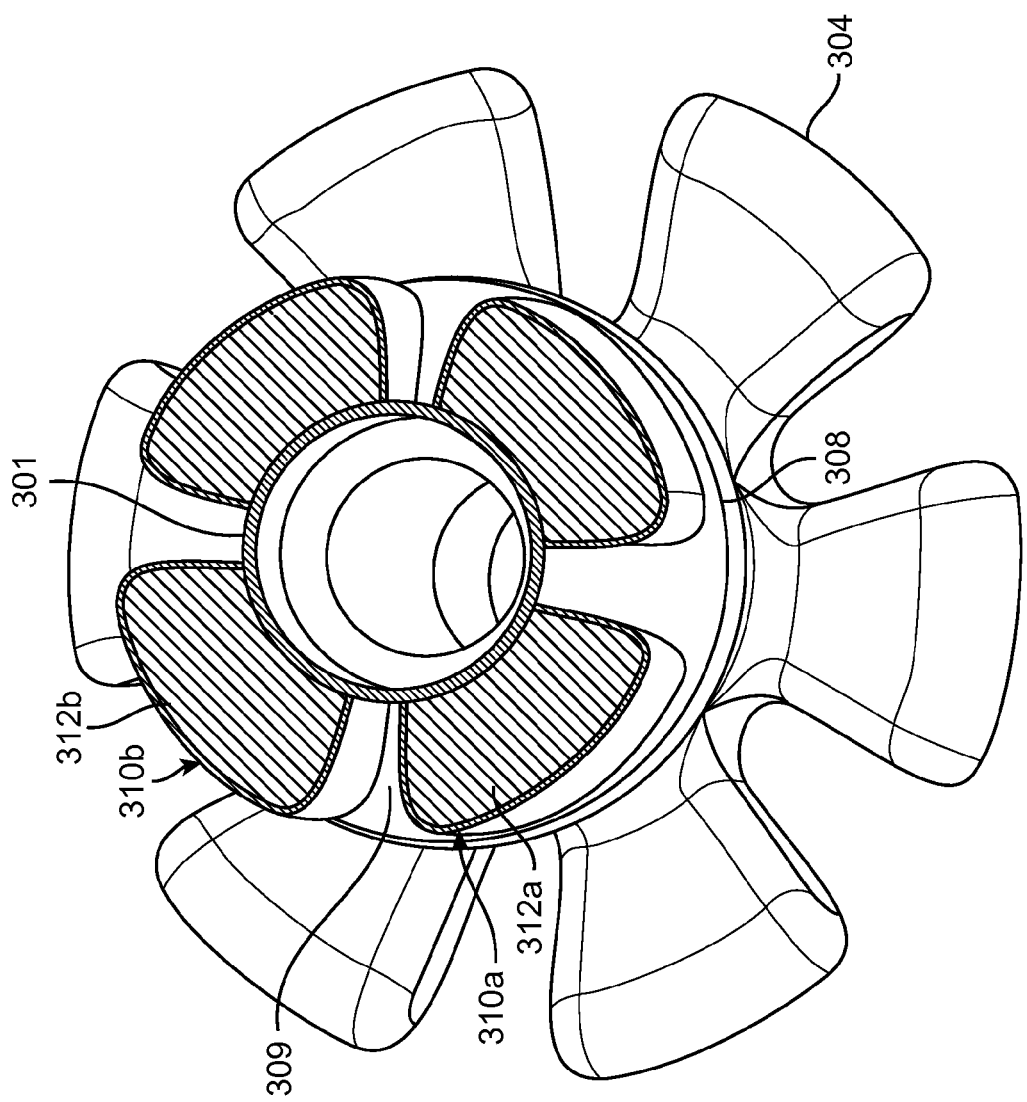
FIG. 8 is a sectional view of the device shown in FIG. 7, taken along line VIII-VIII, according to embodiments of the present disclosure.

Positioned at the distal opening 102 is a flexible distal anchor 104. As used herein, the term "distal" refers to the end of the device that is inserted through a paranasal sinus opening of the subject and remains within the sinus cavity during use. Distal anchor 104 can have a daisy configuration as shown in FIGS. 7 and 8 with flexible petals that can fold back onto the device 100 as the distal end of the device is inserted through a sinus opening. Once inserted through the opening, the petals spring back up and help keep the device from being prematurely expelled from the sinus opening into the nasal cavity.

Similarly, attached to the proximal end 103 of conduit 101 is a proximal anchor 105 having a central passageway 106 which aligns with the hollow interior of conduit 101. As used herein, the term "proximal" refers to the end of the device that remains on the nasal cavity side of the stenotic opening when the device is positioned in the stenotic opening during use. Proximal anchor 105 has an expanded diameter compared to the diameter of conduit 101 and thereby acts as a second anchor for preventing the device 100 from entering into the nasal sinus cavity during use. In certain embodiments, the opening 102, leading to the hollow interior of conduit 101 and the aligned opening 106 create a conduit or passageway for fluid in the sinus cavity, such as mucus, puss and/or blood, to drain through the device 100 while the device 100 is positioned within the sinus opening.

Positioned along a central portion of conduit 101 (e.g., between the distal anchor 104 and the proximal anchor 105) is an osmotic driver 110 that includes an elastic semipermeable membrane 111 surrounding an osmotic core 112. The osmotic core 112 may include one or more osmotically active agents such as water soluble salts or sugars, such as sodium chloride, lactose, etc., and optionally binders, lubricants and mold release agents. The osmotic core additionally may include osmopolymers such as polyethylene oxide, sodium carboxymethyl cellulose, and the like. Once inserted into a paranasal sinus opening, water from the patient's body permeates through the membrane 111 by osmosis and forms a solution of the salt or sugar and hydrates the osmopolymer in the osmotic core 112, thereby causing the osmotic core 112 to expand. As water imbibes in, the volume of the core 112 increases. In addition, due to its elastic nature, the membrane 111 also expands to accommodate the increased volume of the osmotic core 112. The rate of water permeation can be controlled by controlling the composition, thickness and porosity of the membrane 111, in combination with the osmotic activity of the core 112. In certain embodiments of the devices disclosed herein, the membrane 111 composition, thickness and porosity are controlled to achieve expansion of the core 112 over a period of 0.5 hours or more, such as 1 hour or more, including 2 hours or more, or 3 hours or more, or 4 hours or more. In other embodiments of the devices disclosed herein, the membrane 111 composition, thickness and porosity are controlled to achieve expansion of the core 112 over a period of 4 hours or more. In some cases, the expansion will occur gradually over a period of 4 hours to 14 days, such as over a period of 6 hours to 12 days, including over a period of 1 to 10 days, for example, the expansion may occur gradually over a period of 2 to 8 days. In this way the rapid expansion and the resulting pain experienced by the patient during conventional balloon sinuplasty may be substantially avoided.

Certain embodiments of the osmotic core include ring (e.g., donut) shaped salt- and polymer-containing tablets having an inner opening that is large enough to slide over conduit 101. In some instances, the tablets have an outer diameter of 5 mm or less, such as 4 mm or less, or 3 mm or less, or 2 mm or less, or 1 mm or less. For instance, the tablets may have an outer diameter of 3 mm. In some instances, the tablets are composed of a salt (e.g., NaCl). In certain cases, the tablets are composed of a polymer, such as a high molecular weight hydrogel-forming polymer, for example polyethylene oxide (e.g., Polyox™, Dow Chemical Company, Midland, Mich.). In certain cases, the tablets include tableting excipients and/or lubricants. In some embodiments, the tablets include 10 to 95 wt % salt, such as 20 to 90 wt % salt, including 30 to 80 wt % salt, or 40 to 70 wt % salt. For example, the tablets may include 10 to 95 wt % NaCl, such as 20 to 90 wt % NaCl, including 30 to 80 wt % NaCl, or 40 to 70 wt % NaCl. In some cases, the tablets include 30 to 80 wt % NaCl. In certain embodiments, the tablets include 5 to 90 wt % polymer, such as 10 to 80 wt % polymer, including 20 to 70 wt % polymer, or 30 to 60 wt % polymer. For example, the tablets may include 5 to 90 wt % Polyox, such as 10 to 80 wt % Polyox, including 20 to 70 wt % Polyox, or 30 to 60 wt % Polyox. In certain cases, the tablets include 20 to 70 wt % Polyox. In some embodiments, the tablets are composed of a salt and a polymer, as described above. For example, the tablets may include 30 to 80 wt % NaCl and 20 to 70 wt % Polyox. In certain instances, the NaCl gives a quicker rate of expansion than does the Polyox, though both materials are osmotically active and cause water to be imbibed into the interior of the dilator. Because of its low molecular weight, there may be some leakage of NaCl out through the semipermeable membrane, whereas because of its high molecular weight, there is substantially no leakage of the Polyox out through the semipermeable membrane. A higher NaCl loading (e.g., 80 wt %) gives a longer duration of dilator expansion than a lower NaCl loading (e.g., 20 wt %).

Referring now to FIG. 4, there is shown an embodiment of device 100 after it has been in place within a paranasal sinus opening. As can be seen by a comparison with the device 100 shown in FIG. 3, the volume of the osmotic core 112 has expanded due to the imbibed water and the elastic semipermeable membrane 111 has expanded to accommodate this increased volume. In this way, the diameter of the core 112 has increased and when in place within the stenotic sinus opening exerts a radially outward force thereon, causing the sinus opening to dilate. The distal anchor 104 and the proximal anchor 105 facilitate maintaining the device 100 positioned within the sinus opening during this radial expansion.

Also shown in FIGS. 3 and 4 are optional drug releasing reservoirs 107 and 108. Reservoir 107 is positioned near the proximal end of the device and may be configured to release drug at the nasal cavity side of the sinus opening. Reservoir 108 is positioned near the distal end of the device and may be adapted to release drug into the paranasal sinus. The reservoirs can be made from drug releasing materials including drug eluting polymers, bioerodible polymers such as PLGA, osmotically driven drug delivery systems, and sponges and similar matrices that are preloaded with drug, or in which a drug is added by the physician immediately before use of device 100. The drugs in reservoirs 107 and 108 may be selected from antibiotics, anti-inflammatory drugs, anesthetics (e.g., local anesthetics), analgesics (e.g., locally acting analgesics), drugs that reduce bleeding (e.g., vasoconstrictors), combinations thereof, and the like. In certain embodiments, antibiotics include levofloxacin, moxifloxacin, amoxicillin, clavulanic acid, clarithromycin, azithromycin, cefuroxime, ciprofloxacin, salts thereof and combinations thereof and the like. In some instances, anti-inflammatory drugs include methylprednisolone, dexamethasone, salts thereof and combinations thereof and the like. In some cases, local anesthetics include lidocaine, bupivacaine, ropivacaine, tetracaine, salts thereof and combinations thereof and the like. In certain embodiments, locally acting analgesics include: acetaminophen; Cox-2 inhibitors, such as celecoxib and rofecoxib and the like; NSAIDS such as diclofenac, ibuprofen, ketoprofen, naproxen, piroxicam, aspirin and the like; opioids such as morphine; opioid agonists such as tramadol and the like. In certain embodiments, vasoconstrictors include oxymetazoline, epinephrine, tranexamic acid, salts thereof, combinations thereof, and the like. In certain instances, the drug reservoirs may include a combination of drugs, such as a combination of an NSAID, an anti-inflammatory drug and a vasoconstrictor. For example, the drug may include OMS103HP (Omeros Corp., Seattle, Wash.), which includes an NSAID (ketoprofen), an anti-inflammatory drug (amitriptyline) and a vasoconstrictor (oxymetazoline). Alternatively or in addition to the drug reservoirs 107 and 108, the device 100 may include a drug on the exterior surface of the device. For example, the device 100 can be sprayed, dipped or coated with a drug solution or gel formulation that includes a drug prior to placement of device 100 within the patient.

In certain embodiments, reservoirs 107 and 108 are composed of substantially rigid materials. In these embodiments, the reservoirs assist in directing the expansion of osmotic driver 110 in a radially outward direction, rather than in a direction that is parallel to the longitudinal axis of device 100.

An alternate configuration of an insertable dilation device, similar to device 100 shown in FIGS. 3 and 4, has a rigid or non-collapsible tubular semipermeable membrane in place of impermeable conduit 101 and an elastic impermeable membrane in place of elastic semipermeable membrane 111. Such a device expands by reason of water vapor present in the lumen of the tubular semipermeable membrane. In certain embodiments, under similar conditions, osmotic engine water absorption from 100% relative humidity water vapor is about two orders of magnitude lower than when the same osmotic engine is in contact with bulk water. The use of an "interior" semipermeable osmotic membrane, as described above, may be adapted for applications where the dilation device expansion takes place over a longer period of time, such as days to weeks. For applications where dilation device expansion takes place over a shorter period of time (e.g., hours), an internal semipermeable membrane dilation device may utilize a water wicking element, for example a hydrophilic fabric or similar material, within the interior lumen of the tubular membrane and optionally extending out past the proximal and/or distal ends of the dilation device.

Figure 5:
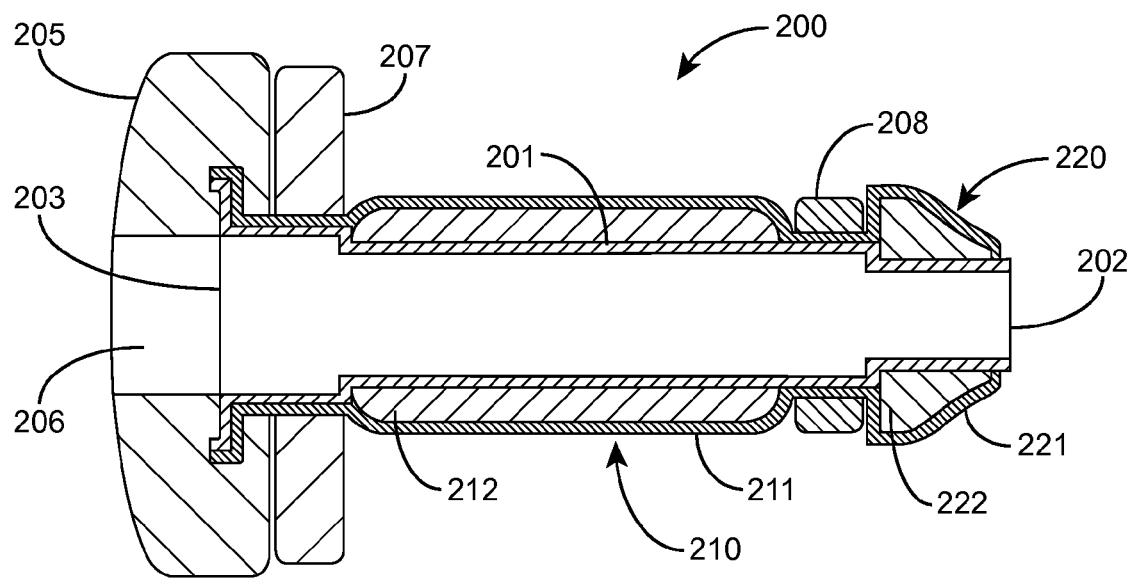
FIG. 5 is a sectional view of an embodiment of an osmotically driven device for dilating a paranasal sinus opening, in a non-expanded configuration, according to embodiments of the present disclosure.
Figure 6:
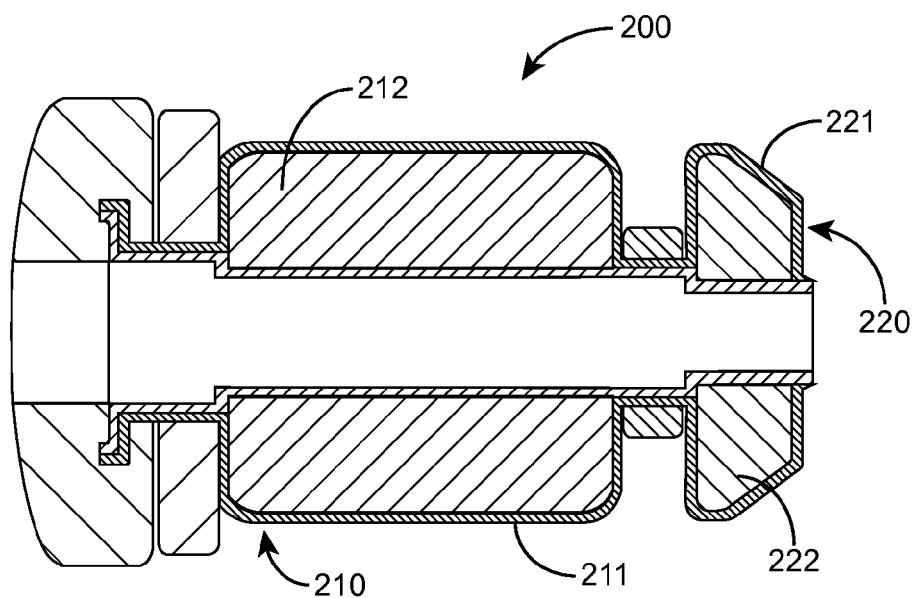
FIG. 6 is a sectional view of the device shown in FIG. 5, in an expanded configuration, according to embodiments of the present disclosure.

Reference is now made to FIGS. 5 and 6 which show an embodiment of an insertable/implantable dilation device 200. Similar to device 100, device 200 has a conduit 201 with a distal opening 202 and a proximal opening 203; a proximal anchor 205 with a central passageway 206; an osmotic driver 210 including a semipermeable membrane 211 surrounding an osmotic core 212; and optional drug releasing reservoirs 207 and 208. Similar to device 100, device 200 has an osmotic core 212 that in certain embodiments gradually increases in volume over a period of 0.5 hours or more, and in other embodiments increases in volume over a period of 4 hours or more, to apply dilating force on the stenotic sinus opening, as shown in FIG. 6.

In place of the distal anchor 104 in device 100, device 200 has an osmotic anchor 220 including an elastic semipermeable membrane 221 surrounding an osmotic core 222. The operation of the osmotic anchor 220 is similar to the operation of osmotic driver 210 in that osmotic core 222 may be configured to expand upon absorption of water from the patient's body. In certain embodiments, osmotic core 222 expands in volume at a rate greater than the rate of expansion of osmotic core 212. For example, osmotic core 222 may become fully expanded within several hours of insertion into the paranasal sinus opening, such as within 1 hour of insertion into the paranasal sinus opening. Driver 220 is shown in a fully expanded configuration in FIG. 6.

Referring now to FIG. 7, there is shown an embodiment of an implantable dilation device 300 that has a curved axis, which assists in the placement into certain sinus openings such as the maxillary sinus opening. Device 300 has multiple osmotic drivers 310a and 310b separated by a channel 309. Each osmotic driver 310a and 310b includes an elastic semipermeable membrane 311a and 311b, respectively, and an osmotic core 312 (the osmotic core is shown in FIG. 8 but not in FIG. 7). Similar to the function and operation of device 100, device 300 also has a proximal anchor 305 at its proximal end, a distal anchor 304 at its distal end; and optional drug releasing reservoirs 307 and 308.

Figure 9:
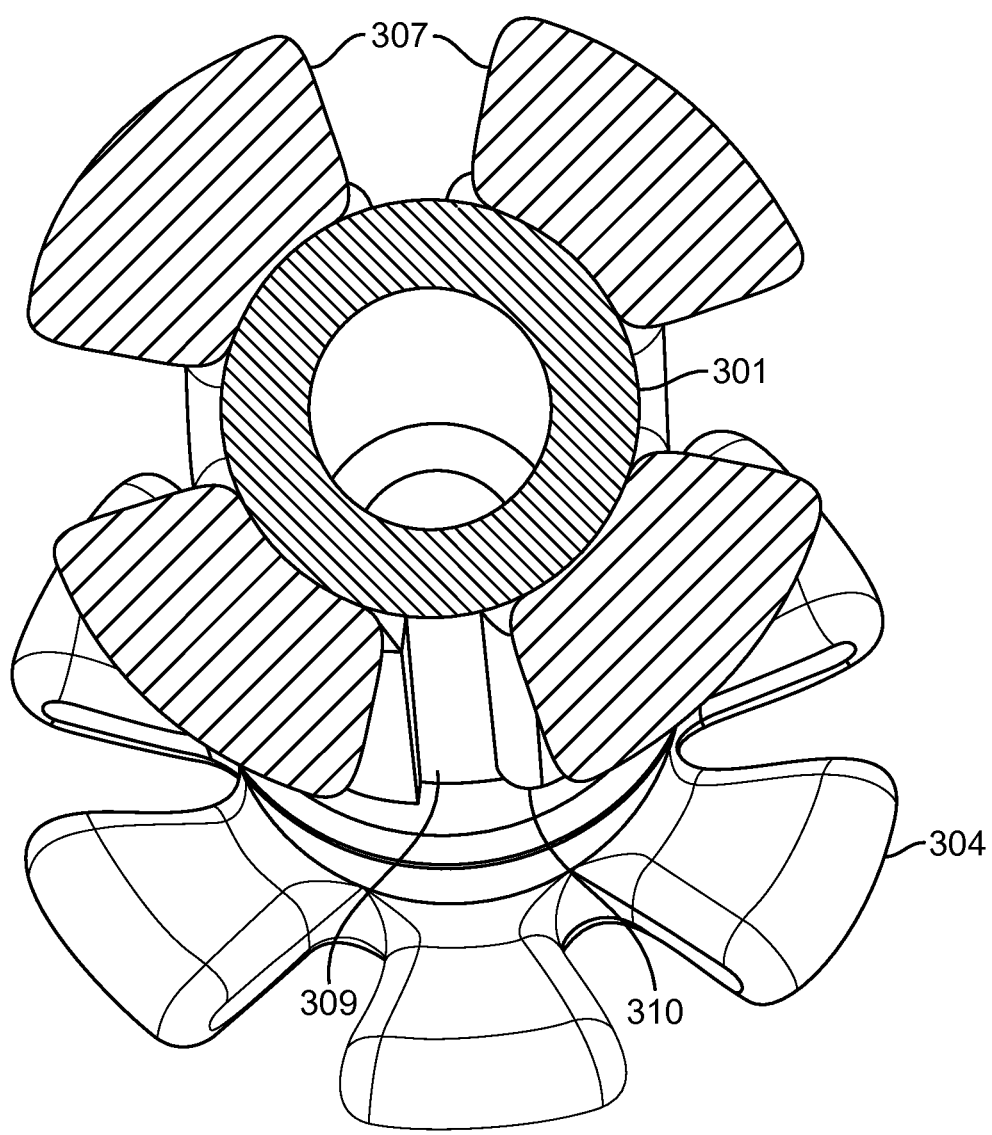
FIG. 9 is a sectional view of the device shown in FIG. 7, taken along line IX-IX, according to embodiments of the present disclosure.
Figure 10:
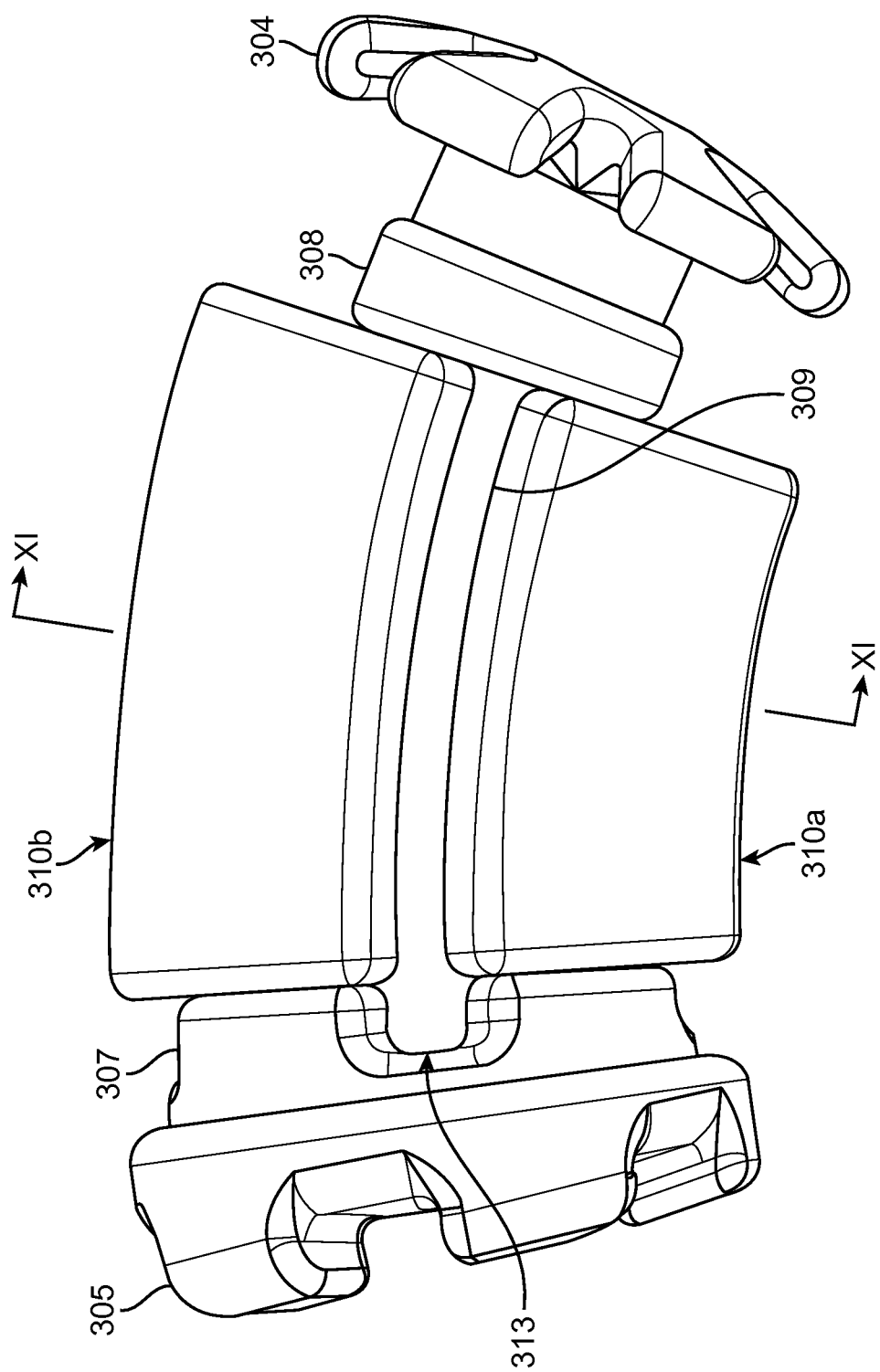
FIG. 10 is a side perspective view of the device shown in FIG. 7, in an expanded configuration, according to embodiments of the present disclosure.
Figure 11:
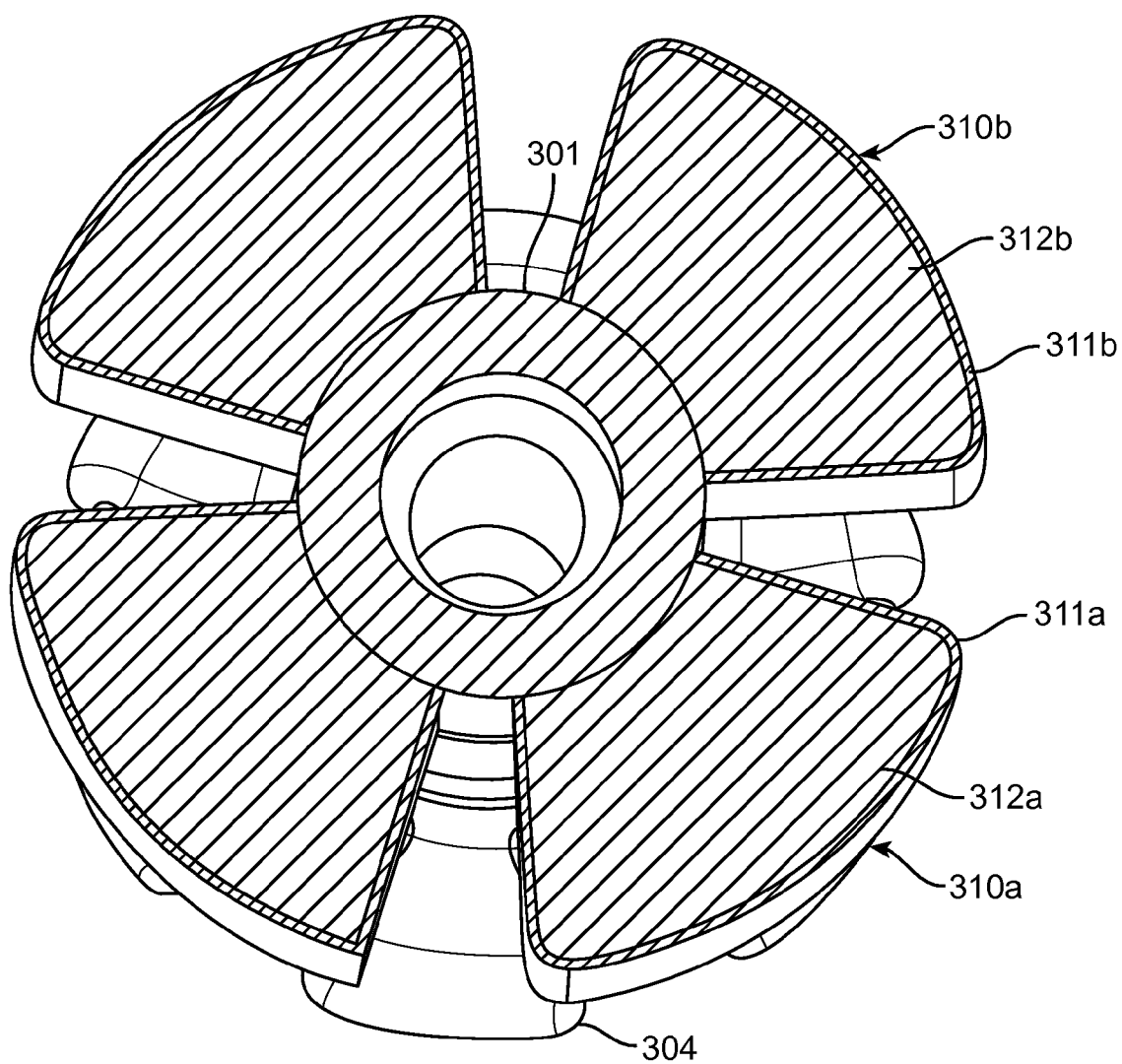
FIG. 11 is a sectional view of the device shown in FIG. 10, taken along line XI-XI, according to embodiments of the present disclosure.

FIGS. 7 to 9 show the device 300 with the osmotic drivers 310*a* and 310*b* in a non-expanded configuration while FIGS. 10 to 11 show the device 300 with the osmotic drivers 310*a* and 310*b* in an expanded configuration. As can be seen from FIGS. 7 to 11, the channels 309 provide a conduit for allowing fluid to drain out of the sinus cavity and air to move in and out of the sinus cavity while the device 300 is implanted in a sinus opening.

Figure 13:
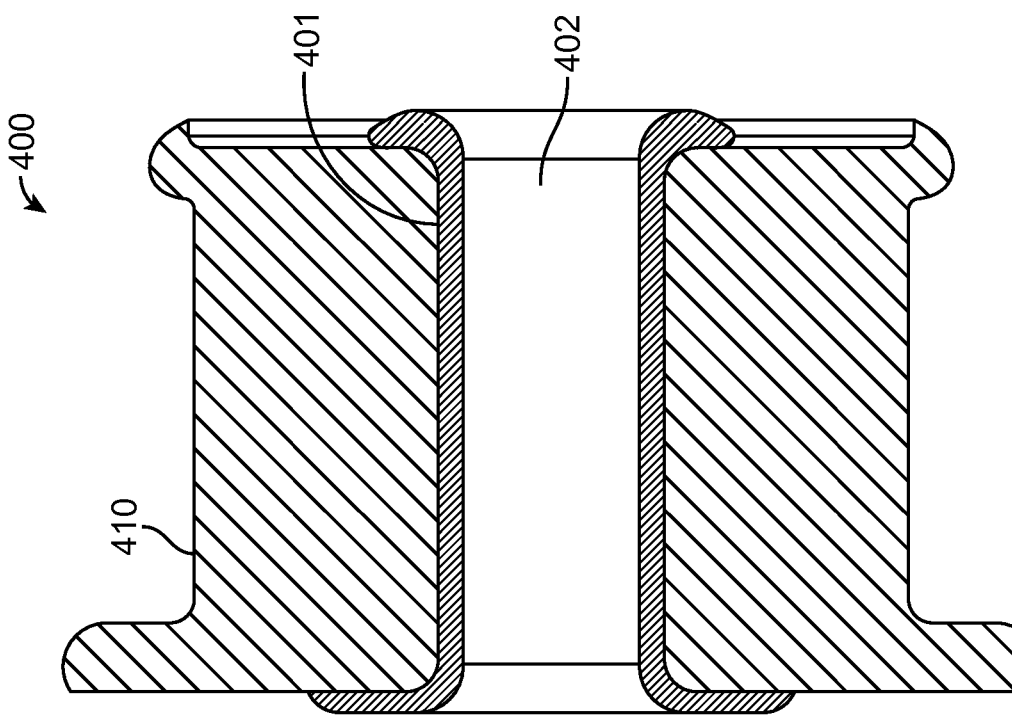
FIG. 13 is a sectional view of the device shown in FIG. 12, in an expanded configuration, according to embodiments of the present disclosure.
Figure 12:
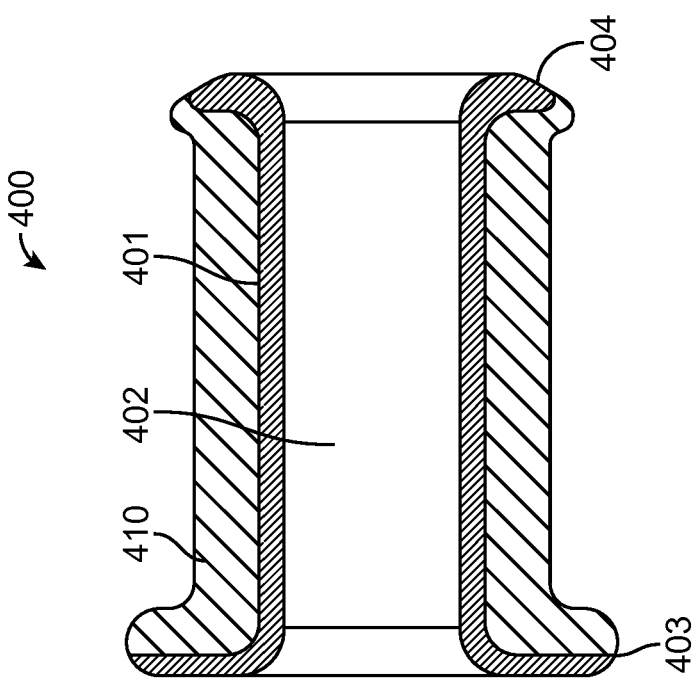
FIG. 12 is a sectional view of an expandable polymer driven device for dilating a paranasal sinus opening, in a non-expanded configuration, according to embodiments of the present disclosure.

Referring now to FIGS. 12 and 13, there is shown an embodiment of an implantable dilation device 400 with an expandable driver including a polymer matrix. Similar to devices 100, 200 and 300, device 400 also has an inner conduit 401 composed of a substantially rigid or non-collapsible polymer or metal. The interior of conduit 401 is open, creating a passageway 402 for allowing bodily fluids such as mucus, puss and blood to drain out of the sinus and air to pass into and out of the sinus cavity while the dilation device 400 is positioned within the sinus opening. The ends of conduit 401 are flared, creating anchoring flanges 403 and 404 which help keep device 400 anchored within the sinus opening during use.

Surrounding conduit 401 is an expandable driver 410 that includes an expandable polymer matrix. Suitable expandable polymers for use as the driver 410 include water swellable polymers such as poly ethylene oxide (PEO), hydroxypropylmethyl cellulose, polyvinyl alcohol, carboxymethylcellulose, sodium carboxymethylcellulose, poloxamer, polyethylene glycol, carbomer, methylcellulose, gelatin, xanthan gum, guar gum and amylose starches. In some cases, the polymer is a hydrophilic polymer that is capable of absorbing 100% or more, such as 200% or more, including 500% or more, or 1,000% or more, or 1,500% or more, for instance 2,000% or more of its dry weight in water. In certain embodiments, the polymer absorbs water and swells in volume in an isotropic fashion, although non-isotropic expansions are possible and may be used in certain embodiments. One example of a hydrophilic polymer is aliphatic, polyether-based thermo-plastic urethane (TPU). This material is an injection moldable thermo-plastic, and may be molded in various shapes, as desired.

In use, the device 400 is positioned within a sinus opening in a non-expanded configuration. Water from the patient's body is absorbed into the polymer matrix of driver 410, causing it to gradually expand to the configuration shown in FIG. 13.

Conduit 401 may be made from a metal, a metallic alloy, a polymer, a ceramic or other rigid or non-collapsible material and may be configured to constrain the expansion of driver 410 in a direction that is parallel to the axis of device 400, ensuring that driver 410 expands in an outward radial direction. For example, the ends of conduit 401 may be flared, creating flanges 403 and 404, which help direct expansion of the driver 410 in an outward radial direction from the conduit 401. Conduit 401 may be rigid or non-collapsible, such that conduit 401 reinforces the inner diameter of the device so that the device is capable of exerting force radially outward without collapsing.

Device 400 may be fabricated by an insert molding operation wherein the expandable polymer is molded onto the rigid or non-collapsible conduit 401. Additionally, device 400 may be fabricated as two separate parts and joined in a mechanical assembly process to form the final as-assembled configuration.

Figure 15:
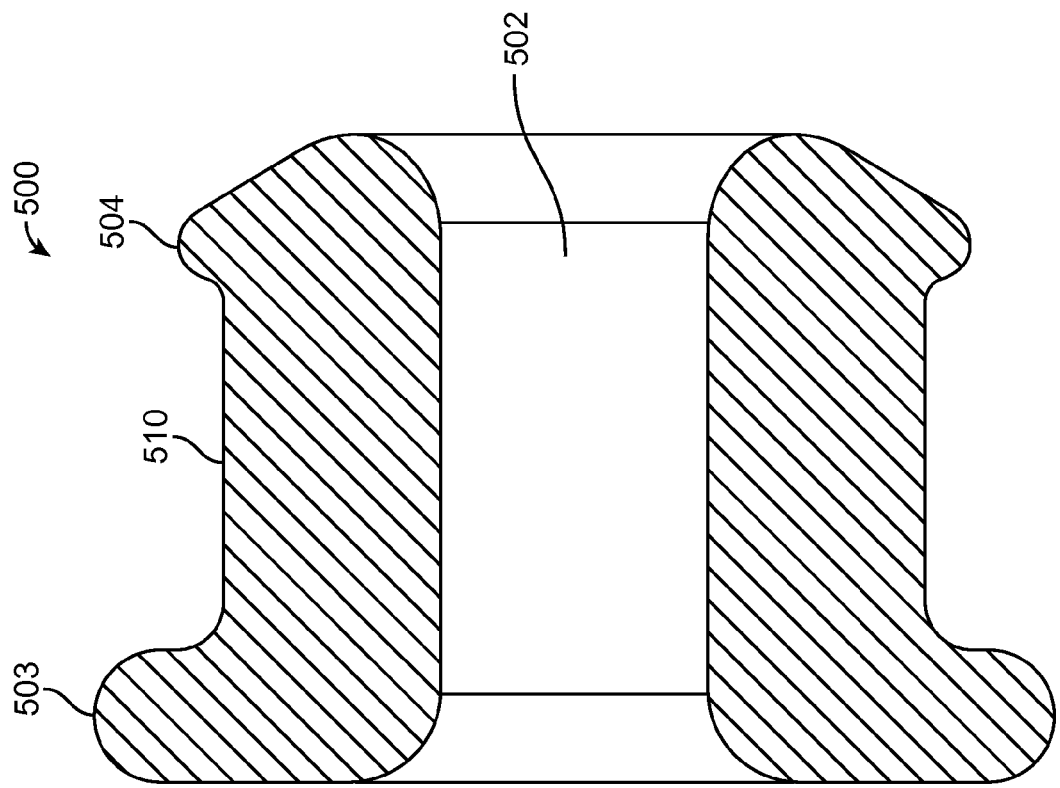
FIG. 15 is a sectional view of the device shown in FIG. 14, in an expanded configuration, according to embodiments of the present disclosure.
Figure 14:
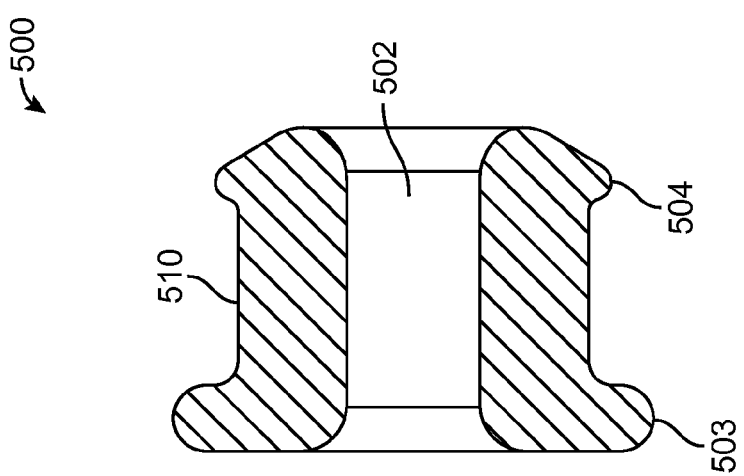
FIG. 14 is a sectional view of an embodiment of an expandable polymer driven device for dilating a paranasal sinus opening, in a non-expanded configuration, according to embodiments of the present disclosure.

Referring now to FIGS. 14 and 15, there is shown an embodiment of an insertable/implantable dilation device 500 with an expandable driver including a polymer matrix. The interior of device 500 is open, creating an inner conduit 502 for allowing bodily fluids such as mucus, puss and blood to drain out of the sinus and air to pass into and out of the sinus cavity while the dilation device 500 is positioned within the sinus opening.

In certain embodiments, the entire device 500 is composed of an expandable polymer matrix 510. The ends of matrix 510 are flared, creating anchoring flanges 503 and 504 which help keep device 500 anchored within the sinus opening during use. A suitable expandable polymer for use as matrix 510 is aliphatic, polyether-based thermo-plastic urethane (TPU). In certain embodiments, the polymer expands by 100% or more in each linear dimension. The linear expansion may be equivalent to a 700% or more volume expansion. In some instances, the polymer has a specific gravity of between 1.10 and 1.15, which equates to a water absorption of approximately 620% by mass. The matrix material may be an injection moldable thermo-plastic, and may be molded in various shapes, as desired. In some instances, the polymer matrix 510 is a homogeneous polymer matrix. In other cases, the polymer matrix 510 is a heterogeneous polymer matrix. For example, the heterogeneous polymer matrix may be configured to have a region of higher rigidity near the interior surface of the device that forms the inner conduit 502. The polymer matrix may also be configured to have regions of higher rigidity at the distal end and the proximal end of the device, such as at the anchoring flanges 503 and 504, respectively. The regions of higher rigidity may facilitate directing the expansion of the polymer matrix radially outward from the inner conduit 502.

In use, the device 500 is positioned within a sinus opening in a non-expanded configuration. Water from the surrounding tissues of the patient's body is absorbed into the polymer matrix, causing it to gradually expand to the configuration shown in FIG. 15.

In general, hydrophilic polymeric materials may be manufactured into the configurations shown in FIGS. 12 to 15 by means of injection molding, extrusion, pultrusion, casting, dip coating, spray coating, machining, stereo lithography, selective laser sintering, or any other method suitable for producing the desired geometries.

Figure 16:
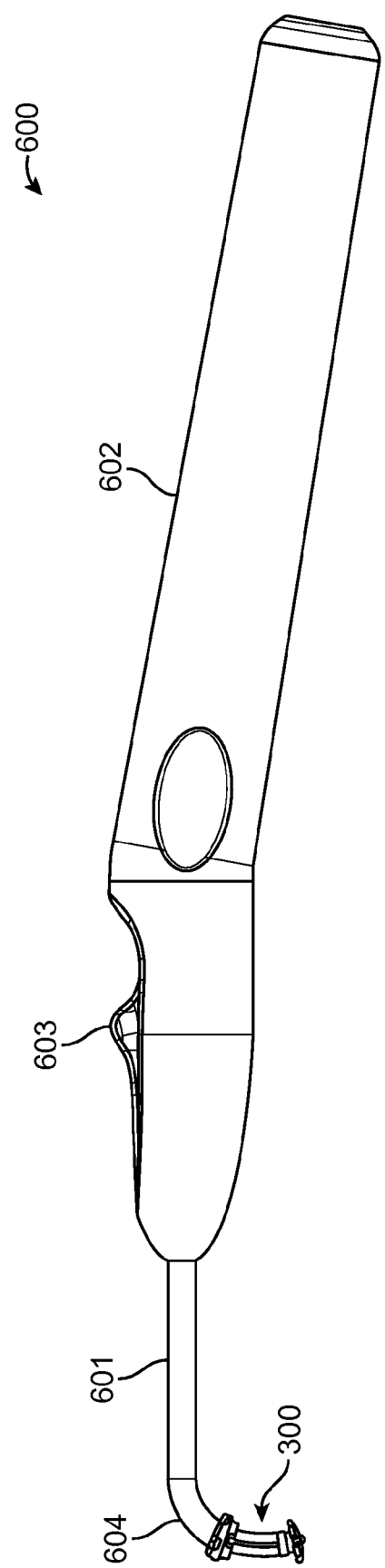
FIG. 16 is a side perspective view of a device for inserting an expandable device into a paranasal sinus opening, according to embodiments of the present disclosure.

Referring now to FIG. 16, there is shown an embodiment of an insertion/implantation device 600 used to place a dilation device 300 within a paranasal sinus opening. The device 600 has a handheld member 602 sized to be gripped by a physician's hand with trigger 603 adapted to be actuated by the physician's thumb. Extending from the device 600 is a hollow elongated member (e.g., a cannula) 601 having a curved tip section 604. For example, the dimensions and tip curvature of the hollow elongated member 601 shown in FIG. 16 are suited for inserting/implanting the dilation device 300 into a paranasal sinus opening. Other configurations of the device 600 are also possible, which may facilitate insertion/implantation of the dilation device 300 into a paranasal sinus, such as frontal sinus, a sphenoid sinus or a maxillary sinus. In certain embodiments, the hollow elongated member 601 has a length ranging from 1 cm to 25 cm, such as 2 cm to 25 cm, including 5 cm to 10 cm and a diameter ranging from 1 mm to 10 mm, such as 1 mm to 8 mm, including 2 mm to 6 mm. In some instances, to facilitate access to an opening of a maxillary sinus, the tip section 604 is configured to bend at an angle ranging from 0° to 90°, such as 10° to 60°, including 20° to 50° from the axis of the non-curved portion of hollow elongated member 601, and the length of the curved tip section is 5 cm or less, such as 3 cm or less, including 2 cm or less. In some cases, to facilitate access to an opening of a frontal sinus, the curved tip section 604 is configured to bend at an angle ranging from 30° to 120°, such as 60° to 100°, including 70° to 95° from the axis of the non-curved portion of hollow elongated member 601, and the length of the curved tip section is 5 cm or less, such as 3 cm or less, including 2 cm or less. In certain embodiments, to facilitate access to an opening of a sphenoid sinus, the curved tip section 604 is configured to bend at an angle ranging from 0° to 90°, such as 0° to 60°, including 0° to 25° from the axis of the non-curved portion of hollow elongated member 601, and the length of the curved tip section is 5 cm or less, such as 4 cm or less, including 2.5 cm or less.

Figure 17:
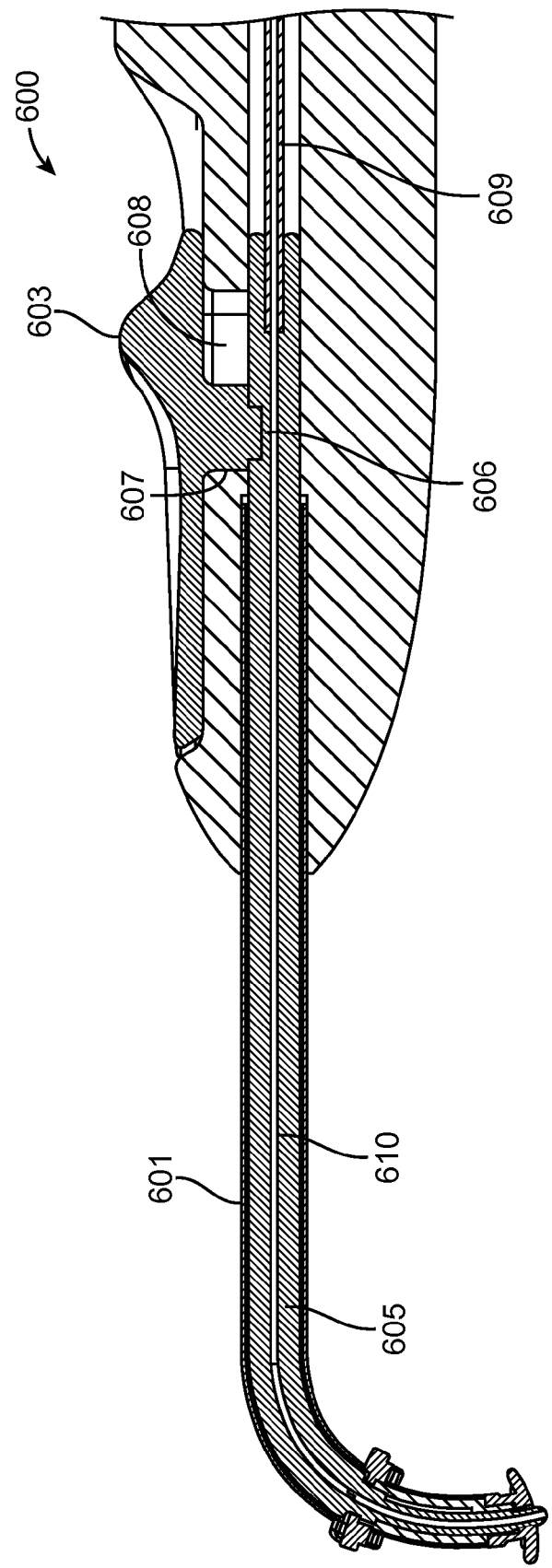
FIG. 17 is a cross sectional view of a portion of the device shown in FIG. 16, according to embodiments of the present disclosure.
Figure 18:
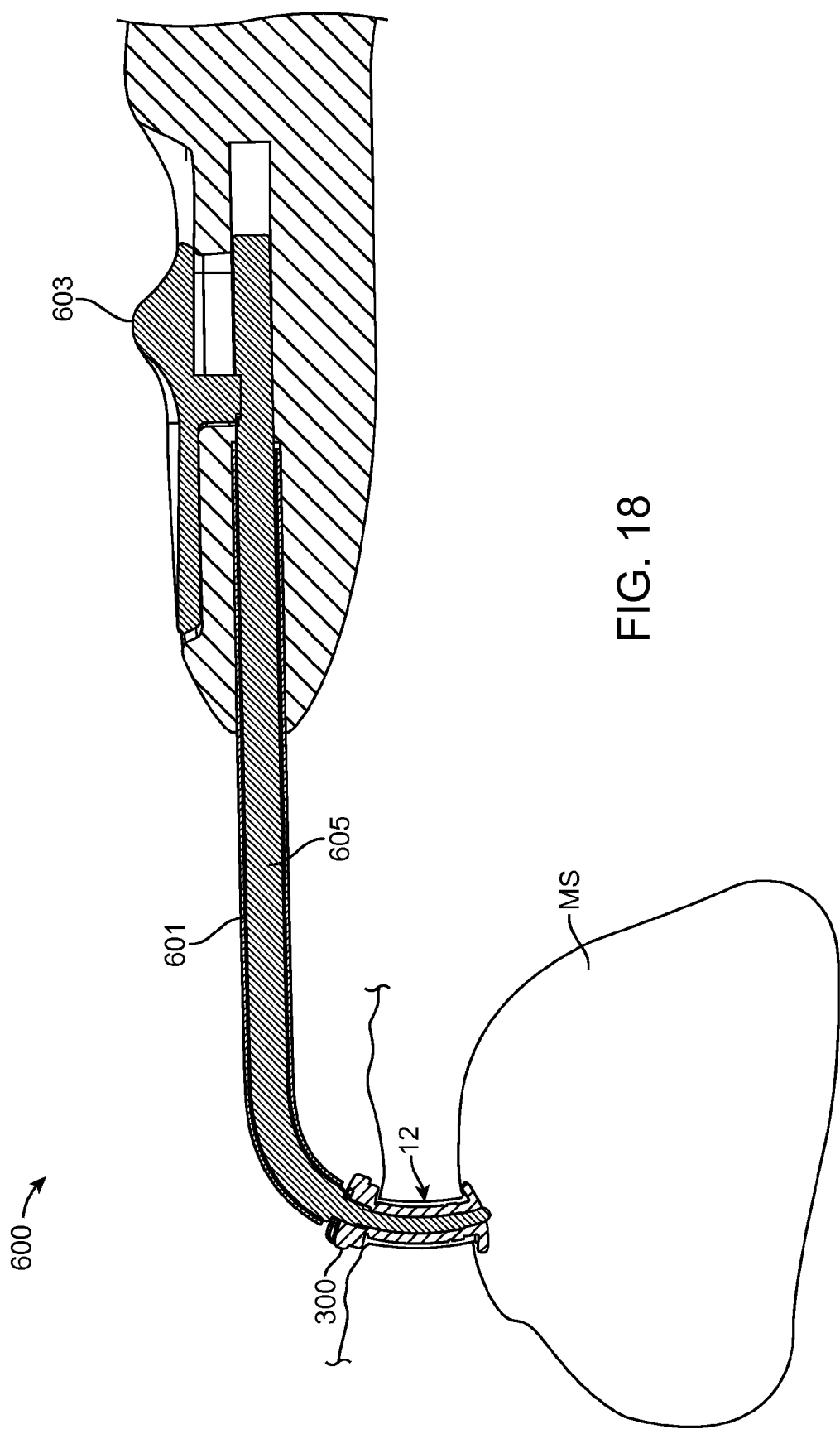
FIG. 18 is a cross sectional view of the device shown in FIGS. 16 and 17 in relation to a maxillary sinus opening, according to embodiments of the present disclosure.
Figure 19:
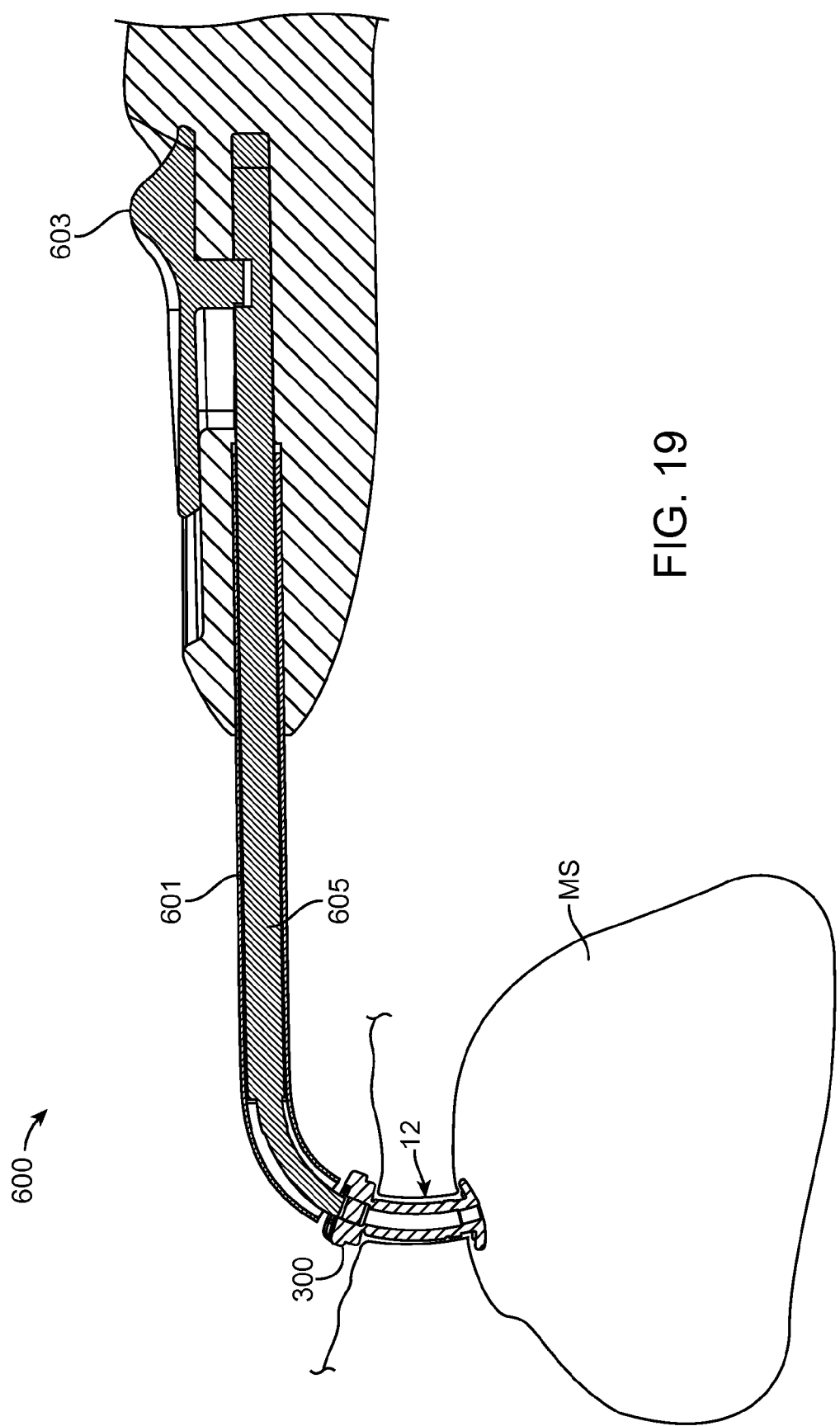
FIG. 19 is a cross sectional view of the device shown in FIG. 16 immediately after the dilation device has been inserted into the paranasal sinus opening, according to embodiments of the present disclosure.

As shown in FIG. 17, slidably positioned within hollow elongated member 601 is an interior elongated member 605 (e.g., a flexible rod). Interior elongated member 605 optionally has a lumen 610. In some instances, lumen 610 is in fluid communication with hollow tube 609. Tube 609 can be connected to a source of fluid (e.g., water, saline, drug solution, combinations thereof, and the like) or a solid pellet dispenser, which can be injected into the sinus cavity and/or nasal cavity before, during or after placement of the dilation device 300 in the stenotic opening. Alternatively, tube 609 can be connected to a vacuum source in order to provide suctioning. In certain embodiments, interior elongated member 605 has a notch 606 which engages trigger arm 607. Trigger arm 607 moves within slot 608. Trigger 603 is biased (e.g., using a spring or other biasing means) toward the position shown in FIG. 17 with the end of interior elongated member 605 extending out from the end of curved tip section 604. When in this position, the dilation device 300 may be slid onto the tip of interior elongated member 605, as shown in FIG. 17. In this configuration, the implantation device 600 is ready for positioning and implanting the dilation device 300. As shown in FIG. 18, the physician then introduces the hollow elongated member 601 through the patient's nostril to reach the occluded opening 12 of a sinus, such as a maxillary sinus (MS). Once the dilation device 300 is positioned within the opening 12, the trigger 603 is activated, releasing the dilation device 300. This occurs by means of sliding the trigger 603 in a proximal direction to the position shown in FIG. 18, which causes the interior elongated member 605 to withdraw out of the dilation device 300, as shown in FIG. 19. Thereafter, the physician may withdraw the hollow elongated member 601 back out of the nostril.

While FIGS. 16 through 19 show device 600 with a dilation device 300 mounted thereon. Embodiments of device 600 can be similarly used to insert/implant other dilation devices, such as, but not limited to, dilation devices 100, 200, 400, 500, 700 and 800 disclosed herein.

Figure 37:
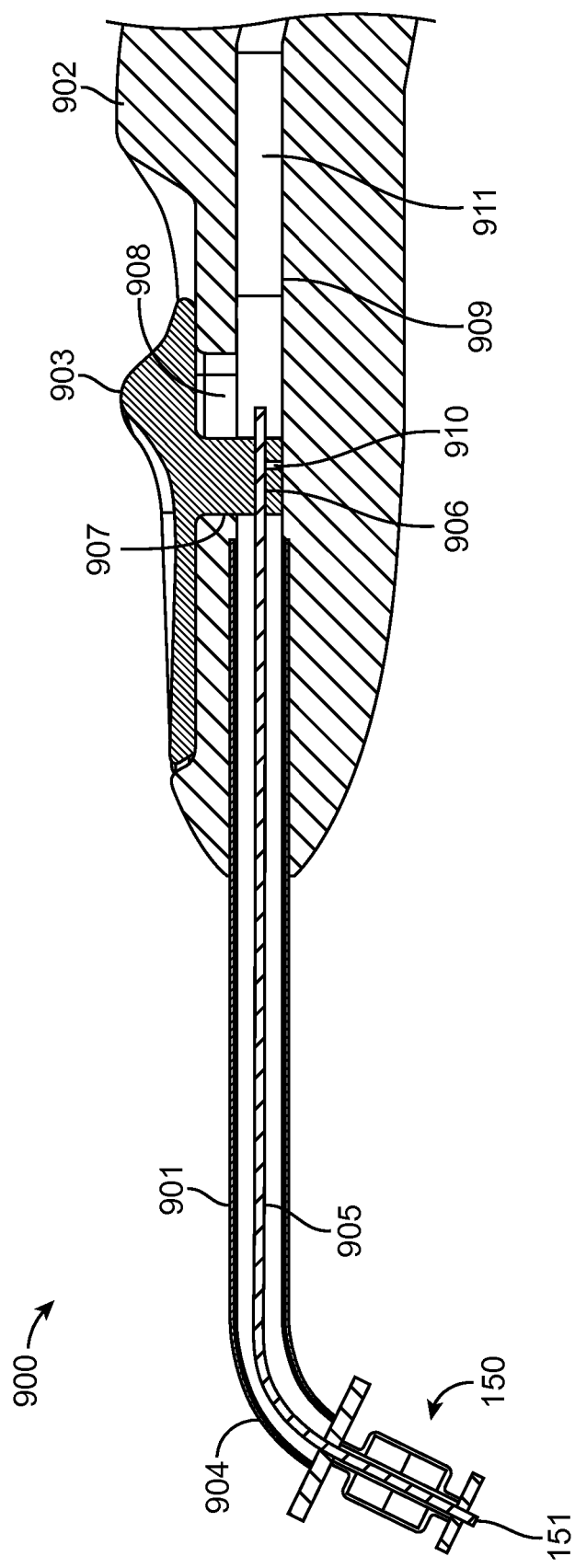
FIG. 37 is a cross sectional view of a device for inserting an expandable device into a paranasal sinus opening, according to embodiments of the present disclosure.

Another embodiment of an osmotic dilator insertion device 900 is shown in FIG. 37. Similar to device 600 shown in FIGS. 16 to 19, device 900 also has a handle 902 with a hollow internal lumen 909, an elongated hollow member 901 mounted on the handle 902 within lumen 909, the member 901 having a curved distal tip section 904, and a slidable trigger 903 with trigger arm 907 which moves back and forth within slot 908. A wire 905 is slidably positioned within member 901. The wire 905 can be for example made from stainless steel having a diameter of 0.3 mm to 0.6 mm. The wire 905 has a curved distal tip which facilitates advancing and retracting the wire 905 through the curved tip section 904 of hollow elongated member 901. The proximal end of wire 905 is attached to trigger arm 907 by means of the proximal end of the wire 905 extending into passageway 906 and then being secured therein using a set screw 910.

With the trigger 903 in the advanced position (i.e., the left-most position as shown in FIG. 37), the distal end of wire 905 extends out from the distal open end of member 901 and provides a length of wire that is sufficient to mount osmotic dilator 150 thereon. In some instances, the length of wire 905 extending beyond the end of member 901 is such that the wire 905 extends through one third or more of the length of the internal tube 151 of dilator 150. In certain cases, tube 151 has a straight axis and the axis of the distal end of wire 905 is curved, such that sufficient friction is created to keep osmotic dilator 150 securely mounted on the distal end of the wire 905 during placement within a sinus ostium. Alternatively, the wire 905 can extend completely through and beyond the distal end of tube 151 and be used by the surgeon to pierce a small hole through a stenotic ostium prior to dilator 150 insertion. Optionally, the distal end of member 901 can be fitted with a slotted flange (not shown in FIG. 37) that engages the proximal anchor of dilator 150 and keeps the dilator 150 from rotating around wire 905 during insertion of the dilator 150 into a sinus ostium.

In certain embodiments, device 900 includes a light source 911, which in some instances is a directional light source, such as a low energy laser. The light source 911 emits light into the lumen of hollow member 901. When the light source 911 is positioned as shown in FIG. 37, the trigger arm 907 may be off set with respect to the position of light source 911 to allow the light to reach the lumen of member 901, or the arm 907 may be constructed of a light-transmitting material such as clear plastic or glass. In some embodiments, in order to allow the light to "bend" around the curved tip 904, the interior surfaces of member 901 can be highly polished (e.g., in the case of member 901 being made of a metal such as stainless steel) or otherwise provided with a mirrored surface treatment. In certain cases, at least portions of the dilator 150 (e.g., the proximal anchor or expandable membrane) are constructed of light transmitting and/or translucent materials so that the light from the light source 911 causes at least portions of the dilator 150 to become illuminated. The illumination may have sufficient intensity so that the emitted light can be seen through the patient's facial tissue. The position of the illuminated dilator 150 may help the physician to correctly position the dilator in the ostium. As an alternative to the light source 911, the osmotic dilator 150 described herein may be placed using an illuminated guide wire, for example of the type described in Goldfarb et al. (U.S. Pat. No. 7,559,925), that extends through the elongated hollow members 601 and/or 901 and optionally through the internal lumen of the osmotic dilator 150.

Figure 20:
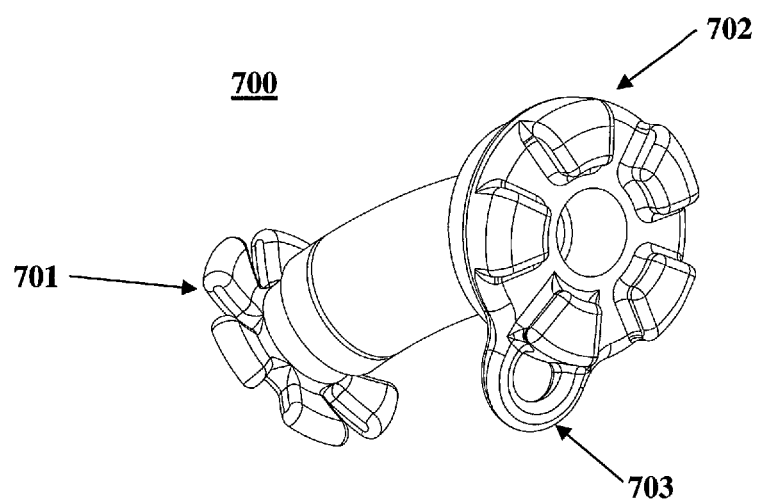
FIG. 20 is a perspective view of a device that includes an attachment portion (e.g., a loop) for facilitating removal of the device from the stenotic opening, according to embodiments of the present disclosure.

As shown in FIG. 20, device 700 is an insertable/implantable dilation device according to embodiments of the present disclosure. Device 700 includes distal anchor 701 at the distal end of the device 700, and proximal anchor 702 at the proximal end of the device 700. In addition, device 700 includes an attachment portion, such as loop 703, configured to facilitate removal of the device from the stenotic opening. As shown in FIG. 20, loop 703 is integrally formed with proximal anchor 702. Other configurations are also possible, such as, but not limited to, an attachment portion that is not integrally formed with proximal anchor 702, but rather attached to proximal anchor 702 by an adhesive, welding, a clip, a snap, and the like. Alternatively, the attachment portion may be formed with or attached to other positions on the device, such as the conduit.

Referring now to the osmotically driven devices 100, 200 and 300, once inserted, the dilation devices 100, 200, and 300 begin to expand by reason of their osmotic drivers 110, 210 and 310, respectively. Referring now specifically to dilation device 100, water from the patient's body begins to permeate through the semipermeable membrane 111 by reason of the osmotically active agents contained within core 112. Similarly, for dilation device 200, water from the patient's body begins to permeate through the semipermeable membrane 211 by reason of the osmotically active agents contained within core 212. Similarly, for dilation device 300, water from the patient's body begins to permeate through the semipermeable membranes 311a and 311b by reason of the osmotically active agents contained within core 312 (e.g., cores 312a and 312b).

Figure 21:
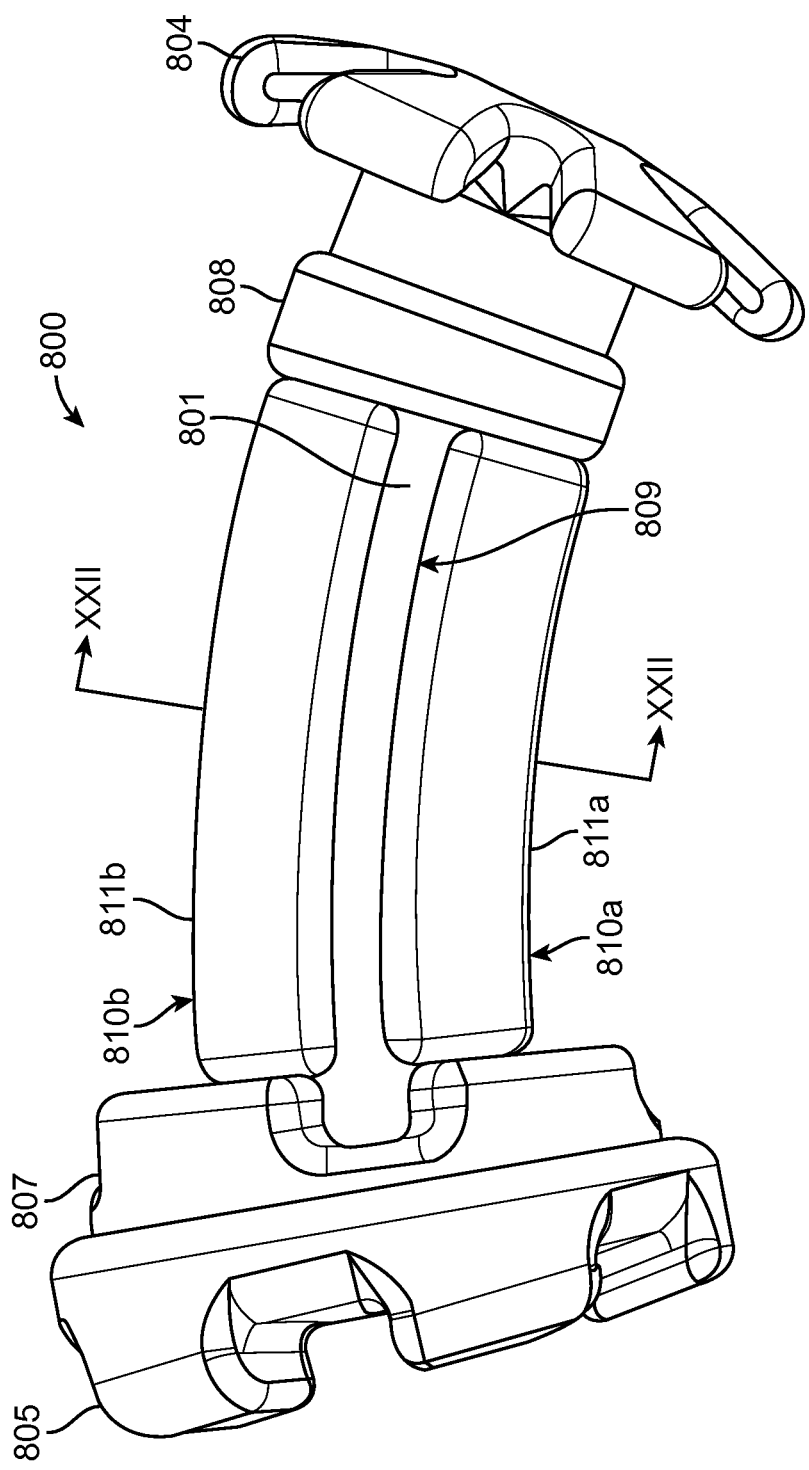
FIG. 21 is a side perspective view of an embodiment of an osmotically driven device for dilating a paranasal sinus opening, in a non-expanded configuration, according to embodiments of the present disclosure.
Figure 22:
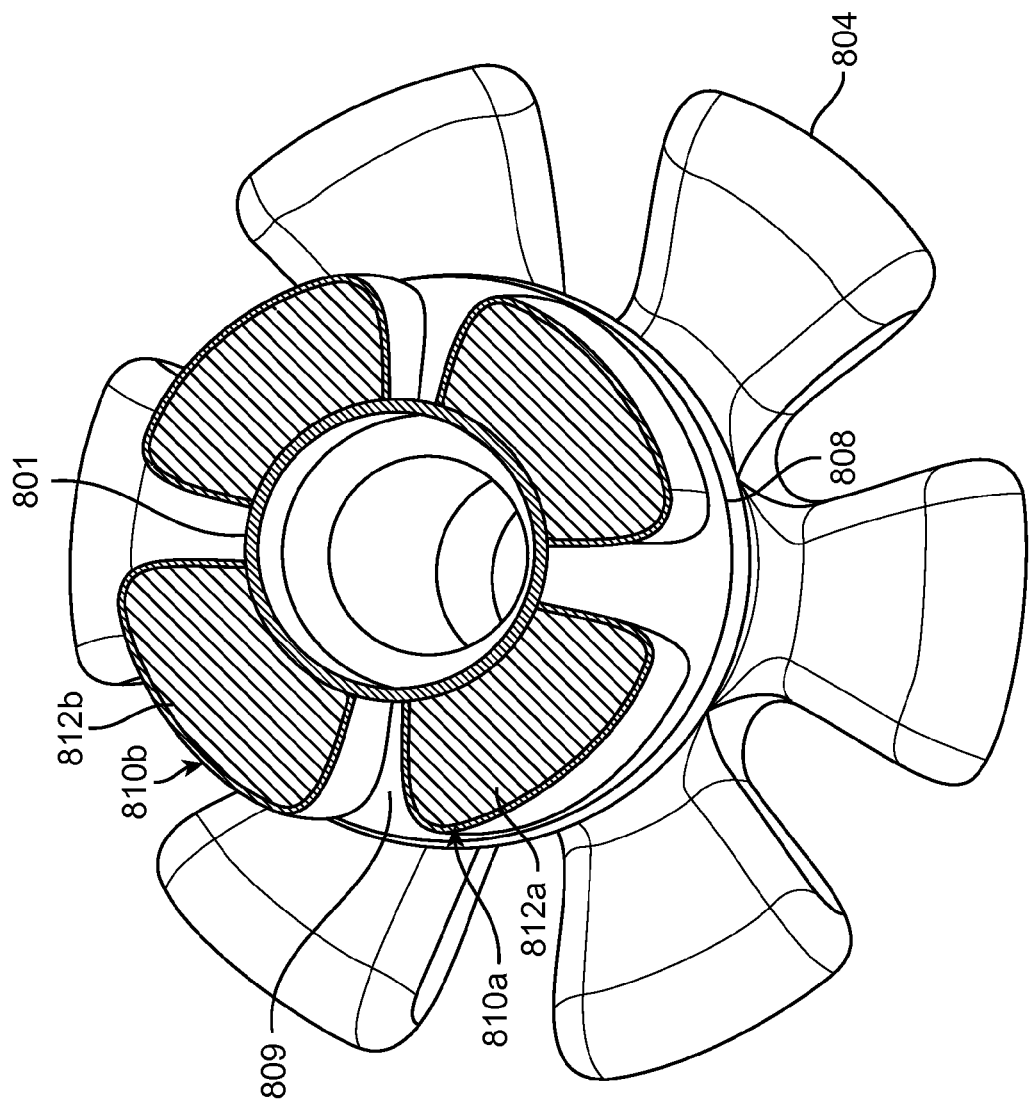
FIG. 22 is a sectional view of the device shown in FIG. 21, taken along line XXII-XXII, according to embodiments of the present disclosure.

Referring now to FIG. 21, there is shown an embodiment of an insertable/implantable dilation device 800. Device 800, like device 300 shown in FIGS. 7 and 8, also has a proximal anchor 805 at its proximal end, a distal anchor 804 at its distal end, and optional drug releasing reservoirs 807 and 808. Device 800 has osmotic drivers 810a and 810b separated by a channel 809. Each osmotic driver 810a and 810b includes an elastic impermeable membrane 811a and 811b, respectively, and an osmotic core 812a and 812b, respectively, as shown in FIG. 22. The device 800 further includes a central conduit 801 that includes a rigid or non-collapsible semipermeable membrane. During use, water from the patient's body contacts the interior of semipermeable membrane conduit 801 and permeates through the conduit 801 and into the osmotic cores 812a and 812b, causing the osmotic cores to increase in volume. This volume increase causes the impermeable elastic membranes 811a and 811b to expand radially outwardly and exert pressure against the patient's tissues surrounding the stenotic sinus opening. The above has been described in relation to osmotic drivers 810a and 810b, osmotic cores 812a and 812b, and impermeable elastic membranes 811a and 811b, however the above description also applies to the other osmotic drivers, osmotic cores and impermeable elastic membranes depicted in FIGS. 21 and 22.

Figure 23:
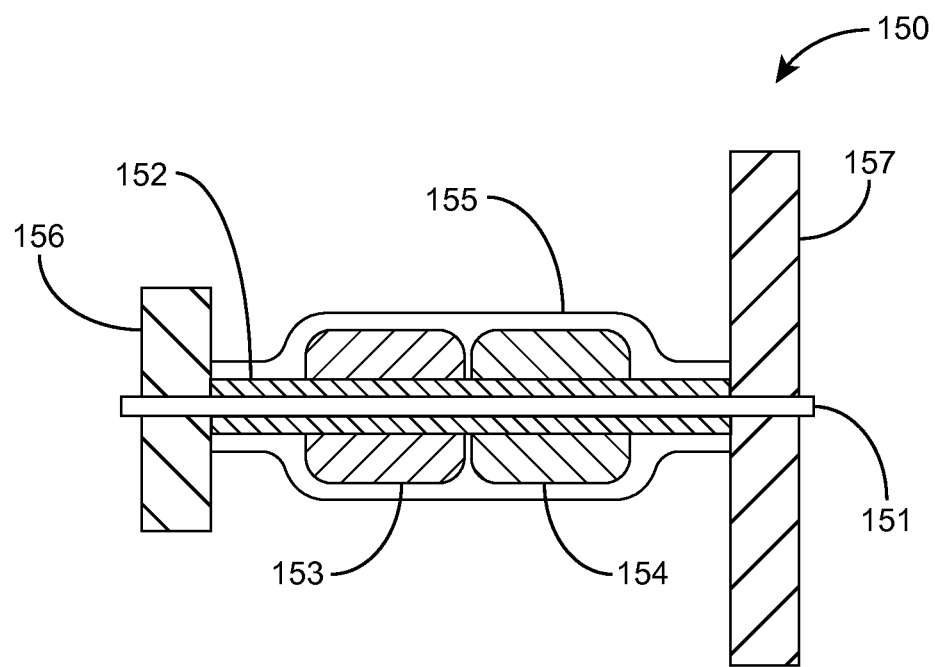
FIG. 23 is a sectional view of an embodiment of an osmotically driven device for dilating a paranasal sinus opening, in a non-expanded configuration, according to embodiments of the present disclosure.
Figure 24:
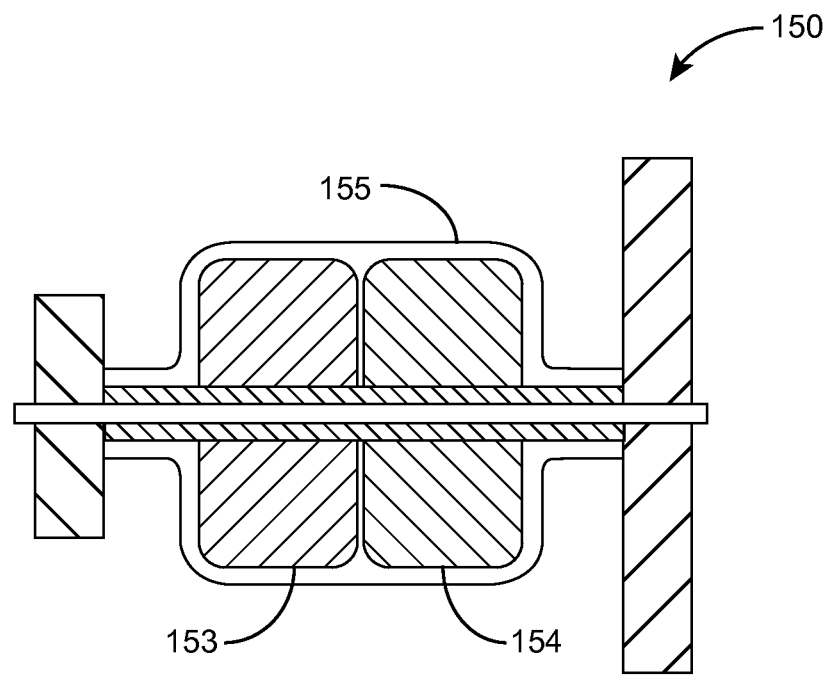
FIG. 24 is a sectional view of the device shown in FIG. 23, in an expanded configuration, according to embodiments of the present disclosure.

Another embodiment of an osmotic dilator 150 is shown in a non-expanded configuration in FIG. 23 and in an expanded configuration in FIG. 24. Dilator 150 includes tube 151 (e.g., a stainless steel tube) having an inner membrane coating 152 disposed thereon. Two osmotic salt tablets 153, 154 are threaded onto the coated tube 151. An external elastic semipermeable membrane coating 155 is applied thereover. The dilator 150 includes distal and proximal anchors 156, 157 respectively, which may be attached (e.g., glued) to the tube 151 to secure the anchors to the tube 151.

As described herein, the distal anchor 156 may be sized such that upon initial insertion the anchor is small enough so that it can be easily pushed through the stenotic ostium during dilator 150 placement and yet expands to a size that keeps the dilator from being pushed out of the ostium and into the nasal passageway during dilator expansion. Two in situ expanding distal anchor designs are illustrated in FIGS. 33 through 36.

Figure 33:
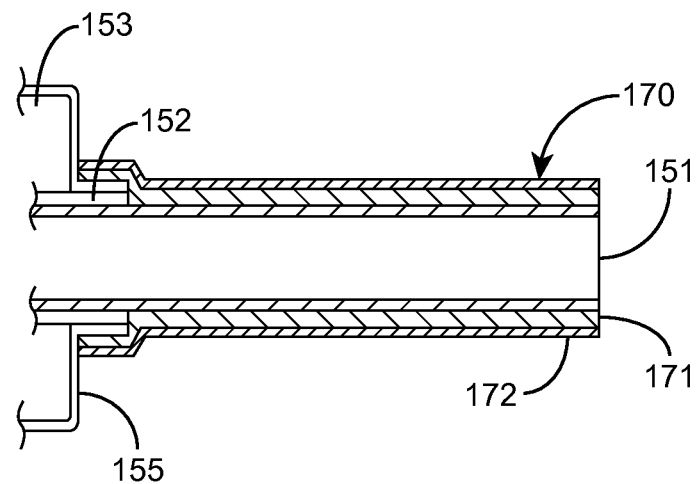
FIG. 33 is a sectional view of an embodiment of an anchor for an osmotically driven device for dilating a paranasal sinus opening, in a non-expanded configuration, according to embodiments of the present disclosure.
Figure 34:
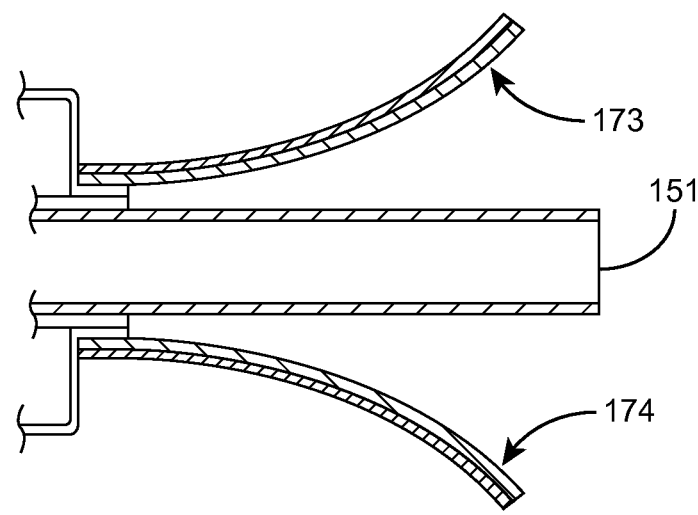
FIG. 34 is a sectional view of the anchor shown in FIG. 33, in an expanded configuration, according to embodiments of the present disclosure.

FIGS. 33 and 34 illustrate a flaring anchor 170 applied to a dilator similar to dilator 150 shown in FIG. 23 and having an inner tube 151 (e.g., a small diameter metal tube) and salt tablet 153 having an inner membrane 152 and an outer elastic semipermeable membrane 155. In certain embodiments, the distance between the edge of salt tablet 153 and the distal end of the tube 151 is 1 mm to 10 mm, such as 3 mm to 8 mm, including 5 mm to 7 mm. For example, the distance between the edge of the salt tablet 153 and the distal end of the tube 151 may be 5 mm to 7 mm. The distal end of tube 151 is first coated with a hydrophilic polymer layer 171 (for example, Tecophilic® 93A-100, Lubrizol Corp., Wickliffe, Ohio). The thickness of the hydrophilic polymer layer may range from 1 mil (0.03 mm) to 30 mil (0.76 mm), such as from 5 mil (0.13 mm) to 25 mil (0.64 mm), including from 10 mil (0.25 mm) to 20 mil (0.51 mm). In some instances, the thickness of the hydrophilic polymer layer is 16 mil (0.41 mm). In certain embodiments, the hydrophilic polymer layer is coated with a hydrophobic polymer layer 172 (for example, Tecophilic® HP60D-20, Lubrizol Corp., Wickliffe, Ohio). The thickness of the hydrophobic polymer layer may range from 1 mil (0.03 mm) to 10 mil (0.25 mm), such as from 1 mil (0.03 mm) to 7 mil (0.18 mm), including from 2 mil (0.05 mm) to 5 mil (0.13 mm). In some instances, the thickness of the hydrophobic polymer layer is 3 mil (0.08 mm). In certain embodiments, the length of tube 151 that is coated is 1 mm or more, such as 3 mm or more, or 5 mm or more. For instance, the length of tube 151 that is coated may be 5 mm. Then 3 to 4 slits, each slit being 1 mm or more in length, such as 2 mm or more, or 3 mm or more (e.g., 4 mm long), are cut through the bilayer coating 171, 172 (e.g., using a razor or laser), the slits running parallel to the axis of the tube, to form sections of the bilayer coating 171, 172. Once placed in the sinus cavity, water from the cavity and surrounding tissues causes the hydrophilic layer 171 to expand to a larger degree than the hydrophobic layer 172, which causes the individual sections 173, 174 of the bilayer coating material to flare out from the tube 151 as shown in FIG. 34, creating an effect similar to the opening of flower petals. Once the sections 173, 174 have flared open, they keep the dilator from being expelled from the ostium and into the nasal passageway during dilator expansion. In some instances, there is little to substantially no adherence between the hydrophilic polymer layer 171 and the stainless steel tube 151. In certain cases, the layer 171 is coated onto a portion of the outer membrane 155, which may be hydrophilic. Alternatively, a cap (not shown in FIGS. 33 and 34 but similar to the cap shown in FIGS. 35 and 36) made from a plastic material (e.g., polyether ether ketone) may be attached (e.g., glued) onto the distal end of the tube 151 to prevent the anchor from sliding off the tube while in situ within the sinus cavity.

In other embodiments, a similar flaring distal anchor may be attached to the dilator 150 with the sections of the anchor arranged in the opposite direction from that shown in FIGS. 33 and 34. In this configuration, the uncut portion of the bilayer coating is anchored at the distal end of tube 151 and the cut portion of the bilayer coating are positioned near the osmotic tablets. When hydrated, this configuration flares out at the opposite end of the anchor from the configuration illustrated in FIG. 34, such that the tips of the anchor sections point towards the tissue surrounding the ostium rather than away from the tissue. Thus, if the dilator is pulled in the direction of the nasal cavity, the anchor sections act like barbs against the tissue surrounding the ostium to retain the dilator in place.

Figure 35:
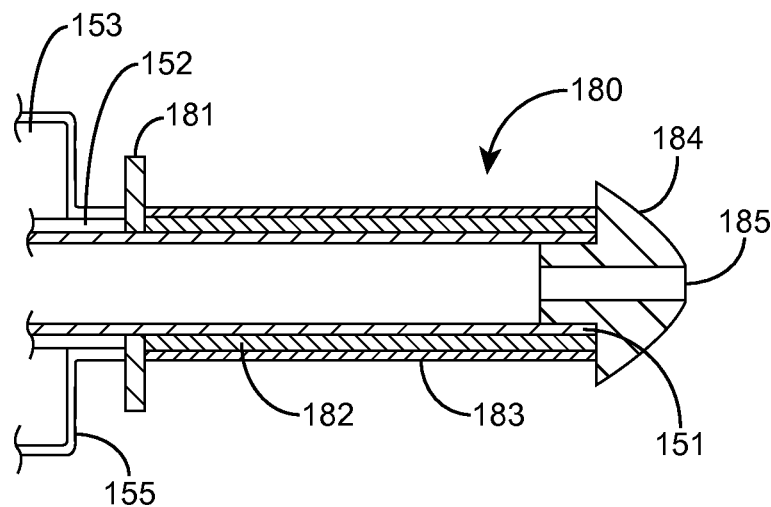
FIG. 35 is a sectional view of an embodiment of an anchor for an osmotically driven device for dilating a paranasal sinus opening, in a non-expanded configuration, according to embodiments of the present disclosure.
Figure 36:
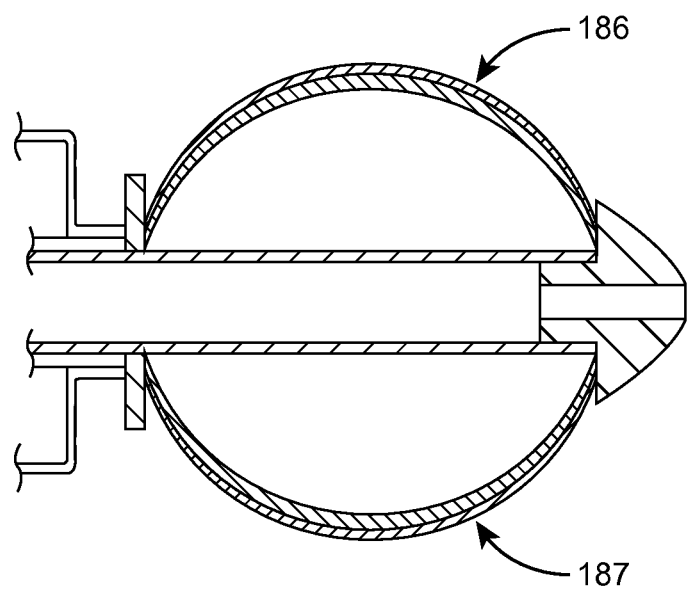
FIG. 36 is a sectional view of the anchor shown in FIG. 35, in an expanded configuration, according to embodiments of the present disclosure.

FIGS. 35 and 36 illustrate an arching anchor 180 applied to a dilator similar to dilator 150 shown in FIG. 23 and having an inner tube 151 (e.g., a small diameter metal tube) and salt tablet 153 having an inner membrane 152 and an outer elastic semipermeable membrane 155. The distance between the edge of salt tablet 153 and the distal end of the tube 151 is 1 mm to 15 mm, such as 3 mm to 12 mm, including 5 mm to 10 mm. For example, the distance between the edge of the salt tablet 153 and the distal end of the tube 151 may be 8 mm to 9 mm. First a washer 181 made from a material such as stainless steel or a polymer such as polyether ether ketone is attached (e.g., glued) onto tube 151, leaving a portion of the tube length (e.g., 7 mm to 8 mm) for applying a bilayer coating. Next, the end of the tube 151 is coated first with a hydrophilic polymer layer 182 (for example, Tecophilic® 93A-100, Lubrizol Corp., Wickliffe, Ohio). The thickness of the hydrophilic polymer layer may range from 1 mil (0.03 mm) to 30 mil (0.76 mm), such as from 5 mil (0.13 mm) to 25 mil (0.64 mm), including from 10 mil (0.25 mm) to 20 mil (0.51 mm). In some instances, the thickness of the hydrophilic polymer layer is 16 mil (0.41 mm). In certain embodiments, the hydrophilic polymer layer is coated with a hydrophobic polymer layer 183 (for example, Tecophilic® HP60D-20, Lubrizol Corp., Wickliffe, Ohio). The thickness of the hydrophobic polymer layer may range from 1 mil (0.03 mm) to 10 mil (0.25 mm), such as from 1 mil (0.03 mm) to 7 mil (0.18 mm), including from 2 mil (0.05 mm) to 5 mil (0.13 mm). In some instances, the thickness of the hydrophobic polymer layer is 3 mil (0.08 mm). Next, a cap 184, optionally provided with a central passageway 185 to allow bodily fluids to drain through the dilator during use, made from a plastic such as polyether ether ketone is attached (e.g., glued) onto the distal end of the tube 151 to prevent the anchor from sliding off the tube while in situ within the sinus cavity. Then 3 to 4 slits, each slit being 5 mm to 6 mm long, are cut through the coating layers 182, 183 (e.g., using a razor or laser), the slits running parallel to the axis of the tube, to form potential arching sections of material. Once placed in the sinus cavity, water from the cavity and surrounding tissues causes the hydrophilic layer 182 to expand to a larger degree than the hydrophobic layer 183, which causes the individual sections 186, 187 to arch out from the tube 151, forming a shape similar to the expanded shape of certain threaded drywall anchors. Once the sections 186, 187 arch out from the tube 151, the arched sections 186, 187 keep the dilator from being expelled from the ostium and into the nasal passageway during dilator expansion. Alternatively, the bilayer coating can be co-extruded first, slit, slipped onto tube 151, and finally anchored in place by gluing cap 184 on the distal end of tube 151.

As a further alternative for anchoring dilator 150, the distal anchor 156 may be eliminated and the thickness of the proximal anchor 157 can be increased over what is shown in FIG. 23 so that the proximal side of anchor 157 is in contact with the wall of the sinus cavity facing the wall having the occluded ostium. In such a configuration, the dilator 150 is wedged into place within the nasal cavity. In certain embodiments, such a design may be used when dilating the maxillary sinus ostium and in those applications where the dilator is in place over a relatively shorter period of time, e.g., less than 1 hour, while the patient remains in the physician's office. In some instances, in such shorter-term dilation applications, the dilator 150, without the distal anchor 156, can be effectively secured within the ostium using a thinner proximal anchor 157, e.g., of the size shown in FIG. 23, by packing cotton or other packing material against the proximal side of the anchor 157 after it is placed in the ostium.

The dimensions, both initial and after dilation, of the osmotic drivers may vary depending on the particular sinus opening to be dilated. In the case of a device for dilating the opening of a maxillary sinus, the initial (e.g., before expansion/dilation) diameter of the osmotic driver may be 5 mm or less, such as 4 mm or less, including 3 mm or less, or 2 mm or less, or 1 mm or less. For example, the initial diameter of the osmotic driver may range from 1 mm to 5 mm, such as 2 mm to 4 mm, including 2 mm to 3 mm. In some cases, the final (e.g., after expansion/dilation) diameter of the osmotic driver is 5 mm or more, such as 6 mm or more, including 7 mm or more, or 8 mm or more, 9 mm or more, or 10 mm or more. For example, the final diameter of the osmotic driver may range from 1 mm to 10 mm, such as 2 mm to 10 mm, including 5 mm to 10 mm. In certain embodiments, the length of the osmotic driver is 20 mm or less, or 15 mm or less, such as 10 mm or less, including 5 mm or less, or 2 mm or less, or 1 mm or less. For instance, the length of the osmotic driver may range from 1 mm to 20 mm, such as 2 mm to 15 mm, including 2 mm to 10 mm.

In the case of a device for dilating the opening of a sphenoid sinus, the initial (e.g., before expansion/dilation) diameter of the osmotic driver may be 5 mm or less, such as 4 mm or less, including 3 mm or less, or 2 mm or less, or 1 mm or less. For example, the initial diameter of the osmotic driver may range from 1 mm to 5 mm, such as 2 mm to 4 mm, including 2 mm to 3 mm. In some cases, the final (e.g., after expansion/dilation) diameter of the osmotic driver is 2 mm or more, such as 3 mm or more, or 5 mm or more, such as 6 mm or more, including 7 mm or more, or 8 mm or more, 9 mm or more, or 10 mm or more. For example, the final diameter of the osmotic driver may range from 1 mm to 10 mm, such as 2 mm to 10 mm, including 3 mm to 5 mm. In certain embodiments, the length of the osmotic driver is 20 mm or less, or 15 mm or less, such as 10 mm or less, including 5 mm or less, or 2 mm or less, or 1 mm or less. For instance, the length of the osmotic driver may range from 1 mm to 20 mm, such as 2 mm to 15 mm, including 2 mm to 10 mm.

In the case of a device for dilating the opening of a frontal sinus, the initial (e.g., before expansion/dilation) diameter of the osmotic driver may be 5 mm or less, such as 4 mm or less, including 3 mm or less, or 2 mm or less, or 1 mm or less. For example, the initial diameter of the osmotic driver may range from 1 mm to 5 mm, such as 2 mm to 4 mm, including 2 mm to 3 mm. In some cases, the final (e.g., after expansion/dilation) diameter of the osmotic driver is 2 mm or more, such as 3 mm or more, or 5 mm or more, such as 6 mm or more, including 7 mm or more, or 8 mm or more, 9 mm or more, or 10 mm or more. For example, the final diameter of the osmotic driver may range from 1 mm to 10 mm, such as 2 mm to 10 mm, including 3 mm to 5 mm. In certain embodiments, the length of the osmotic driver is 30 mm or less, such as 25 mm or less, or 20 mm or less, or 15 mm or less, such as 10 mm or less, including 5 mm or less, or 2 mm or less, or 1 mm or less. For instance, the length of the osmotic driver may range from 1 mm to 30 mm, such as 1 mm to 25 mm, including 2 mm to 25 mm.

For instance, referring back to FIGS. 3 and 4, if conduit 101 has a diameter of 2 mm and the length of the osmotic driver is 10 mm, then the volume of the osmotic core 112 may expand from an initial volume of 0.04 cm$^3$ to a final volume of 0.5 cm$^3$. Accordingly, the semipermeable membrane 111 (assuming the membrane has approximately a cylindrical shape) may be configured to stretch to accommodate the expanding volume of core 112 without breaking. For example, the semipermeable membrane may stretch from an initial surface area of 1 cm$^2$ to 3.5 cm$^2$. As such, in certain embodiments, the area of the membrane may undergo a 4-fold or more increase in surface area without tearing or rupturing. For example, the membrane may be configured to undergo an approximate 2-fold expansion in each of the X and Y directions. In other words, the membrane may have a 200% or more elongation factor before breaking when stretched in any one axis or direction.

As disclosed herein, in certain embodiments, the rate of expansion of the osmotic driver is such that the driver expands over a period of 0.5 hours or more, and in other embodiments over a period of 4 hours or more. Thus, the rate of water imbibition may be such that the dilator expands to the desired size over the desired period of time, e.g., 0.5 hours or more, or 4 hours or more. The rate of volume increase of the osmotic drivers can be approximated by the following equation:

$$dv/dt = A(k)(\Delta\pi)/L$$

where:
k is the osmotic water permeability of the semipermeable membrane;
A is the surface area of the semipermeable membrane;
L is the semipermeable membrane thickness; and
$\Delta\pi$ is the osmotic pressure difference across the membrane.

Using this equation, embodiments of the present disclosure may have a rate of volume increase, for example, according to the following: assuming $k=9.7\times10^{-6}$ $cm^2$/hr atm ($3.8\times10^{-3}$ cm mil/hr atm); $A=0.55$ $cm^2$; $L=0.038$ cm (15 mils); $\Delta\pi=356$ atm (using NaCl as the osmotic core material) gives an osmotic driver volume increase rate of 0.05 $cm^3$/hour. In certain embodiments, the device has a rate of volume increase ranging from 0.01 $cm^3$/hour to 0.5 $cm^3$/hour, such as 0.05 $cm^3$/hour to 0.45 $cm^3$/hour, including 0.1 $cm^3$/hour to 0.4 $cm^3$/hour, or 0.15 $cm^3$/hour to 0.35 $cm^3$/hour, for example 0.2 $cm^3$/hour to 0.3 $cm^3$/hour.

In some instances, the volumetric imbibition rate is gradually decreased by the buildup of hydrostatic pressure within the osmotic driver as the semipermeable membrane stretches and as the membrane exerts pressure against tissues of the ostium. When the hydrostatic pressure in the osmotic driver reaches the osmotic pressure of the osmoagent within the core, the driver reaches equilibrium and substantially stops expanding. In certain embodiments, the osmotic driver is configured such that the driver reaches equilibrium when the device has expanded to its desired size. In some instances, this provides a safety feature for preventing overexpansion of the surrounding tissues of the patient.

In the above equation, $\Delta\pi$ represents the gradient in osmotic pressure across the semipermeable membrane. The osmotic driving force may depend on the osmotic activity of the mucous layer and other fluids surrounding the ostium. For example, the $\pi$ value for normal saline is 8 atm. Therefore, if the osmotic core of the driver contains saturated lactose having a $\pi$ value equal to 18 atm, and assuming the surrounding mucus has similar activity as saline, then $\Delta\pi$ is 10 atm (18 atm–8 atm=10 atm).

Various semipermeable membranes suitable for human use may be included in embodiments of the osmotic dilators. The polymeric materials from which the semipermeable membranes may be made vary based on the pumping rates and device configuration requirements and include, but are not limited to, plasticized cellulosic materials, enhanced polymethylmethacrylate such as hydroxyethylmethacrylate (HEMA) and elastomeric materials such as polyurethanes and polyamides, polyether-polyamide copolymers, thermoplastic copolyesters and the like. Further semipermeable compositions are described in U.S. Pat. Nos. 5,413,572 and 6,270,787, the disclosures of which are incorporated herein by reference in their entirety. In certain embodiments, the semipermeable membrane material includes cellulose acetate CA398 (Eastman Chemical Co., Kingsport, Tenn.).

In certain embodiments, the semipermeable membranes used in embodiments of the present disclosure also include a plasticizer and/or a rubber-like polymer such as a pharmaceutical grade polyacrylate. One suitable polyacrylate is Eudragit NE30D (Evonik Cyro LLC, Piscataway, N.J.). This material is rubbery and has an elongation at break of 600%, meaning it can be stretched about 6-fold before breaking. Eudragit E30D serves as a polymeric plasticizer and mixtures of Eudragit E30D and cellulose acetate CA398 may provide elongation at break (Eb) values that can be tailored to any particular sinus opening, with higher Eb values being associated with blends having a higher fraction of NE30D. Elastomers such as silicones can also be used.

The degree of elastic membrane expansion under pressure may depend on membrane thickness, membrane composition, salt tablet composition and the shape, configuration and number of the salt tablets used. In some instances, the elastic semipermeable membranes exhibit non-uniform expansion. Without being bound to any particular theory, this non-uniformity in membrane expansion may be due to variability in membrane thickness. In other embodiments, the elastic semipermeable membrane expands uniformly. In these embodiments, the elastic semipermeable membrane may have a substantially uniform thickness. When the membranes are applied as multiple coatings of a liquid membrane solution, the membranes may be moved during drying so that thicker coated regions do not develop. For example, an osmotic driver that swells uniformly may include 2 to 4 donut-shaped salt tablets formulated with Polyox™ 303 (Dow Chemical Company, Midland, Mich.) and 50 wt % NaCl, together with an expandable semipermeable membrane composed of Tecophilic® HP93A-100 (Lubrizol Corp., Wickliffe, Ohio) coated to a thickness of 15 mils. These drivers may swell evenly and symmetrically over a period of 4 hours, at which time they reach osmotic equilibrium and substantially stop further swelling, and the symmetry is maintained for 30 hours or more.

As an alternative to a stretchable semipermeable membrane, the membrane may also be composed of a low elongation material that is folded back on itself in the pre-insertion state. For example, the membrane may include materials such as Mylar or polyvinylidene chloride (PVdC). In some cases, the membrane is made to the proper fully expanded size, and then folded upon itself around the osmotic core. In this manner, the membrane unfolds to accommodate the osmotic core as the volume of the osmotic core expands.

Osmotic cores according to embodiments of the present disclosure can include any suitable osmotic agent, examples of which include, but are not limited to, a non-volatile water soluble osmoagent, an osmopolymer which swells on contact with water, or a mixture thereof. Representative osmoagents or osmopolymers are described, for example, in U.S. Pat. Nos. 5,413,572 and 6,270,787, the disclosures of which are incorporated herein by reference in their entirety. Osmotic agents, such as sodium chloride may be used. Sodium chloride in compressed form is an osmotic agent as described, for example, in U.S. Pat. No. 5,728,396, the disclosure of which is incorporated herein by reference in its entirety. The osmotic cores may further include appropriate lubricants, binders, and viscosity modifying agents, such as sodium carboxymethylcellulose or sodium polyacrylate. In certain embodiments, the osmotic agent is capable of generating a pressure ranging from 1 atm to 50 atm, such as 5 atm to 25 atm, including 10 to 20 atm. A summary of suitable osmotic agents (also referred to herein as osmoagents) is listed in Table 1 below. The osmoagents listed in the left column are at saturated concentration in water. The column on the right represents values calculated at one tenth saturated concentration.

TABLE 1

Osmotic Pressures of Various Osmotic Agents

| Saturated Solute | π (atm) | 0.1 Saturated Solute | π (atm) |
|---|---|---|---|
| lactose-fructose | 500 | lactose-fructose | 50 |
| dextrose-fructose | 450 | dextrose-fructose | 45 |
| urea | 445 | urea | 45 |
| sucrose-fructose | 430 | sucrose-fructose | 43 |
| mannitol fructose | 415 | mannitol fructose | 42 |
| sodium chloride | 356 | sodium chloride | 36 |
| fructose | 355 | fructose | 36 |
| sorbitol | 305 | sorbitol | 31 |
| lactose-sucrose | 250 | lactose-sucrose | 25 |
| lactose-dextrose | 225 | lactose-dextrose | 23 |
| mannitol-dextrose | 225 | mannitol-dextrose | 23 |
| dextrose-sucrose | 190 | dextrose-sucrose | 19 |
| mannitol-sucrose | 170 | mannitol-sucrose | 17 |
| sodium citrate | 165 | sodium citrate | 17 |
| sucrose | 150 | sucrose | 15 |
| citric acid | 150 | citric acid | 15 |
| mannitol-lactose | 130 | mannitol-lactose | 13 |
| dextrose | 82 | dextrose | 8 |
| potassium sulfate | 39 | potassium sulfate | 4 |
| mannitol | 38 | mannitol | 4 |
| sodium phosphate tribasic, 12H2O | 36 | sodium phosphate tribasic, 12H2O | 4 |
| sodium phosphate dibasic, 12H2O | 31 | sodium phosphate dibasic, 12H2O | 3 |
| sodium phosphate dibasic, 7H2O | 31 | sodium phosphate dibasic, 7H2O | 3 |
| sodium phosphate dibasic, anhydrous | 29 | sodium phosphate dibasic, anhydrous | 3 |
| lactose | 18 | lactose | 2 |

Ref:
1) values for saturated solutions from U.S. Pat. No. 4,519,801 except lactose.
2) solubility of lactose from J. Machado, et. al, "Solid-liquid equilibrium of a-lactose in ethanol water", *Phase Equilibria* 173 (2000) 121-134. solubility used to calculate osmotic pressure.
3) 0.1 osmotic pressures calculated from van't Hoff law.

The osmotic agent as disclosed in embodiments herein can also be in the form of a polymer. A general description of suitable osmotically active polymers (also referred to herein as osmopolymers) is provided in U.S. Pat. No. 5,160,743, the disclosure of which is incorporated herein by reference in its entirety. Some suitable osmopolymers include, but are not limited to, polyethylene oxide (Polyox® Coagulant Grade, Polyox® 303 low ethylene oxide, Colorcon, Harleysville, Pa.), cellulose gum (Sodium Carboxymethyl Cellulose Grade 7H4F, Aqualon, Wilmington, Del.), and polyacrylic acids (Carbopol Grades 974 NF, EDT2020 NF, Ultrez 10 NF, and ETD 2020NF, Lubrizol Corporation, Wickliffe, Ohio).

In certain embodiments, at least portions of the dilation devices as disclosed herein are formed of bioerodible (also referred to herein as bioabsorbable) materials that are capable of breaking down and either being absorbed by, or expelled by, the patient's body. Such bioerodible or bioabsorbable materials include metals, polymers, and bioactive glasses. Suitable bioerodible/bioabsorbable metals include magnesium alloys, including formulations such as the magnesium alloys disclosed in U.S. Patent Application No. 2002/0004060, the disclosure of which is incorporated herein by reference in its entirety. In some instances, the bioerodible/bioabsorbable alloy includes 50-98% magnesium, 0-40% lithium, 0-5% iron and 5% or less of other metals. Other suitable formulations include a magnesium alloy having 90% or more magnesium, 3.7%-5.5% yttrium, and 1.5%-4.4% rare earths. Additional formulations are disclosed in U.S. Patent Application No. 2004/0098108, the disclosure of which is incorporated herein by reference in its entirety. Suitable bioerodible/bioabsorbable polymers include polyactic acid, polyglycolic acid, collagen, poly-caprolactone, hylauric acid, adhesive protein, co-polymers of these materials, as well as composites and combinations thereof.

In certain embodiments the entire dilation device is formed of bioerodible/bioabsorbable materials. In these embodiments, no active removal of the device is required, e.g., the device is passively removed through the process of bioerosion/bioabsorption. In some instances, only a portion of the device is composed of bioerodible materials. For example, the drug reservoirs may include bioerodible/bioabsorbable material. In these embodiments, drug releasing bioerodible/bioabsorbable polymers can be used, including those disclosed in U.S. Pat. Nos. 5,464,450; 6,387,124; and 5,500,013, the disclosures of which are incorporated herein by reference in their entirety.

Methods

Aspects of the present disclosure include a method of dilating a stenotic opening in a subject. In certain embodiments, the method includes positioning a device for dilating the stenotic opening in the stenotic opening. In some cases, the device includes an osmotic driver configured to expand an expandable portion from a non-expanded configuration to an expanded configuration, and the expandable portion disposed peripherally around the driver and configured to expand from the non-expanded configuration to the expanded configuration, where the non-expanded configuration is sized to be positioned within the stenotic opening.

When a patient's opening to any of the maxillary, frontal or sphenoid sinuses becomes occluded or partially occluded (e.g., stenotic), the sinus is unable to properly drain and ventilate resulting in a tendency to develop infections, e.g., sinusitis. The implantable dilation devices disclosed herein are adapted to be inserted into these occluded or partially occluded sinus openings by way of the nostril opening (NO) and nasal cavity (NC).

Aspects of the present disclosure include a method of dilating a stenotic opening of a paranasal sinus in a subject. In certain embodiments, the method includes positioning a device in the stenotic opening, where the device is a device for dilating the stenotic opening as described herein. As described above, the device is configured to expand from a non-expanded configuration to an expanded configuration, where the expanded configuration dilates the stenotic opening. By "dilate" is meant that the average diameter of the stenotic opening is greater after the device has expanded to its expanded configuration as compared to the average diameter of the stenotic opening before the device has expanded.

In some cases, the method further includes removing the device from the stenotic opening. The device may be removed from the stenotic opening at a point in time after insertion of the device into the stenotic opening. For instance, the device may be removed from the stenotic opening at a point in time after the device has expanded to the expanded configuration. The device may be removed by contacting a removal device to the device and extracting the device from the stenotic opening. In some cases, the removal device may be attached to the device using a hook, a loop, a clamp, a suction device, a tether and the like. For instance, the removal device may include a hook configured to attach to a loop on the device. Removal of the device may be achieved by pulling the device from the stenotic opening. In certain embodiments, removal of the device may be facilitated by reducing the pressure exerted by the driver against the surrounding tissues before removing the device from the stenotic opening. In some cases, the internal pressure of the driver may be reduced by puncturing the driver. For example, the removal device may include a needle or blade configured to create a hole in the driver allowing the internal pressure of the driver to equalize with the pressure in the nasal cavity. In some cases, the removal device may include a suction device configured to remove the internal contents of the driver from the device, thus reducing the pressure the device is exerting on the surrounding stenotic opening.

In certain embodiments, the device can include a bioerodible or bioabsorbable material where the device removal occurs by bioerosion or bioabsorption of the device. The device may be left in the stenotic opening of the subject and the device gradually erodes and may be absorbed by or expelled by the patient's body over a period of time.

Aspects of the present disclosure include inserting the device through a nostril of a patient into a stenotic opening of a frontal sinus, a sphenoid sinus or a maxillary sinus of the patient. After insertion, the device is left in place in the stenotic opening for an extended period of time during which the size of the device slowly expands exerting pressure on the stenotic opening to gradually dilate the opening. In order to minimize patient discomfort, the expansion of the device may occur over a period of 0.5 hour, 1 hour 2 hours, 3 hours or 4 hours or more. In certain embodiments, the device expansion occurs over a period of 4 hours to 14 days and is then removed from the opening. In other embodiments, the device expansion occurs over a period of 1 to 10 days and is then removed from the opening. In still other embodiments, the device expansion occurs over a period of 2 to 8 days and is then removed from the opening. The device can be left in place in the opening for 3 weeks or more before it is removed from the opening.

In certain embodiments, the method includes contacting the device with a fluid prior to positioning the device in the stenotic opening. Contacting the device with a fluid prior to positioning the device in the stenotic opening may initiate expansion of the device prior to insertion of the device in the stenotic opening. For embodiments of the device that include a swellable polymer or an osmotic agent, contacting the device with a fluid prior to insertion into the stenotic opening may facilitate expansion of the device after positioning the device in the stenotic opening. For example, embodiments of the device may be configured to begin expanding 30 min or more, such as 45 min or more, including 60 min or more, or 90 min or more, 120 min or more, or 180 min or more after the device has been contacted with a fluid. In these embodiments, contacting the device with a fluid prior to insertion of the device into the stenotic opening may facilitate the onset of expansion of the device at a point in time sooner after insertion of the device into the stenotic opening. In some instances, the fluid may include water, saline, sterile water, sterile saline, and the like.

In certain embodiments, the method includes delivering a drug from the device while the device is positioned within the stenotic opening. For example, the drug may include, but is not limited to, an antibiotic, an anti-inflammatory drug, anesthetics (e.g., local anesthetics), analgesics (e.g., locally acting analgesics), vasoconstrictors, combinations thereof, and the like, as discussed above. The drug may be delivered to the tissues of the stenotic opening that surround the device when the device is positioned within the stenotic opening. In some cases, the drug may be delivered to the tissues at the interior end of the stenotic opening or into the paranasal sinus. In certain instances, the drug may be delivered to the tissues at the exterior end of the stenotic opening or into the nasal cavity.

Systems

Aspects of the present disclosure include a system for dilating a stenotic opening of a paranasal sinus in a subject. The systems include a device for dilating the stenotic opening and an implantation device configured to position the device in the stenotic opening. The device may include an expandable portion configured to expand from a non-expanded configuration to an expanded configuration, and a driver configured to expand the expandable portion from the non-expanded configuration to the expanded configuration, as described herein.

Suitable implantation devices are described herein and also in U.S. Provisional Application No. 61/378,368, filed on Aug. 30, 2010, U.S. Provisional Application No. 61/416, 240, filed Nov. 22, 2010, and in a U.S. Non-Provisional Application filed concurrently with the present U.S. Application entitled "DEVICES AND METHODS FOR INSERTING A SINUS DILATOR", the disclosures of each of which are hereby incorporated by reference in their entirety.

In certain embodiments, the system includes a device for dilating a stenotic opening of a paranasal sinus and a stent. The stent may be configured such that the device fits within the stent when the device is in a non-expanded configuration, as described herein. For example, the stent may have a cylindrical shape with a diameter that is slightly greater than the diameter of the device when the device is in a non-expanded configuration. In some cases, the stent is an expandable stent. The expandable stent may be configured to expand in size as the device expands from a non-expanded configuration to an expanded configuration. In certain embodiments, the stent is configured to maintain its expanded configuration after it has been expanded from the non-expanded configuration to the expanded configuration. For example, the stent may be configured, such that the stent is able to expand from a non-expanded configuration to an expanded configuration, but upon application of a force to the exterior surface of the stent, may maintain substantially the same interior diameter or deform under application of the force and then return to substantially the same interior diameter after removal of the external force. In some cases, the stent may be configured such that pressure exerted on the exterior surface of the stent by the surrounding tissues during use does not significantly decrease the interior diameter of the stent. In certain embodiments, the stent is configured, such that the interior diameter of the stent does not significantly decrease even if the dilation device is removed. A stent that is configured to maintain its expanded configuration may facilitate dilation of the stenotic opening. The stent may be made of any suitable material know by those of ordinary skill in the art to be useful for a stent, such as a shape-memory alloy, including but not limited to nitinol, stainless steel, titanium, cobalt-chromium alloy, combinations thereof, and the like.

Utility

The subject devices, systems and methods find use in a variety of different applications where the dilation of a stenotic opening of a paranasal sinus in a subject is desired. In certain embodiments, the methods are directed to the treatment of a patient having sinusitis. As described above, the method may include positioning a device in the stenotic opening, where the device is a device for dilating the stenotic opening as described herein. Dilation of the stenotic opening of the paranasal sinus may facilitate an alleviation of the symptoms associated with sinusitis. For instance, dilation of the stenotic opening may allow a greater amount of drainage through the stenotic opening as compared to the undilated stenotic opening. Dilation of the stenotic opening may also facilitate the flow of air into and out of the paranasal sinus, which may help alleviate the symptoms associated with sinusitis.

The subject devices, systems and methods may also facilitate the treatment of a patient having sinusitis by delivering a drug for the treatment of sinusitis from the device while the device is positioned within the stenotic opening. As described herein, the device may include drug reservoirs and may be configured to deliver the drug to the tissues near the stenotic opening and/or the tissues surrounding the stenotic opening, including, but not limited to, the interior tissues of the stenotic opening, the interior lumen of the paranasal sinus, the tissues of the stenotic opening, the exterior tissues of the stenotic opening, and the nasal cavity. Delivery of a drug for the treatment of sinusitis from the device may facilitate the alleviation of symptoms associated with sinusitis.

Kits

Aspects of the present disclosure additionally include kits that have a device for dilating a stenotic opening of a paranasal sinus in a subject, as described in detail herein. The kits may include one or more devices, where the devices may be provided in a variety of different sizes. The size of the device may depend on the type of paranasal sinus to be treated (e.g., a frontal sinus, a sphenoid sinus or a maxillary sinus), the physiology of the subject to be treated, the severity of stenosis, etc. Additional embodiments of the kits may include a drug, such as, but not limited to an antibiotic, an anti-inflammatory drug, anesthetics (e.g., local anesthetics), analgesics (e.g., locally acting analgesics), vasoconstrictors, combinations thereof, and the like. The drug may be provided in a separate container, such as a syringe, vial, bottle, etc., such that the drug may be filled into the drug reservoir of the device prior to insertion of the device into the stenotic opening.

In certain embodiments, the kits include two or more devices for dilating a stenotic opening of a paranasal sinus in a subject. As described herein, the devices expand from a non-expanded configuration to an expanded configuration. In some instances, the devices have the same diameter when in their respective non-expanded configurations and different diameters when in their respective expanded configurations. For example, embodiments of the kits may include a first device and a second device. The first device and the second device may have substantially the same diameter when they are in their respective non-expanded configurations. In some cases, the devices expand to their respective expanded configurations as described herein, where the second device has an expanded configuration with a diameter that is greater than the diameter of the first device when the first device is in its expanded configuration. In other embodiments, the first device and the second device have different diameters when in their respective non-expanded configurations. For instance, the second device may have a non-expanded configuration with a diameter that is greater than the diameter of the first device when the first device is in its non-expanded configuration. Upon expansion of the first and second devices, the second device may have an expanded configuration with a diameter that is greater than the diameter of the first device when the first device is in its expanded configuration.

Initially, the first device may be positioned in a stenotic opening of a paranasal sinus as described herein and maintained in place for a desired period of time. Subsequently, the first device may be removed from the stenotic opening, and if desired the second device may be positioned in the stenotic opening. As described above, the second device may have an expanded configuration with a diameter that is greater than the diameter of the first device when the first device is in its expanded configuration. In some instances, a plurality of devices may be used sequentially, such that devices with progressively larger diameters are positioned in the stenotic opening. The sequential use of a plurality of devices with progressively larger diameters may facilitate dilation of the stenotic opening.

In certain embodiments, the kits include one or more sinus ostium sizing probes. In some instances, the probes are configured to be removably mountable onto the distal end of the dilator insertion/implanting devices (e.g., on the distal end of the hollow elongated member of the device). In certain cases, the probes are of varying diameters and adapted to be inserted into the dilated ostium to determine the diameter of the dilated ostium and assess whether further dilation is needed.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., one or more pieces of paper on which the information is printed, in the packaging of the kit, in a package insert, etc. Another form would be a computer readable medium, e.g., diskette, CD, DVD, Blu-Ray, computer-readable memory, etc., on which the information has been recorded or stored. Yet another form of providing instructions to a user may be a website address which may be used via the Internet to access the information at a removed site. Any convenient means of providing instructions may be present in the kits.

EXAMPLES

Example 1

Three different designs of an osmotic dilator for dilating and remodeling the ostium of a maxillary sinus over a period of 3 to 4 hours were fabricated.

External Elastic Semipermeable Membrane Design

The osmotic driver was prepared by passing 11.0 g of ultrahigh molecular weight polyethylene oxide (Polyox™ Sentry Grade WSR 303 LEO National Formulary, having a viscosity in water at 1% solids of approximately 8,700 centipoise, and a molecular weight of approximately 7 million; Colorcon®, Inc., West Point, Pa.) through a 100-mesh sieve into a beaker. 12.5 g of sodium chloride was ground to a fine powder in a mortar with pestle and passed through the 100-mesh sieve. The polyethylene oxide and sodium chloride were mixed together in a beaker with a spatula. 1.25 g of hydroxypropyl methyl cellulose (Methocel™ E5 Premium LV having an aqueous viscosity at 2 weight percent solids of approximately 5 centipoise; Dow Chemical Company, Midland, Mich.) was sized through the 100-mesh sieve. The hydroxypropyl methylcellulose was added to the mixture and stirred with a spatula. 22 ml of denatured ethyl alcohol grade SDA3A was slowly stirred with a spatula into the powder mixture until a uniformly wet blend formed. The resulting damp mass was passed with a spatula through a 40-mesh sieve, forming elongated granules. The granules were air dried at room temperature for 3 hours, stirred with a spatula, and then dried overnight in a forced air oven set at 40° C. The dried granules were then passed again through the 40-mesh sieve and weighed. An amount of magnesium stearate tablet lubricant, equal to 1 weight percent of the weighed granules, was passed through an 80-mesh sieve and added to the granules. The lubricant was tumble mixed for 2 minutes into the blend. Portions of the resulting blend weighing 17 mg were filled into a core rod tooling punch and die set (Natoli Engineering, St. Charles, Mo.) having an inside diameter of 2.9 mm and a core rod outside diameter of 0.055 inch (0.14 cm). The punches were 2.9 mm round flat faced beveled tooling. The powders were compressed with a force of approximately 250 pounds (1110 Newtons) on a Carver press to form donut shaped tablets having a central hole of approximately 0.055 inch (0.14 cm) diameter, an outside diameter of approximately 2.9 mm, and height of approximately 2.5 mm.

Stainless steel hypodermic needle stock grade steel 304 was cut into lengths of 55 mm and ends were de-burred. The inside diameter of the tubes was 0.032 inch (0.081 cm) and the outside diameter was 0.042 inch (0.11 cm). The tubular sections were passivated by treating with nitric acid solution, then potassium hydroxide solution, rinsed with de-ionized water, and air dried. An elastomeric semipermeable membrane coating solution was prepared by tumble mixing 14.4 g of polyurethane (Tecophilic® grade HP-93A-100; Thermedics™ Polymer Products, Wilmington, Mass.). This polymer had nominal values for Shore Hardness of 83 A, for Flexural Modulus of 2,900 pounds per square inch (2000 Newtons/cm$^2$) as measured by ASTM test D790, for Ultimate Elongation in the dry state of 1,040 percent and for Ultimate Elongation in the wet state of 620 percent as measured by ASTM method D412, and for equilibrium moisture content of 100%) in 65.6 g of n-methyl pyrrolidone solvent (Pharmasolve®, ISP Technologies, Inc., Wayne, N.J.) at room temperature for 2 days.

Osmotic dilators having a configuration as shown in FIG. 23 were prepared. Passivated stainless steel tubes 151 were dipped into the semipermeable membrane coating solution multiple times to build up an inner membrane coating 152 on the tube having a thickness of approximately 0.005 inch (0.013 cm). The tubes 151 were hung vertically and dried in a current of room temperature air in a fume hood between coatings. Two osmotic salt tablets 153, 154 were threaded onto the coated stainless steel tube 151. The pair of osmotic tablets 153, 154 were positioned in the middle of the tubes 151 and set such that they were in contact with each other. The resulting subassembly was then dip coated in the same semipermeable membrane coating solution multiple times until an external elastic semipermeable membrane coating 155 having a thickness of approximately 0.015 inch (0.038 cm) was built up. The subassemblies were hung vertically and dried between coatings. To promote evenness of coating thickness, the tubes 151 were rotated 180° between coatings. The final coated subassembly was dried at room temperature in a current of air for 2 days. After drying, excess membrane material was removed from each end of the tubes 151 using a razor blade. The portion removed spanned the distance of approximately 2 mm from the edge of the osmotic drivers 153, 154 to the ends of the tubes 151. The tubes 151 were cut off at each end, with the cuts being approximately 4 mm from the edge of the osmotic salt tablets 153, 154, leaving an overall dilator 150 length of about 13 mm.

Distal and proximal anchors 156, 157 were fabricated. The proximal anchor 157 was punched from 1.7 mm sheet stock of black acrylonitrile butadiene rubber (Buna-n) in the outline shape of a dog bone. The length of the proximal anchor was 10.3 mm and the width, at the necked-down portion, was 6.5 mm. A hole was drilled through the center of the anchor using a 0.042 inch (0.11 cm) drill bit. The distal anchor 156 was made of molded black polyurethane (grade 60A) rubber having a central hole similar in size to the drilled hole of the proximal anchor 157. The distal anchor 156 had a daisy petal configuration with an outside diameter of 6.2 mm. The distal and proximal anchors 156, 157 were affixed to the stainless steel tube 151 by threading the ends of the tube 151 into the holes in the anchors 156, 157 and secured using a medical grade cyanoacrylate adhesive (Loctite 4013, Loctite Corp., Rocky Hill, Conn.).

Internal Semipermeable Membrane with External Non-Permeable Membrane Design without Wick An aluminum mandrel was machined to a cylindrical shape having distal and proximal regions of differing diameters. The proximal region had a diameter of 7.6 mm and a length of 6.8 mm. The distal region had a diameter of 2.1 mm and length of 14.7 mm. The resulting mandrel was first coated with a release coating layer of poly(p-xylylene) polymer (Parylene, Para Tech Coating, Inc., Aliso Viejo, Calif.). Then a 7 mil (0.2 mm) thick semipermeable membrane comprising 60/40 cellulose acetate poloxamer 188 was spray coated onto the mandrel. The cellulose acetate membrane was cut along the edge of the proximal end of the mandrel and removed from the mandrel. Four osmotic salt tablets having the same composition as the salt tablets used in the external membrane design (see above) were compressed with core rod tooling having an outer diameter of 3.5 mm, inside diameter of 2.5 mm, and height 2.9 mm and were threaded onto the distal end of the cellulose acetate shell. The end section of a polyethylene terephthalate (PET) 8 mm×150 mm catheter balloon was cut. The resulting catheter balloon was crimped onto the tablets by wrapping the balloon with sutures. Once crimped, the PET balloon was glued to the cellulose acetate inner membrane at the distal and proximal ends of the device. The larger diameter cellulose acetate portion acted as a proximal anchor. The distal anchor was made of molded black polyurethane (grade 60A) rubber having a central hole and secured to the stainless steel tube by threading the ends of the tube into the hole and secured using a medical grade cyanoacrylate adhesive.

Internal Semipermeable Membrane with External Non-Permeable Membrane Design with Wick This design was substantially the same as the internal rigid semipermeable membrane with external non-permeable membrane without wick design (see above), except that a 2.4 mm thick sheet of polyvinyl alcohol (PVA) open cell foam sponge (Expandacell™ sponge, Shippert Medical Technologies, Engelwood, Colo.) was positioned in the center lumen of the rigid cellulose acetate membrane at the proximal end of the device to serve as a water wicking material.

Example 2

Figure 26A:
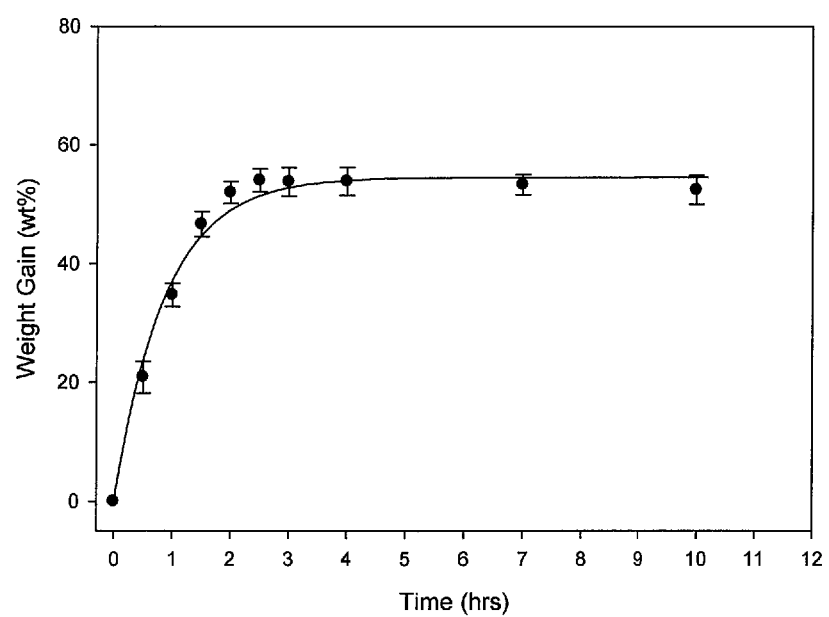
FIG. 26A is a graph of dilator weight gain (wt %) versus time for osmotic dilators tested in vitro in Example 2 hereof.
Figure 26B:
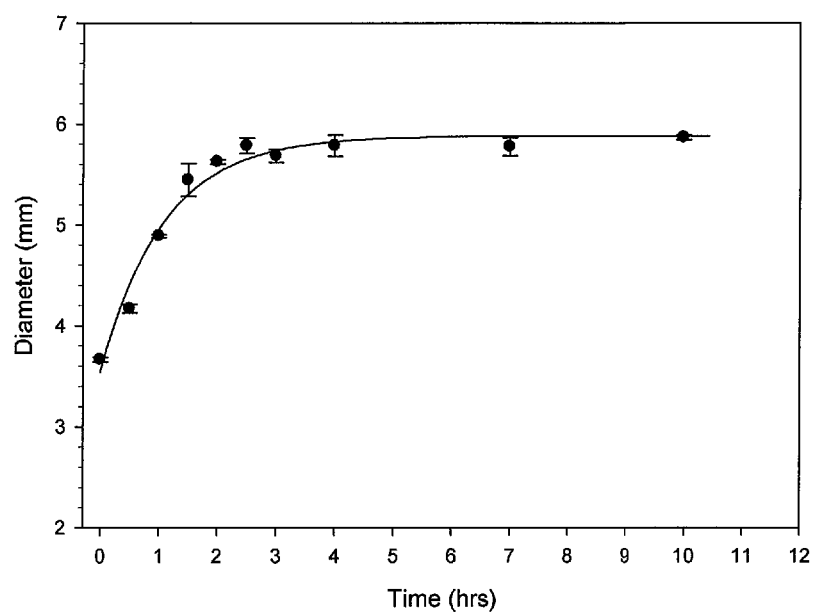
FIG. 26B is a graph of dilator diameter versus time for osmotic dilators tested in vitro in Example 2 hereof.

The performance of the external membrane design dilator 150 (see FIG. 23) made in accordance with Example 1 was evaluated in vitro. The dilators were tested in a media of 500 ml distilled water at 37° C. using a U.S. Pharmacopeia Type 2 paddle tester with a paddle speed of 50 revolutions per minute. Two dilators were tested. Dilator weight gain and diameter were monitored as a function of time. FIGS. 26A and 26B illustrate the results, respectively. The dilators 150 exhibited a steady increase in both weight and diameter over a period of approximately 4 hours. The dilators swelled uniformly and symmetrically throughout the test period to achieve a final dilated shape as shown in FIG. 24. The swelling was achieved by the salt and Polyox in tablets 153, 155 causing water to permeate through the semipermeable membrane 155, which in turn caused the Polyox to swell. The swelling tablets caused the membrane 155 to stretch in order to accommodate the increased volume of the tablets 153, 154. Once equilibrium swelling was reached, the dilators 150 stopped gaining weight and remained in the expanded state, as shown in FIG. 26A, without further expansion.

Similar testing of six of the internal membrane design system indicated for 5 out of 6 of the dilators that enhanced sealing of the glued seal between the hydrophobic PET elastic membrane and the internal hydrophilic cellulose acetate membrane may be achieved using a different adhesive and/or sealing techniques (e.g., crimping, suturing, solvent welding, sonic welding, etc.).

Example 3

The three osmotic dilator designs made in accordance with Example 1 were also tested in vivo in sheep since the sheep is a recognized model for the human sinus anatomy (Gardiner et al., *Journal of Laryngology and Otology*, May 1996, Vol. 110, 425-428). Each device was measured (outer diameter of the device), weighed and photographed prior to insertion. Under endoscopic examination using a 30 degree endoscope, a probe was first inserted into the nasal cavity of live anesthetized adult sheep and a 3 mm diameter opening was punctured through the thin wall separating the nasal cavity and maxillary sinus cavity in both maxillary sinuses of each animal. An osmotic dilator was inserted into each of the two maxillary sinus openings such that the distal anchor was located inside the maxillary sinus and the proximal anchor remained within the nasal cavity, thereby anchoring the dilators within the respective openings. After epistaxis was noted in the first few insertions, topical 0.5% oxymetazoline was applied to the lateral nasal wall before insertion. The external membrane dilators were inserted in 3 animals (6 devices), the internal membrane without wick dilators were inserted in 3 animals (6 devices) and the internal membrane with wick dilators were inserted in one animal (2 devices). After dilator insertion, the animals were awakened and returned to a holding area.

At the time of dilator extraction, the animals were sedated, the dilators removed under videoendoscopy, and the resulting ostium was measured. The extracted dilators were placed in a dry vial, measured and weighed.

Figure 27:
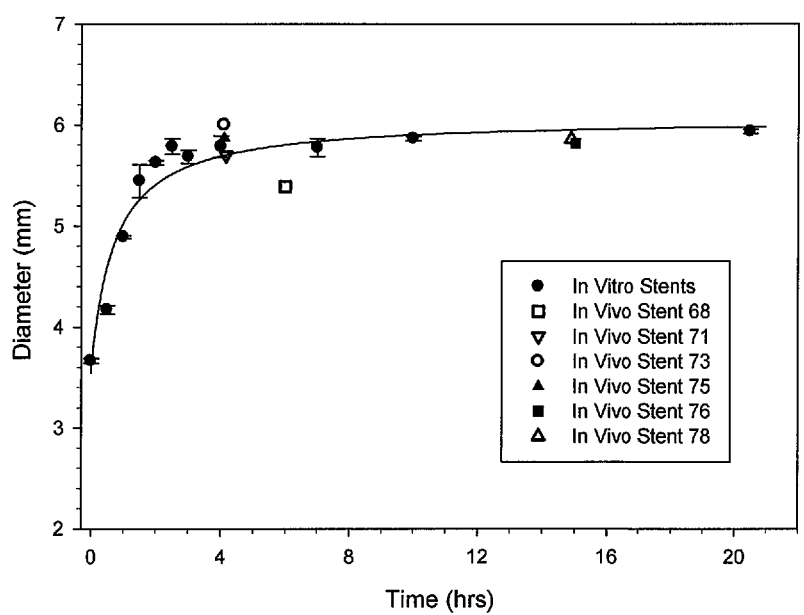
FIG. 27 is a graph of dilator diameter versus time for osmotic dilators tested in vitro in Example 2 and in vivo in Example 3 hereof.
Figure 28:
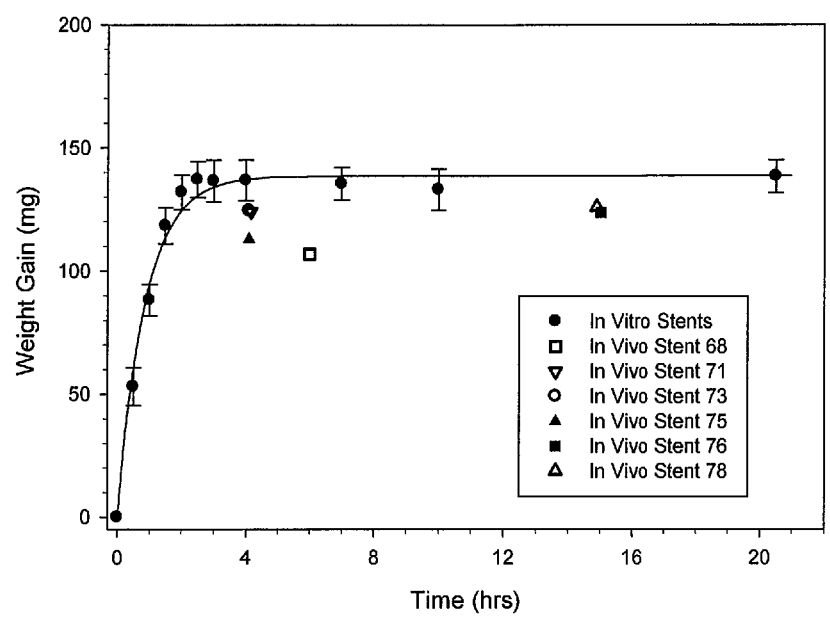
FIG. 28 is a graph of dilator weight gain (mg) versus time for osmotic dilators tested in vitro in Example 2 and in vivo in Example 3 hereof.

The external membrane dilators were left in place for 4, 6 or 15 hrs before being removed. During that time, the dilators swelled by imbibing physiological water. Dilator diameters were measured at these sampling points and are shown in FIG. 27 for only the external membrane systems. For comparison purposes, FIG. 27 also illustrates the corresponding diameters measured in vitro from Example 2. The solid circles represent the in vitro results. The open and closed squares, triangles, and open circle represent the in vivo results. Both in vitro and in vivo dilators reached an equilibrium swelling diameter of approximately 5.5 mm to 6 mm. FIG. 28 depicts the corresponding weights of the dilators. The in vivo dilators reached equilibrium weight by 4 hours and gained approximately 120 mg. The in vitro dilators reached equilibrium weight by 2 to 4 hours and gained 140 mg.

As for the internal membrane design systems, those systems were left in place for 1, 2 or 3 days before being removed. The internal membrane designs without a wick exhibited approximately a 20% increase in diameter and an 80% weight gain after 24 hrs. The internal membrane systems with the PVA wick swelled substantially more slowly than the internal membrane systems without a wick. This slower rate of swelling may be due to dried mucous tending to form on the exposed portions of the wick, which may have inhibited water from being imbibed to the internal membranes.

Figure 29:
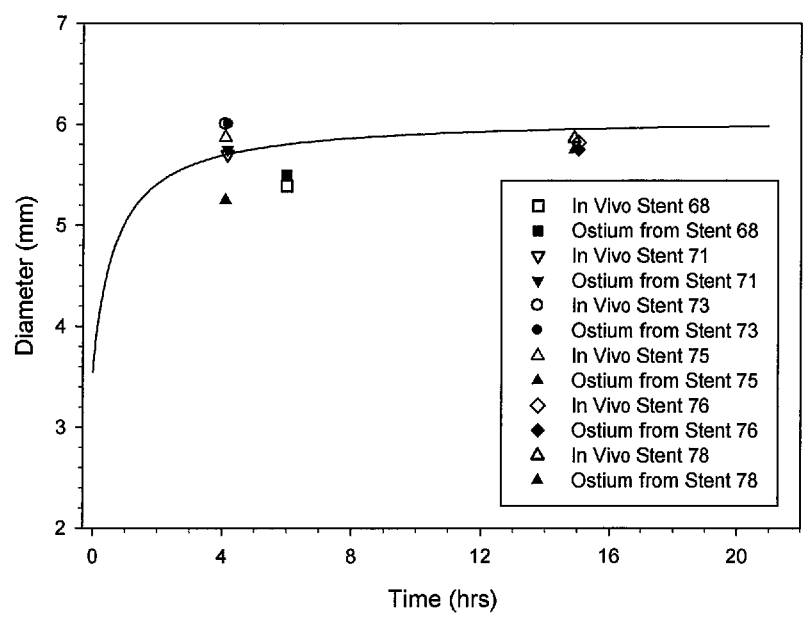
FIG. 29 is a graph of maxillary sinus opening diameter versus time following dilation with osmotic dilators tested in vivo in Example 3 hereof.

Upon retrieval of the external membrane dilators, the diameter of the opening in the maxillary sinus wall formed by the expanded dilator was measured under endoscopic examination by comparing the opening size to reference probes of known diameters. FIG. 29 shows the plot of maxillary sinus opening diameter over time. The solid symbols represent the measured values of diameter for the opening formed by the enlarged osmotic dilator. The open symbols represent the corresponding diameters of the dilators that were measured with calipers after the dilator was removed. The correlation between each pair of data is very good since in five of six instances the measured diameter of the opening closely matched the measured diameter of the dilator that formed the opening.

Figure 32:
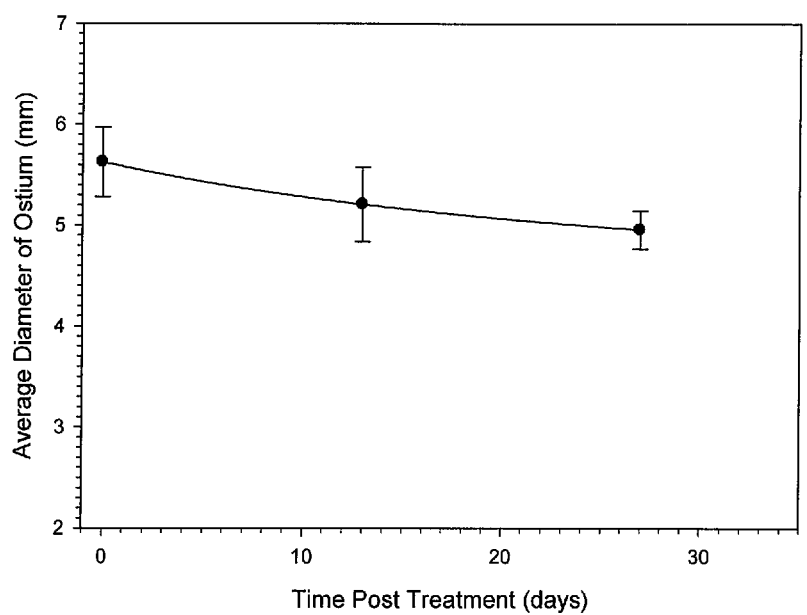
FIG. 32 is a graph of average maxillary sinus opening diameter versus time following dilation with osmotic dilators tested in vivo in Example 3 hereof.

The diameters of the dilated ostia from these animals were monitored over a period of 4 weeks post treatment in order to assess the patency of the enlarged ostia. The ostia were measured at time zero immediately following dilation treatment, 13 days, and 27 days according to the same procedures described above. FIG. 32 depicts the resulting data. The average ostium diameter declined slightly over the 27 day period, in an asymptotic response, approaching a projected final diameter of slightly less than 5 mm.

All dilators that were inserted and remained in place demonstrated dilation. For the external membrane dilators, dilation appeared to be complete at the time of the first measurement time point (4 hours after placement) and did not increase with increased insertion time. This apparent equilibrium point may indicate a "safety valve" for the system. In other words, the system does not continue to enlarge endlessly which could damage surrounding structures. It was also shown that the diameter of the opening created correlated with the diameter of the expanded dilator. This indicated that the dilators were creating long term changes in the surrounding tissue and not just temporary stretching of the tissue. Also the amount of trauma to the tissue was minimal, therefore not causing damage or tearing leading to a larger than desired opening. Finally, 27 day patency was documented in all sinuses.

Observations of the enlarged ostia compared to previous work done using balloon catheter sinuplasties are as follows. The slowly expanding osmotic dilators kept in place for several hours produced more even (i.e., a round opening with smooth surfaces) remodeling of the tissue in the sinus opening compared to short time duration/high hydraulic pressures used to inflate sinuplasty balloons. The latter high short burst of pressure tends to produce ostial openings having uneven/jagged surfaces. This comparison shows that slow expansion due to slow dilation driven by osmotic pressure applied over a longer period of time gave better ostial tissue remodeling, and resulted in less tissue damage, than the short high pressure bursts used in balloon sinuplasty.

Example 4

Osmotic dilators designed to dilate and remodel the ostium over a duration of about 20 to 24 hours were fabricated. Tubes having lengths of 55 mm were cut from 304 stainless steel hypodermic needle stock. The tubes were de-burred, then washed with an aqueous solution of Liquinox detergent, rinsed 5 times with de-ionized water, then washed with dry acetone, and air dried. An elastomeric membrane coating solution was prepared by mixing 8.0 g of polyurethane (Tecophilic® grade HP60D-20; Thermedics™ Polymer Products, Wilmington, Mass.). This elastomeric polymer had nominal values for Shore Hardness of 43D, for Flexural Modulus of 4,300 pounds per square inch (3000 Newtons/cm$^2$) as measured by ASTM test D790, for Ultimate Elongation in the dry state of 430 percent and for Ultimate Elongation in the wet state of 390 percent as measured by ASTM method D412, and for equilibrium moisture content of 20%) in 72 g of n-methyl pyrrolidone solvent (Pharmasolve®, ISP Technologies, Inc., Wayne, N.J.). The blend was tumble mixed for 2 days at room temperature to form a clear, colorless, viscous solution. The tubes were dipped in the elastomeric membrane coating solution to a depth of 45 mm multiple times to build up a coating thickness of approximately 0.005 inch (0.013 cm). Between coatings, the tubes were hung vertically and dried in a current of air in a fume hood.

Osmotic salt-containing tablets were fabricated by passing 16.0 g of polyethylene oxide (Polyox™ Sentry Grade WSR 303 LEO; Colorcon®, Inc., West Point, Pa.) through a sizing screen having 40 wires per inch (16 wires per cm). Sodium chloride, 7.5 g, was then triturated in a mortar with pestle, passed through a 60-mesh sieve, and added to the polyethylene oxide. 1.3 g of hydroxypropyl methyl cellulose (Methocel™ E5 Premium LV, The Dow Chemical Company, Midland, Mich.) was passed through the 60-mesh sieve and added to the powders. The powders were stirred with a spatula to form a pre-blend. 25 ml of anhydrous ethanol grade SD3A was slowly stirred into the powders to form a uniform, damp mass. The damp mass was forced through a 40-mesh sieve with a spatula to form elongated granules. After drying overnight in at room temperature in a fume hood, the granules were passed again through a 40-mesh sieve, yielding 21.35 g of granules. Magnesium stearate tableting lubricant, 216 mg, was passed through an 80-mesh sieve and added to the dried, sized granules. The mixture was tumbled in a 120 cm$^3$ screw-capped bottle for one minute to form the final osmotic engine blend composition. The resulting composition was compacted with 2.9 mm flat-faced round punches and dies to a nominal weight of 22.5 mg using an applied load of 250 pounds (1110 Newtons) with a Carver press to form compressed tablets. The nominal height of the tablets was 2.5 mm. A central hole was drilled in the middle of the face of the tablets using a 0.055 inch (0.14 cm) drill bit. After drilling, the nominal weight of the tablets was 16 mg.

Four osmotic salt tablets were threaded onto each of the coated stainless steel tubes. The tablets were positioned in the middle of the 55 mm tube length and in contact with each other to produce a continuous stack of tablets. The subassembly was then dipped into the same elastomeric membrane coating solution used to coat the stainless steel tubes. The subassemblies were dipped multiple times in order to build up a coating thickness on the tablets of approximately 0.014 inch (0.036 cm). Between coatings, the subassemblies were hung vertically and dried in a current of room temperature air. The excess membrane coatings over the tube ends were trimmed off with a razor following the same procedure described in Example 1. The ends of the tubes were then cut to an overall length of about 14 mm, leaving approximately 2 mm of bare metal exposed at each end of the tubes. Proximal and distal anchors were then attached to the metal tubes as described in Example 1 to complete fabrication of the osmotic dilators.

Example 5

Figure 30:
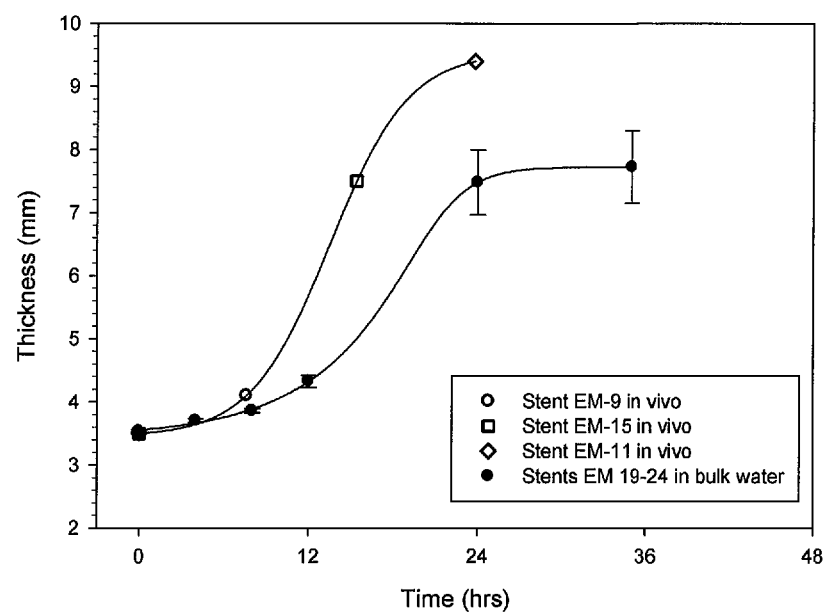
FIG. 30 is a graph of dilator diameter versus time for osmotic dilators tested in vitro in Example 5 and in vivo in Example 6 hereof.
Figure 31:
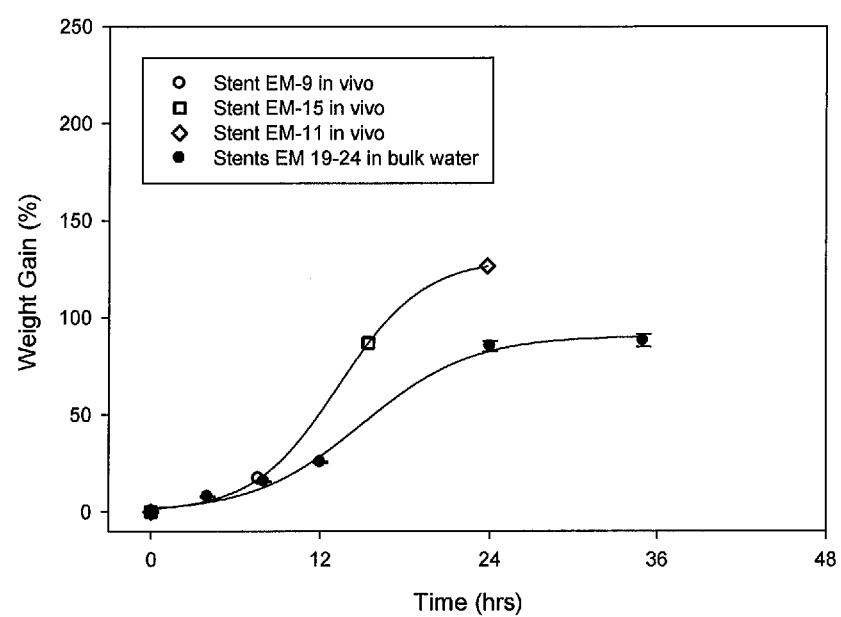
FIG. 31 is a graph of dilator weight gain (wt %) versus time for osmotic dilators tested in vitro in Example 5 and in vivo in Example 6 hereof.

Osmotic dilators made in accordance with Example 4 were tested in vitro in 50 ml of unstirred distilled water at 37° C. Diameter and weight gain of the dilators were monitored as a function of time in this media. The solid symbols illustrated in FIG. 30 represent the diameter versus time. The osmotic dilators steadily expanded through approximately 24 hours. The corresponding data representing weight gain of the dilators as a function of time in vitro are illustrated in FIG. 31. These weight gain curves of FIG. 31 follow the diameter gain curves of FIG. 30.

Example 6

Osmotic dilators made in accordance with Example 4 were tested in vivo in sheep by inserting the dilator in an opening connecting the nasal cavity and the maxillary sinus as described in Example 3. The dilators were retrieved at 4, 17, and 24 hours and thickness and weight gain were monitored. These in vivo data are plotted as open symbols in FIG. 30 (together with the in vitro data from Example 5) and illustrate a steady increase in diameter over time, reaching a maximum diameter in approximately 24 hours. The corresponding data representing weight gain of the dilators as a function of time in vivo are illustrated in FIG. 31 (together with the in vitro data from Example 5). These weight gain curves of FIG. 31 follow the diameter gain curves of FIG. 30.

Example 7

A self-centering osmodilator is fabricated which is designed to nest within the sinus ostium. A non-collapsing tube is coated with elastomeric polyurethane according to the procedures and compositions described in Example 4. A single osmotic driver is threaded onto the middle of the 55 mm coated tube. The resulting subassembly is dip coated multiple times and dried until the elastomeric coating on the osmotic driver is built up to a nominal thickness of 0.003 inch (0.008 cm). Another osmotic driver is threaded onto each end of the coated tube such that a gap of about 1.5 mm is present between the first (middle) coated driver and the two end drivers which are not yet coated. The resulting subassembly is then dip coated such that the middle driver and an end driver are dip coated. After drying, the dilator is inverted 180° and dip coated such that the other end driver located at the opposite end of the tube and middle driver are coated. This process is repeated multiple times such that the coating on the end drivers is always less than the coating thickness of the middle driver. Each end of the tube is cut off and anchors are attached, according the procedures described in Example 4.

When placed in an ostium, the osmotic drivers located on the ends of the dilator, which have thinner membranes, imbibe physiological water faster than the middle driver, which has a thicker membrane coating. As the osmotic drivers continue to imbibe water, the dilator transforms into a barbell configuration, which configuration nests into the ostia and centers the dilator between the proximal and distal surfaces of the wall of the sinus (e.g., a maxillary sinus).

Example 8

An osmodilator is made according to the procedures described in Example 1 except the subcoat elastomeric tube, the osmotic drivers, and the overcoat elastomeric tube are each formed by injection molding.

Example 9

An osmotic dilator which forms rib elements which help retain the dilator within a sinus ostium is made. The osmotic dilator is made according to the compositions and procedures described in Example 4. Prior to the final applications of elastomeric coating, three equally-spaced hoops are placed around the stack of four osmotic drivers. The hoops can comprise stainless steel, high tensile strength wire, thread, suture, floss, or high tensile strength molded or machined ring material. After the hoops are installed, the final applications of membrane coating are applied, thereby embedding the three hoops within the membrane structure. When placed in an aqueous environment, such as the sinus ostium, water is imbibed by osmotic activity causing the stack of osmotic drivers to swell and distend the external elastomeric membrane. As the membrane and osmotic drivers enlarge, swelling is constrained and directed by the hoops such that ribbed elements form between the hoops. This directed swelling produces radial expansion between the hoops larger than would be present without the hoops. Additionally, the ribbed elements assist in retaining the device within the ostia by providing convoluted surfaces within which the ostia can reside during treatment.

Example 10

An osmotic dilator is fabricated according to Example 9 except that a wire mesh cage is present instead of the hoops. The mesh cage provides the elastomeric membrane with a frictional surface that enhances retention of the dilator while it undergoes expansion within the sinus ostia.

Example 11

An osmotic dilator is fabricated according to Example 9 except that a braided, knitted, non-woven, or woven polymeric tube is present instead of the hoops. The texture of the tube provides the elastomeric membrane with a frictional surface that enhances retention of the dilator while it undergoes expansion within the sinus ostia.

Example 12

Figure 25:
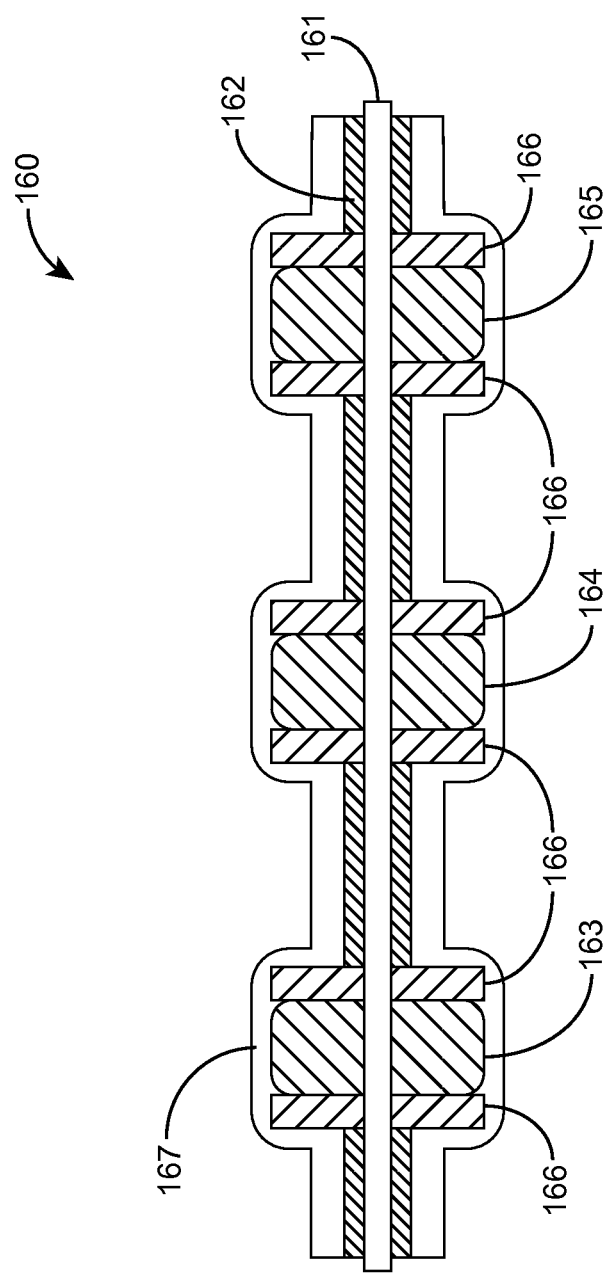
FIG. 25 is a sectional view of an embodiment of an osmotically driven device for dilating a paranasal sinus opening, in a non-expanded configuration, according to embodiments of the present disclosure.

A self-positioning (e.g., self-centering) sinus ostium dilator 160 having spaced salt tablets 163, 164, 165 is shown in FIG. 25. Pieces of 304 stainless steel tube stock 161 having an inside diameter of 0.032 inch (0.081 cm), an outside diameter of 0.042 inch (0.11 cm) and a length of 55 mm were dip coated in an elastomeric semipermeable membrane coating solution comprising a 10 wt % solids solution of polyurethane (Tecophilic grade HP60D-20; Thermedics™ Polymer Products, Wilmington, Mass.) dissolved in n-methyl pyrrolidone. The tubes 161 were dip coated multiple times until a membrane coating 162 having a nominal coating thickness of 0.005 inch (0.01 cm) had accumulated on the middle of each of the tubes 161. The tubes 161 were dried in a current of room temperature air between coatings. Polyether ether ketone polymer stock was machined to form microwashers 166 having an inner opening diameter of 0.055 inch (0.14 cm), an outside diameter of 0.110 inch (0.28 cm) and a thickness of 0.020 inch (0.05 cm). The average weight of the microwashers 166 was 3 mg. Three osmotic salt-containing tablets 163, 164, 165 equivalent to those disclosed in Example 4 and six microwashers 166 were then threaded onto the coated stainless steel tubes 161 such that a microwasher 166 was placed in contact with each tablet as shown in FIG. 25, forming three distinct sets of microwasher+salt tablet+microwasher sandwiched subassemblies. Additionally, a 1.5 mm gap was provided between the middle and the end subassemblies. Next, the tubes 161 with subassemblies were dip coated multiple times in the same membrane coating solution until a continuous elastomeric semipermeable membrane coating 167 on the salt tablets 163, 164, 165 was developed. Between dip coatings, the dilators 160 were dried in a current of room temperature air. At each coating, the middle salt tablet 164 and one of the two end salt tablets 163, 165 were coated. Then, on the next application, the dilator was inverted 180° and the middle salt tablet 164 was coated again and the other of the two end salt tablets 163, 165 was coated. In such a process, the middle salt tablet 164 accumulated a thicker membrane 167 coating, due to more coats, than the end salt tablets 163, 165 such that at the completion of the coating cycle, the middle salt tablet 164 had a coating thickness of 0.021 inch (0.053 cm) while the end salt tablets 163, 165 had coatings with thickness values in the range of 0.015 to 0.017 inch (0.038 to 0.043 cm). Proximal and distal anchors as described in Example 1 (not shown in FIG. 25) are optionally attached the ends of the tubes 161.

When in an aqueous environment such as a sinus ostium (e.g., a maxillary sinus ostium), the osmotic dilators 160 imbibe physiological fluids causing radial distension of the outer elastomeric semipermeable membrane 167. The end salt tablets 163, 165 imbibe fluid at a faster rate than the middle salt tablet 164 which has a thicker coating of membrane 167. The net result of these different imbibition rates is that the dilator 160 forms a dumb bell configuration that helps to nest and position the dilator within the sinus ostium. The microwashers serve to direct swelling radially outwardly to further improve ostium dilation.

Example 13

An osmotic dilator designed to dilate and remodel a sinus ostium (e.g., of a maxillary sinus) is fabricated according to the methods and materials described in Example 1 except the membrane comprises a blend of two water-insoluble polymers. The blend of polymers consists of 50 weight percent of Tecophilic® HP93A-100 (Thermedics™ Polymer Products, Wilmington, Mass.) and 50 weight percent Tecophilic® HP60D-20 (Thermedics™ Polymer Products, Wilmington, Mass.). When placed in the aqueous environment of the ostia, the dilator imbibes water, swells, and reaches osmotic equilibrium over duration of 8 to 16 hours.

Example 14

An osmotic dilator for dilating and remodeling a sinus ostium (e.g., of a maxillary sinus) is fabricated according to the methods and materials described in Example 1 except the membrane comprises a blend of a water insoluble polymer and a water soluble flux enhancer. The blend of polymers consists of 90 weight percent of Tecophilic® HP93A-100 (Thermedics™ Polymer Products, Wilmington, Mass.) as the water insoluble polymer and 10 weight percent poloxamer 188. When placed in the aqueous environment of the ostia, the dilator imbibes water, swells, and reaches osmotic equilibrium over duration of about 2 hours.

Example 15

An osmotic dilator for dilating and remodeling a sinus ostium (e.g., of a maxillary sinus) is fabricated according to the methods and materials described in Example 1 except the membrane comprises a blend of a water insoluble polymer and a water soluble flux enhancer. The blend of polymers consists of 70 weight percent of Tecophilic® HP93A-100 (Thermedics™ Polymer Products, Wilmington, Mass.) as the water insoluble polymer and 30 weight percent polyvinyl pyrrolidone 12 PF. When placed in the aqueous environment of the ostia, the dilator imbibes water, swells, and reaches osmotic equilibrium over duration of about 0.5 hours.

Example 16

A phase 1, open-label study to assess the safety and performance of the osmotic dilator shown in FIG. 23 for dilation of the maxillary sinus ostium (MSO) for up to 8 hours in humans is performed. The primary endpoints of this study are (1) efficacy as defined by the patency (and diameter) of the MSO immediately after removal of the osmotic device; and (2) safety as determined by the frequency of adverse events related to the procedure. The secondary endpoints of this study are (1) device success, as defined as successful access and deployment of the osmotic dilator to the target site; (2) patency (diameter) of the MSO one week after dilator removal; (3) patency (diameter) of the MSO one month after dilator removal; (4) patency (diameter) of the MSO three months after dilator removal; (5) assessment of pain on a point scale (0 to 4) or visual analog scale (VAS) scale during dilatation; and (6) consumption of pain rescue medication.

This study is a single-arm, open-label, prospective study and will involve the collection of demographic, image and clinical data. Up to 10 subjects are recruited using the following inclusion criteria: (1) age between 18 and 70 years; (2) both males and females are eligible; (3) subject has the ability to follow the study instructions, is willing to be available on the specific required study visit days, and is willing to complete all study visit procedures and assessments; (4) subject must understand the research nature of this study and sign an informed consent prior to the performance of any study specific procedure or assessment; and the following exclusion criteria: (1) subject is pregnant or breast feeding; (2) subject has one of the following diagnoses: cytic fibrosis, Sampter's Triad (aspirin sensitivity, asthma, sinonasal polyps), nasal polyposis, sinonasal tumors, allergic fungal sinusitis, ciliary disfunction, perforated septum, atrophic nasal mucosa, and/or excessive osteogenesis; (3) subject has any anatomic abnormality that precludes access to the maxillary sinus ostium (e.g., a deviated septum); (4) subject has a history of facial trauma that resulted in distortion of the nasal and/or sinus anatomy; (5) subject has had a previous antrostomy; (6) subject has clinical evidence of acute respiratory or sinus infection; (7) subject has a known infection with human immunodeficiency virus, other immune deficiency, insulin dependent diabetes or other serious systemic disease; (8) subject is currently participating in, or has participated in, any type of investigational study in the thirty days prior to screening visit; (9) subject has known sensitivity to the local anesthetic agent used in the study; (10) subject has a diagnosis of hematologic disease, bleeding diathesis or is taking anticoagulant medication; and (11) any other condition which in the investigator's opinion deems the subject an unsuitable candidate to receive study treatment or which may interfere with the study results. Enrolled subjects undergo local anaesthesia/decongestant followed by a nasal endoscopy. Standardized photographs/videos are taken at baseline (i.e., prior to any dilation treatment). Patency and if applicable diameter of the MSO prior to dilatation is recorded. The osmotic dilator is inserted, using the inserter illustrated in FIG. 37, in the MSO under endoscopic visualization. One device is inserted in each of the subjects two MSOs. The devices are left in the MSO for up to 8 hours. The devices are removed upon the subject's request or if the investigator deems it necessary. Consumption of rescue medications during the dilation is recorded. Adverse events and tolerability are evaluated and recorded. The dilator is removed using the same tool as used for dilator insertion. Standardized photographs/videos are taken immediately after dilator removal. The patency and diameter of the MSO immediately after dilatation is recorded. Upon removal, the devices are measured, weighed and photographed. Follow-up visits are conducted at one week, one month and three months after MSO dilation. Standardized photographs/videos are taken, the patency and diameter of both MSOs is recorded, and all adverse events are assessed and recorded. This clinical testing shows that the osmotic dilators are effective to increase the opening diameter of a maxillary sinus ostium from substantially closed (e.g., 0 mm diameter) to a diameter of about 5 mm with minimal tissue damage and resulting inflammation response, and the opening remains patent for 3 months or more following the dilation procedure.

Example 17

An osmotic dilator designed to dilate and remodel the ostium of a maxillary sinus over a duration of minutes was fabricated according to the methods and materials described in Example 1, except the membrane had a nominal thickness of 348 microns (13.7 mils). When three stents were placed in deionized water at 37° C. for 120 minutes, the devices imbibed an average of 125 mg water and swelled from an initial diameter of 3.6 mm to an expanded diameter of 5.6 mm.

Example 18

An osmotic dilator designed to dilate and remodel the ostium of a maxillary sinus over a duration of minutes was fabricated according to the methods and materials described in Example 1, except the membrane was formed by extrusion. A tube made of Tecophilic® HP93A-100 (Thermedics™ Polymer Products, Wilmington, Mass.) was extruded having a nominal inside diameter of 44 mils (1.12 mm) and nominal wall thickness of 5 mils (0.127 mm). The extruded tube was slipped onto the stainless steel tube described in Example 1. Then, two osmotic tablets as described in Example 1 were positioned over the extruded tube such that they were in contact with each other. A second tube of Tecophilic® HP93A-100 (Thermedics™ Polymer Products, Wilmington, Mass.) was extruded having a nominal inside diameter of 116 mils (2.95 mm) and a nominal wall thickness of 14 mils (0.356 mm). The second tube was then slipped over the osmotic tablets. The inner first tube and outer second tube were heated locally at each side of the pair of osmotic tablets using a hot iron such that the first and second tubes adjacent to the engines were melted and bonded to form a continuous seal between the inner and outer tubes, thereby fully encapsulating the osmotic tablets with the membrane material. The resulting device was placed in deionized water at 37° C. and the device imbibed water from the environment. The device swelled from an initial diameter of 3.7 mm to a final diameter of 5.25 mm over a period of 90 minutes.

Example 19

An osmotic dilator designed to dilate and remodel the ostium of a maxillary sinus over a duration of minutes is fabricated according to the methods and materials described in Example 18, except the membrane is sealed by solvent welding.

Example 20

An osmotic dilator designed to dilate and remodel the ostium of a maxillary sinus over a duration of minutes is fabricated according to the methods and materials described in Example 18, except the membrane is sealed by sonic welding.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting, since the scope of the present invention will be embodied only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A method of dilating a stenotic opening of a paranasal sinus in a subject, the method comprising:
    positioning a device in the stenotic opening, wherein the device comprises:
        (a) two or more self-expanding drivers configured to expand an expandable portion from a non-expanded configuration to an expanded configuration in a substantially radial direction with respect to a longitudinal axis of the device with a pressure ranging from 1 atm to 500 atm, wherein the two or more drivers comprise a proximal driver proximate to the proximal end of the device and a distal driver proximate to the distal end of the device; and
        (b) the expandable portion disposed peripherally around the two or more drivers and configured to expand from the non-expanded configuration to the expanded configuration, wherein the non-expanded configuration is sized to be positioned within the stenotic opening,
    wherein the two or more drivers expand the expandable portion from the non-expanded configuration to the expanded configuration over a period of 1 hour or more while the device is positioned in the stenotic opening, thereby dilating the stenotic opening.

2. The method of claim 1, wherein the two or more drivers expand the expandable portion from the non-expanded configuration to the expanded configuration over a period of 4 hours or more.

3. The method of claim 1, comprising removing the device from the stenotic opening at a point in time after the device has expanded to the expanded configuration.

4. The method of claim 1, wherein the paranasal sinus is a frontal sinus, a sphenoid sinus or a maxillary sinus.

5. The method of claim 4, wherein the paranasal sinus is a maxillary sinus and the expanded configuration has a diameter ranging from 5 mm to 10 mm.

6. The method of claim 4, wherein the paranasal sinus is a frontal sinus and the expanded configuration has a diameter ranging from 3 mm to 5 mm.

7. The method of claim 4, wherein the paranasal sinus is a sphenoid sinus and the expanded configuration has a diameter ranging from 5 mm to 10 mm.

8. The method of claim 1, wherein the device comprises at least one anchor configured to maintain the device within the stenotic opening.

9. The method of claim 8, comprising anchoring the device within the stenotic opening.

10. The method of claim 1, wherein the two or more drivers expand the expandable portion by at least one of osmosis, a shape memory metal, a spring, a swellable polymer, a thermal expansion of a gas, a thermal expansion of a liquid, a gas-generating chemical reaction and a phase change expansion of a material.

11. The method of claim 1, wherein the two or more drivers comprise an osmotically active agent.

12. The method of claim 1, wherein the expandable portion dilates the stenotic opening such that a greater amount of drainage is allowed through the stenotic opening as compared to the undilated stenotic opening.

13. The method of claim 1, wherein the expandable portion comprises a semipermeable membrane.

14. The method of claim 1, comprising delivering a drug from the device while the device is positioned within the stenotic opening.

15. The method of claim 14, wherein the drug comprises an antibiotic, an anti-inflammatory drug, a local anesthetic, an analgesic or a combination thereof.

16. The method of claim 1, wherein the method is for the treatment of a subject having sinusitis.

17. The method of claim 1, wherein the non-expanded configuration has a diameter of 5 mm or less.

18. The method of claim 1, wherein the expandable portion dilates the stenotic opening such that a greater amount of ventilation is allowed through the stenotic opening as compared to the undilated stenotic opening.

19. The method of claim 1, wherein the pressure ranges from 2 atm to 25 atm.

20. A method of dilating a stenotic opening of a paranasal sinus in a subject, the method comprising:
  positioning a device in the stenotic opening, wherein the device comprises:
    (a) two or more self-expanding drivers comprising an osmotically active agent and configured to expand an expandable portion from a non-expanded configuration to an expanded configuration with a pressure ranging from 1 atm to 500 atm, wherein the two or more drivers comprise a proximal driver proximate to the proximal end of the device and a distal driver proximate to the distal end of the device; and
    (b) the expandable portion disposed peripherally around the two or more drivers and configured to expand from the non-expanded configuration to the expanded configuration, wherein the non-expanded configuration is sized to be positioned within the stenotic opening,
  wherein the two or more drivers expand the expandable portion from the non-expanded configuration to the expanded configuration over a period of 0.5 hours or more while the device is positioned in the stenotic opening, thereby dilating the stenotic opening.

21. The method of claim 20, comprising removing the device from the stenotic opening at a point in time after the device has expanded to the expanded configuration.

22. The method of claim 20, wherein the paranasal sinus is a frontal sinus, a sphenoid sinus or a maxillary sinus.

23. The method of claim 22, wherein the paranasal sinus is a maxillary sinus and the expanded configuration has a diameter ranging from 5 mm to 10 mm.

24. The method of claim 22, wherein the paranasal sinus is a frontal sinus and the expanded configuration has a diameter ranging from 3 mm to 5 mm.

25. The method of claim 22, wherein the paranasal sinus is a sphenoid sinus and the expanded configuration has a diameter ranging from 5 mm to 10 mm.

26. The method of claim 20, wherein the device comprises at least one anchor configured to maintain the device within the stenotic opening.

27. The method of claim 26, comprising anchoring the device within the stenotic opening.

28. The method of claim 20, wherein the expandable portion dilates the stenotic opening such that a greater amount of drainage is allowed through the stenotic opening as compared to the undilated stenotic opening.

29. The method of claim 20, wherein the expandable portion comprises a semipermeable membrane.

30. The method of claim 20, comprising delivering a drug from the device while the device is positioned within the stenotic opening.

31. The method of claim 30, wherein the drug comprises an antibiotic, an anti-inflammatory drug, a local anesthetic, an analgesic or a combination thereof.

32. The method of claim 20, wherein the method is for the treatment of a subject having sinusitis.

33. The method of claim 20, wherein the non-expanded configuration has a diameter of 5 mm or less.

34. The method of claim 20, wherein the pressure ranges from 2 atm to 25 atm.

35. A method of dilating a stenotic opening of a paranasal sinus in a subject, the method comprising:
  positioning a device in the stenotic opening, wherein the device comprises:
    (a) an expandable portion configured to expand from a non-expanded configuration to an expanded configuration, wherein the non-expanded configuration is sized to be positioned within the stenotic opening; and
    (b) two or more self-expanding drivers configured to expand the expandable portion from the non-expanded configuration to the expanded configuration in a substantially radial direction with respect to a longitudinal axis of the device with a pressure ranging from 1 atm to 500 atm, wherein the two or more drivers comprise a proximal driver proximate to the proximal end of the device and a distal driver proximate to the distal end of the device,
  wherein the two or more drivers expand the expandable portion from the non-expanded configuration to the expanded configuration over a period of 0.5 hours or more while the device is positioned in the stenotic opening, thereby dilating the stenotic opening.

36. The method of claim 35, comprising removing the device from the stenotic opening at a point in time after the device has expanded to the expanded configuration.

37. The method of claim 35, wherein the paranasal sinus is a frontal sinus, a sphenoid sinus or a maxillary sinus.

38. The method of claim 37, wherein the paranasal sinus is a maxillary sinus and the expanded configuration has a diameter ranging from 5 mm to 10 mm.

39. The method of claim 37, wherein the paranasal sinus is a frontal sinus and the expanded configuration has a diameter ranging from 3 mm to 5 mm.

40. The method of claim 37, wherein the paranasal sinus is a sphenoid sinus and the expanded configuration has a diameter ranging from 5 mm to 10 mm.

41. The method of claim 35, comprising anchoring the device within the stenotic opening.

42. The method of claim 35, wherein the two or more drivers expand the expandable portion by at least one of osmosis, a shape memory metal, a spring, a swellable polymer, a thermal expansion of a gas, a thermal expansion of a liquid, a gas-generating chemical reaction and a phase change expansion of a material.

43. The method of claim 35, wherein the expandable portion comprises a semipermeable membrane.

44. The method of claim 35, comprising delivering a drug from the device while the device is positioned within the stenotic opening.

45. The method of claim 44, wherein the drug comprises an antibiotic, an anti-inflammatory drug, a local anesthetic, an analgesic or a combination thereof.

46. The method of claim 35, wherein the method is for the treatment of a subject having sinusitis.

47. The method of claim 35, wherein the two or more drivers expand the expandable portion from the non-expanded configuration to the expanded configuration over a period of 0.5 hours to 1 hour.

48. The method of claim 35, wherein the non-expanded configuration has a diameter of 5 mm or less.

49. The method of claim 35, wherein the pressure ranges from 2 atm to 25 atm.

\* \* \* \* \*